US011752193B2

(12) United States Patent
Rincon et al.

(10) Patent No.: US 11,752,193 B2
(45) Date of Patent: *Sep. 12, 2023

(54) ADMINISTERING METHYLATION-CONTROLLED J PROTEIN (MCJ) SIRNA TO A KIDNEY CELL

(71) Applicant: University of Vermont and State Agricultural College, Burlington, VT (US)

(72) Inventors: Mercedes Rincon, Aurora, CO (US); Ketki M. Hatle, Jamaica Plain, MA (US)

(73) Assignee: University of Vermont and State Agricultural College, Burlington, VT (US)

( * ) Notice: Subject to any disclaimer, the term of this patent is extended or adjusted under 35 U.S.C. 154(b) by 175 days.

This patent is subject to a terminal disclaimer.

(21) Appl. No.: 17/061,912

(22) Filed: Oct. 2, 2020

(65) Prior Publication Data
US 2021/0023172 A1  Jan. 28, 2021

Related U.S. Application Data

(63) Continuation of application No. 15/805,534, filed on Nov. 7, 2017, now Pat. No. 10,792,330, which is a continuation of application No. 14/413,927, filed as application No. PCT/US2013/049885 on Jul. 10, 2013, now Pat. No. 10,583,169.

(60) Provisional application No. 61/670,345, filed on Jul. 11, 2012.

(51) Int. Cl.
| | |
|---|---|
| *A61K 38/17* | (2006.01) |
| *A61K 48/00* | (2006.01) |
| *A61K 45/06* | (2006.01) |
| *G01N 33/68* | (2006.01) |

(52) U.S. Cl.
CPC .......... *A61K 38/1709* (2013.01); *A61K 38/17* (2013.01); *A61K 45/06* (2013.01); *A61K 48/00* (2013.01); *G01N 33/68* (2013.01)

(58) Field of Classification Search
None
See application file for complete search history.

(56) References Cited

U.S. PATENT DOCUMENTS

| | | | |
|---|---|---|---|
| 5,922,567 A | 7/1999 | Au-Young | |
| 6,001,598 A | 12/1999 | Au-Young | |
| 6,043,222 A | 3/2000 | Au-Young | |
| 6,222,029 B1 | 4/2001 | Edwards et al. | |
| 6,916,609 B1 | 7/2005 | Au-Young | |
| 8,354,237 B2 | 1/2013 | Rincon et al. | |
| 2008/0261217 A1 | 10/2008 | Melnikov et al. | |
| 2010/0129931 A1 | 5/2010 | Rincon et al. | |

FOREIGN PATENT DOCUMENTS

| | | |
|---|---|---|
| WO | 2006/068440 A1 | 6/2006 |
| WO | 2008/097467 A1 | 8/2008 |

OTHER PUBLICATIONS

Huang et al., Front. Bioeng. Biotechnol. 9:683247. doi: 10.3389/fbioe.2021.683247 (Year: 2021).*
Young, J. et al., "More than folding: localized functions of cytosolic chaperones", Trends in Biochemical Science, Oct. 2003, vol. 28, pp. 541-547.
Zhang, J. et al., "Osthole improves alcohol-induced fatty liver in mice by reduction of hepatic oxidative stress", Phytother Res., May 2011, vol. 25, pp. 638-643. (Abstract only, 1 page).
Zhu, F. et al., "COOH-terminal Src Kinase-Medicated c-Jun Phosphorylation Promotes c-Jun Degradation and Inhibits Cell Transformation", Cancer Research, Jun. 1, 2006, vol. 66, pp. 5729-5736.
Musti, A. et al., "Reduced Ubiquitin-Dependent Degradation of c-Jun After Phosphorylation by MAP Kinases", Science, Jan. 17, 1997, vol. 275, pp. 400-402.
Saraswathi, V., et al., "Fish Oil Increases Cholesterol Storage in White Adipose Tissue with Concomitant Decrease in Inflammation, Hepatic Steatosis, and Atherosclerosis in Mice 1,2", The Journal of Nutrition, May 2007, pp. 776-1782.
Shi et al., "Biodistribution of Small Interfering RNA at the Organ and Cellular Levels after Lipid Nanoparticle-mediated Delivery." Journal of Histochemistry & Cytochemistry 59(8), 727-740, 2011.
Van Bulck, Michael, et al., "Novel Approaches for the Treatment of Alzheimer's and Parkinson's Disease." Int. J. Mol. Sci. 2019, 20(3), 719.
Hamanaka, RB. and Chan Del, N.S., "Mitochondrial reactive oxygen species regulate cellular signaling and dictate biological outcomes", Trends Biochem Sci, Sep. 2010, vol. 35, pp. 505-513.
Hamilton et al., "A Species of Small Antisense RNA in Post-transcriptional Gene Silencing in Plants." Science, Oct. 29, 1999, vol. 286, pp. 950-952.
Harbottle, A. et al., "Role of Glutathione S-Transferase P1, P-Glycoprotein and Multidrug Resistance-Associated Protein 1 in Acquired Doxorubicin Resistance", Int J Cancer, Jun. 15, 2001, vol. 92, pp. 777-783.
Harker, W. et al., "Multidrug (Pleiotropic) Resistance in Doxorubicin-selected Variants of the Human Sarcoma Cell Line MES-SA", Cancer Research, Sep. 1985, vol. 45, pp. 4091-4096.
Hatle, K. et al., "MCJ/DnaJC15, an Endogenous Mitochondrial Repressor of the Respiratory Chain That Controls Metabolic Alterations", Molecular and Cellular Biology, Jun. 2013, vol. 33, pp. 2302-2314.

(Continued)

*Primary Examiner* — Christina M Borgeest
(74) *Attorney, Agent, or Firm* — Pierce Atwood LLP

(57) ABSTRACT

The invention relates, in part, to methods and compositions that are useful to modulate metabolic function of cells in vivo or in vitro. In some aspects the invention includes methods and/or compositions that increase metabolism in cells, tissues, organs, and/or subjects. In certain aspects the invention includes methods and/or compositions useful to decrease metabolism in cells, tissues, organs, and/or subjects.

5 Claims, 13 Drawing Sheets

Specification includes a Sequence Listing.

(56) References Cited

OTHER PUBLICATIONS

Hatle, K. et al., "Methylation-Controlled J Protein Promotes c-Jun Degradation to Prevent ABCB1 Transporter Expression", Molular and Cellular Biology, Apr. 2007, vol. 27, pp. 2952-2966.

Hayashi, M. et al., "A crucial role of mitochondrial Hsp40 in preventing dilated cardiomyopathy", Nat Med, Jan. 2006, vol. 12, pp. 128-132.

Hogquist, K.A. et al., "T cell receptor antagonist peptides induce positive selection", Cell, Jan. 1994, vol. 76, pp. 17-27.

Holm, P. et al., "Functional mapping and single chain construction of the anti-cytokeratin 8 monoclonal antibody TS1", Molecular Immunology, Feb. 2007, vol. 44, pp. 1075-1084.

Hosoda, A. et al., Positive contribution of ERdj5/JPDI to endoplasmic reticulum protein quality control in the salivary gland, Biochem J, Sep. 2009, vol. 425, pp. 117-125.

Hu, YB and XY Liu, "Protective effects of SP600125 in a diet-induced rat model of non-alcoholic steatohepatitis," S, cand J Gastroenterol., 2009, vol. 44, pp. 1356-1362. (Abstract only, 1 page).

Hunter, P.J. et al., "Mrj encodes a DnaJ-related co-chaperone that is essential for murine placental development", Development, Mar. 1999, vol. 126, pp. 1247-1258.

Huston, J. et al., "Protein engineering of antibody binding sites: Recovery of specific activity in an anti-digoxin single-chain Fv analogue produced in *Escherichia coli*", Proc Natl Acad Sci. USA, Aug. 1988, vol. 85, pp. 8579-8583.

International Preliminary Report on Patentability dated Jan. 22, 2015 from corresponding International Patent Application PCT/US2013/049885.

International Search Report and the Written Opinion of the International Searching Authority dated Oct. 21, 2013 from corresponding International Patent Application No. PCT/US2013/049885.

International Preliminary Report on Patentability dated Aug. 4, 2009 for corresponding International Patent Application PCT/US2008/001357.

International Preliminary Report on Patentabilty dated Jan. 22, 2015 from corresponding International Patent Application No. PCT/US2008/001357.

Zadi et al."c-Jun N-Terminal Kinase 1 is Required for Toll-Like Receptor 1 Gene Expression in Macrophages." Infection and Immunity, Oct. 2007, p. 5027-5034.

Izadi, et al., "Innate immune responses to B. burgdorderi mediated by JNK1 and the cochaperone, methylation 25 controlled DNAJ (MCJ)" Dissertation for Doctor of Philosophy, Department of Veterinary & Animal Sciences, University ofMassachusetts—Amherst, MA, USA, 2011, pp. 1-85.

Jafarlou, et al., "Methods and Compositons for Metabolic Regulation." Journal of Biological Regulators & Homeostatic Agents, 2016: 30: 315-321 (Year: 2016).

Kampinga, H.H. et al., "Guidelines for the nomenclature of the human heat shock proteins", Cell Stress Chaperones, Jan. 2009, vol. 14, pp. 105-111.

Kawakami, K. et al., "Identification and purification of a human immunoglobulin-enhancer-binding protein (NF-KB) hat activates transcription from a human immunodeficiency virus type 1 promoter in vitro", Proc Natl Acad Sci. USA, Jul. 1988, vol. 85, pp. 4700-4704.

Khalil, M., et al., "Heat shock proteins in oncology: diagnostic biomarkers or therapeutic targets?" Biochimica et Biophysica Acta (BBA)—Reviews on Cancer, Dec. 2011, vol. 1816, pp. 89-104.

Klement, G. et al., "Differences in Therapeutic Indexes of Combination Metronomic Chemotherapy and an AVEGFR-2 Antibody in Multidrug-resistant Human Breast Cancer Xenografts", Clinical Cancer Research, Jan. 2002, vol. 8, pp. 221-232.

Kohler, G. et al., "Derivation of specific antibody-producing tissue culture and tumor lines by cell fusion", Eur J. Immunol., Jul. 1976, vol. 6, pp. 511-519.

Koppenol, W.H. et al., "Otto Warburg's contributions to current concepts of cancer metabolism", Nat Rev Cancer, May 2011, vol. 11, pp. 325-337.

Landschulz, W. et al., "The DNA Binding Domain of the Rat Liver Nuclear Protein C/EBP is Bipartite", Science, Mar. 31, 1989, vol. 243, pp. 1681-1688.

Leachman, S. et al., "First-in-human Mutation-targeted siRNA Phase Ib Trial of an Inherited Skin Disorder", American Society of Gene & Cell Therapy, Feb. 2010, vol. 18, pp. 442-446.

Lee, D., et al., "Involvement of the Molecular Chaperone Ydj1 in the Ubiquitin-Dependent Degradation of Short-Lived ! ind Abnormal Proteins in *Saccharomyces cerevisiae*", Molecular Cell Biology, Sep. 1996, vol. 16, pp. 17.

Lee, W. et al., "Purified Transcription Factor AP-1 Interacts with TPA-Inducible Enhancer Elements" Cell, Jun. 19, 1987, vol. 49, pp. 741-752.

Levine, A.J., and Puzio-Kuter, A.M., "The control of the metabolic switch in cancers by oncogenes and tumor suppressor genes", Science, Dec. 2010, vol. 330, pp. 1340-1344.

Lindsey, J. et al., "Epigenetic inactivation of MCJ (DNAJD1) in malignant paediatric brain tumors", Int. J.Cancer, Jan. 15, 2006, vol. 118, pp. 346-352.

Lingzhou, J., et al., "Advances in Research on Targeting Tumor Therapy with Mitochondria", Anhui Medical and Pharmaceutical Journal, Nov. 2011, vol. 15, 7 pages.

Lo, J.F. et al., "Tid1, a cochaperone of the heat shock 70 protein and the mammalian counterpart of the *Drosophila* tumor suppressor l(2)tid, is critical for early embryonic development and cell survival", Mol Cell Biol, Mar. 2004, vol. 24, pp. 2226-2236.

Longley, D.B., et al., "Molecular mechanisms of drug resistance" Journal of Pathology, Jan. 2005, vol. 205, pp. 275-292.

Maccallum, R et al, "Antibody-antigen Interactions: Contact Analysis and Binding Site Topography", Journal of Molecular Biology, Oct. 11, 1996, vol. 262, pp. 732-745.

Maines, T.R et al., "Transmission and pathogenesis of swine-origin 2009 A(H1N1) influenza viruses in ferrets and mice", Science, Jul. 2009, vol. 325, pp. 484-487.

Mariuzza, RA et al., "The Structural Basis of Antigen-Antibody Recognition", Annu. Rev. Biophys., Biophys. Chem. 1987, vol. 16, pp. 139-159.

McKenzie, M. and Ryan, M.T., "Assembly factors of human mitochondrial complex I and their defects in disease", UBMB Life, Jul. 2010, vol. 62, pp. 497-502.

Mechetner, E. et al., "Levels of Multidrug Resistance (MDR1) P-Glycoprotein Expression by Human Breast Cancer Correlate with in Vitro Resistance to Tazol and Doxorubicin", Clinical Cancer Research, Feb. 1998, vol. 4, pp. 389-398.

Mello et al., "Revealing the world of RNA interference." Nature Publishing Group, Sep. 16, 2004, vol. 431, pp. 338-342.

Mitra, A et al., "Multi-faceted role of HSP40 in cancer", Clin Exp Metastasis, 2009, vol. 26, pp. 559-567.

Mokranjac, D. et al., "The import motor of the yeast mitochondrial TIM23 preprotein translocase contains two different J proteins, Tim14 and Mdj2", J Biol Chem, Sep. 2005, vol. 280, pp. 31608-31614.

Mokranjac, D. et al., "Tim14, a novel key component of the import motor of the TIM23 protein translocase of mitochondria", EMBO Journal, Oct. 1, 2003, vol. 22, pp. 4945-4956.

Musti, A. et al., "Differential Regulation of c-Jun and Juno by Ubiquitin-Dependent Protein Degradation", Biol Chem., Oct. 1996, vol. 377, pp. 619-624.

Nabhan, J. et al., "The 19 S Proteasomal Subunit POH1 Contributes to the Regulation of c-Jun Ubiquitination, Stability, and Subcellular Localization", Journal of Biological Chemistry, Jun. 9, 2006, vol. 281, pp. 16099-16107.

Nambudiri, V. E., et al. :Small Interfering RNA. Journal of Investigative Dermatology, 2013; 133: e15. doi:10.1038/id.2013.411. (Year: 2013).

Nateri, A. et al., "The Ubiquitin Ligase SCFFbw7 Antagonizes Apoptotic JNK Signaling", Science, Feb. 27, 2004, vol. 303, pp. 1374-1378.

Navasa et al., "Regulation of Oxidative Stress by Methylation-Controlled J Protein Controls Macrophage Responses to Inflammatory Insults." The Journal of Infectious Diseases (2014), pp. 1-11.

(56) References Cited

OTHER PUBLICATIONS

Negro, Francesco, "Mechanisms and significance of liver steatosis in hepatitis C virus infection", World Journal of Gastroenterology, Nov. 14, 2006, vol. 12, pp. 6756-6765.

Noonan, K.E. et al., "Quantitative analysis of MDR1 (multidrug resistance) gene expression in human tumors by Dloymerase chain reaction", Proc Natl Acad Sci. USA, Sep. 1990, vol. 87, pp. 7160-7164.

Office Action received in U.S. Appl. No. 12/449,265 dated Jan. 5, 2012.

Ohnishi, T. et al., "Structure-function studies of iron-sulfur clusters and semiquinones in the NADH-Q oxidoreductase segment of the respiratory chain", Biochim Biophys Acta, Jun. 1998, vol. 1365, pp. 301-308.

Olson et al., "p38 Mitogen-Activated Protein Kinase Controls NF-B Transcriptional Activation and Tumor Necrosis 5 Factor Alpha Production through RelA Phosphorylation Mediated by Mitogen- and Stress-Activated Protein Kinase 1 in Response to Borrelia burgdorferi Antigens." Infection and Immunity, Jan. 2007, pp. 270-277.

Orthwein, A. et al., "Optimal functional levels of activation-induced deaminase specifically require the Hsp40 DnaJa1", EMBO J, Feb. 2012, vol. 31, pp. 679-691.

Phillips, A., J. "The challenge of gene therapy and DNA delivery." Journal of Pharmacy and Pharmacology, 2001, 53: 1169-1174.

Pirollo et al., "Targeted Delivery of Small Interfering RNA: Approaching Effective Cancer Therapies." Cancer Res. 2008; 68(5): 1247-1250.

Plavinskaya, T. et al., "Effects of acute and chronic low density lipoprotein exposure on neutrophil function", Pulm Pharmacol Ther., Aug. 2013, vol. 26, pp. 405-411.

Quark Pharmaceuticals, "In a Phase 2 Study PF-04523655 (RTP801I-14) Showed Improved Vision Over Standard of Care in Patients with Diabetic Macular Edema at 12 Months", Mar. 18, 2011, 4 pages.

Qui, et al., "The diversity of the DnaJ/Hsp40 family, the crucial partners fro Hsp70 chaperones", Cellular and Molecular Life Sciences, 2006, vol. 63, pp. 2560-2570.

Ramamoorthi et al., "The Lyme disease agent exploits a tick protein to infect the mammalian host." Nature Publishing Group, Jul. 28, 2005, vol. 436, pp. 573-577.

Response to Office Action dated Jan. 5, 2012 received for U.S. Appl. No. 12/449,265, filed Apr. 18, 2012.

Rincon, M. et al., "Interleukin-6, multi-drug resistance protein-1 expression and response to paclitaxel in women with metastatic breast cancer: results of cancer and leukemia group B trial 159806", Breast Cancer Research Treat, Dec. 2006, vol. 100, pp. 301-308.

Rincon, M. et al., "Prostaglandin E2 and the increase of intracellular cAMP inhibit the expression of interleukin 2 receptors in human T cells", Eur. J. Immunol, Nov. 1988, vol. 18, pp. 1791-1796.

Rudikoff, S. et al., "Single amino acid substitution altering antigen-binding specificity", Proc. Natl. Acad. Sci. USA, Mar. 1982, vol. 79, pp. 1979-1983.

Saibara, T. et al., "Acute hepatic failure with swollen mitochondria and microvesicular fatty degeneration of hepatocytes triggered by free radical initiator", Lab Invest, Apr. 1994, vol. 70, pp. 517-524. (Abstract only, 1 page).

Salceda, S. et al., "Hypoxia-inducible Factor 1alpha (HIF-1a) Protein is Rapidly Degraded by the Ubiquitin-Proteasome System under Normoxic Conditions. Its stabilization by hypoxia depends on redox-induced changes", Journal of Biological Chemistry, Sep. 5, 1997, vol. 272, pp. 22642-22647.

Saraswathi, V. et al., "Dietary Fish Oil Exerts Hypolipidemic Effects in Lean and Insulin Sensitizing Effects in Obese e-DLR-/-Mice1-3", The Journal of Nutrition, Oct. 2009, pp. 2380-2386.

Scheufler, C. et al., "Structure of TPR Domain-Peptide Complexes: Critical Elements in the Assembly of the Hsp70-Hsp90 Multichaperone Machine", Cell, Apr. 14, 2000, vol. 101, pp. 199-210.

Schusdziarra, C. et al., "Methylation-controlled J-protein MCJ acts in the import of proteins into human mitochondria," Human Molecular Genetics, 2013, vol. 22, pp. 1348-1357.

Scotto K., "Transcriptional regulation of ABC drug transporters", Oncogene, Oct. 20, 2003, vol. 22, pp. 17496-17511.

Shridhar, V. et al., "Loss of Expression of a New Member of the DNAJ Protein Family Confers Resistance to Chemotherapeutic Agents Used in the Treatment of Ovarian Cancer", Cancer Research, May 2001, vol. 15, pp. 1258-1265.

Sladowski, D. et al., "An improved MTT assay", Journal of Immunological Methods, Jan. 4, 1993, vol. 157, pp. 203-207.

Smith et al., "Cross-Species Interferon Signaling Boosts Microbicidal Activity within the Tick Vector." Cell Host & Microbe, (2016), 20, pp. 91-98.

Sondermann, H. et al., "Structure of a Bag/Hsc70 Complex: Convergent Functional Evolution of Hsp70 Nucleotide Exchange Factors", Science, Feb. 23, 2001, vol. 291, pp. 1553-1557.

Sozio, MS. et al., "The role of lipid metabolism in the pathogenesis of alcoholic and nonalcoholic hepatic steatosis", Semin Liver dis. Nov. 2010, vol. 30, pp. 378-390. (Abstract only, 1 page).

Sterrenberg, J.N. et al., "Human DNAJ in cancer and stem cells", Cancer Lett, Dec. 2011, vol. 312, pp. 129-142.

Strathdee, G. et al., "Cell type-specific methylation of an intronic CpG island controls expression of the MCJ gene", Carcinogenesis, May 2004, vol. 25, pp. 693-701.

Strathdee. G. et al., "Demethylation of the MCJ gene in stage III/IV epithelial ovarian cancer and response to chemotherapy", Gynecologic Oncology, Jun. 2005, vol. 97, pp. 893-903.

Tabernero, et al., "First-in-Humans Trial of an RNA Interference Therapeutic Targeting VEGF and KSP in Cancer Patients with Liver Involvement." Cancer Discov. 2013; 3, 406-417 (Year: 2013).

Terada, K. et al., "A type I DnaJ homolog, DjA 1, regulates androgen receptor signaling and spermatogenesis", EMBO J, Feb. 2005, vol. 24, pp. 611-622.

Teratani, T . et al., "A high-cholesterol diet exacerbates liver fibrosis in mice via accumulation of free cholesterol in hepatic stellate cells", Gastroenterology, Jan. 2012, vol. 142, pp. 152-164.

Thimme, et al., "CD8 T Cells Mediate Viral Clearance and Disease Pathogenesis during Acute Hepatitis B Virus Infection." Journal of Virology, 2003; 77: 68-76 (Year: 2003).

Treier, M. et al., "Ubiquitin-Dependent c-Jun Degradation in Vivo is Mediated by the I:i Domain", Cell, Sep. 9, 1994, vol. 78, pp. 787-798.

Ungewickell, E. et al., "Role of auxilin in uncoating clathrin-coated vesicles", Nature, Dec. 7, 1995, vol. 378, pp. 632-635.

Vajdos, F. et al., "Comprehensive Functional Maps of the Antigen-binding Site of an Anti-ErbB2 Antibody Obtained With Shotgun Scanning Mutagenesis", Journal of Molecular Biology, Jul. 5, 2002, vol. 320, pp. 415-428.

Van Der Windt, G.J. et al., "Mitochondrial respiratory capacity is a critical regulator of COB+ T cell memory development", Immunity, Jan. 2012, vol. 36, pp. 68-78.

Vidal et al., "Making sense of antisense." European Journal of Cancer, 2005; 41: 2812-2818.

Wahl, R. et al., "Improved Radioimaging and Tumor Localization with Monoclonal F(ab')2", Journal of Nuclear Medicine., Apr. 1983, vol. 24, pp. 316-325.

Walsh, P. et al., "The J-protein family: modulating protein assembly, disassembly and translocation", EMBO Rep, . Jun. 2004, vol. 5, pp. 567-571.

Wang et al., "The brown fat-enriched secreted factor Nrg4 preserves metabolic homeostasis through attenuation of hepatic lipogenesis." Nature Medicine, 2014; 20: 1436-1445.

Wang, et al., "Multiple Paths for Activation of Naive CD8+ T Cells: CD4-Independent Help." The Journal of Immunology, 2001, 167: 1283-1289 (Year: 2001).

Warburg, J., "On Respiratory Impairment in Cancer Cells", Science, Aug. 10, 1956, vol. 124, pp. 267-272.

Watts, J. and D Corey, "Silencing disease genes in the laboratory and the clinic", Journal of Pathology, 2012, vol. 226, pp. 365-379.

Winkler, Ket al., "Changing the Antigen Binding Specificity by Single Point Mutations of an Anti-p24 (HIV-1) Antibody" Journal of Immunology, Oct. 15, 2000, vol. 165, pp. 4505-4514.

(56) References Cited

OTHER PUBLICATIONS

Winkler, J. "Oligonucleotide conjugates for therapeutic applications." Ther. Deliv. 2013; 4: 791-809 (Year: 2013).
Written Opinion of the International Searching Authority dated Aug. 2, 2009 for corresponding International Patent Application No. PCT/US2008/001357.
Wu, H et al., "Humanization of a Murine Monoclonal Antibody by Simultaneous Optimization of Framework and CDR Residues" J. Mol. Biol., Nov. 19, 1999, vol. 294, pp. 151-162.
Yang, ZX., et al., "Effects of nuclear receptor FXR on the regulation of liver lipid metabolism in patients with non-alcoholic fatty liver disease", Hepatol Int, 2010, vol. 4, pp. 741-748.
Yin, et al., "Silencing heat shock factor 1 by small interfering RNA abrogates heat shock-induced cardioprotectin against ischemia-reperfusion injury in mice." Journal of Molecular and Cellular Cardiology, 2005; 39: 681-689. (Year: 2005).
Addya, S. et al., "Targeting of NH2-terminal-processed Microsomal Protein to Mitochondria: A Novel Pathway for the S,iogenesis of Hepatic Mitochondrial P450MT2", The Journal of Cell Biology, Nov. 3, 1997, vol. 139, pp. 589-599.
Affidavit Regarding Deposited Microorganism Pursuant to 37 C.F.R 1.808 filed in U.S. Appl. No. 12/449,265, filed Apr. 18, 2012.
Ahn, BY. et al., "Tid1 is a new regulator of p53 mitochondrial translocation and apoptosis in cancer", Oncogene, Feb. 2010, vol. 29, pp. 1155-1166.
Alley, M., et al., "Feasibility of Drug Screening with Panels of Human Tumor Cell Lines Using a Micoculture Wetrazolium Assay", Cancer Research, Feb. 1, 1988, vol. 48, pp. 589-601.
Angel, P., et al., "Phorbol Ester-Inducible Genes Contain a Common Cis Element Recongized by a TPA-Modulated Wrans-Acting Factor" Cell, Jun. 19, 1987, vol. 49, pp. 729-739.
Araki, K. et al., "mTOR regulates memory CD8 T cell differentiation", Nature, Jul. 2009, vol. 460, pp. 108-112.
Auphan, N. et al., "Consequences of intrathymic TCR engagement by partial agonist on selection events and peripheral T cell activation program", J. Immunol, May 1998, vol. 160, pp. 4810-4821.
Baerga-Ortiz, A et al, "Epitope mapping of a monoclonal antibody against human thrombin by HID-exchange mass sepctometry reveals selection of a diverse sequence in a highly conserved protein", Protein Science, Jun. 2002, vol. 11, pp. 1300-1308.
Bird, R et al, "Single-Chain Antigen-Binding Proteins", Science, Oct. 21, 1988, vol. 242, pp. 423-426.
Brummelkamp, T., et al., "A System for Stable Expression of Short Interfering RNAs in Mammalian Cells", Science, Apr. 19, 2002, vol. 296, pp. 550-553.
Cairns, RA. et al., "Regulation of cancer cell metabolism", Nat Rev Cancer, Feb. 2011, vol. 11, pp. 85-95.
Caldas, C., et al., "Humanization of the anti-CD 18 antibody 6.7: an unexpected effect of framework residue in binding to antigen", Molecular Immunology, May 2003, vol. 39, pp. 941-952.
Campbell, A., Monoclonal Antibody Technology, Laboratory Techniques in Biochemistry and Molecular Biology, 1984, Elsevier Science Publishers BV: Amsterdam, The Netherlands vol. 13, pp. 1-32, Chapter 1: General Properties iind Applications of Monoclonal Antibodies.
Casset, F., et al., "A peptide mimetic of an anti-CD4 monoclonal antibody by rational design", Biochemical and Biophysical Research Communication, Jul. 18, 2003, vol. 307, pp. 198-205.
Chen, Y. et al., "Characterization of Adriamycin-resistant Human Breast Cancer Cells Which Display Overexpression of a Novel Resistance-related Membrane Protein", Journal of Biological Chemistry, Jun. 15, 1990, vol. 265, pp. 10073-10080.
Chen, Y. et al., "In Situ Biochemical Demonstration that P-Glycoprotein is a Drug Efflux Pump with Broad Specificity", Uournal of Cellular Biology, Mar. 6, 2000, vol. 148, pp. 863-870.
Chien, N. et al., "Significant structural and functional change of an antigen-binding site by a distant amino acid substitution: Proposal of a structural mechanism", Proc. Natl. Acad. Sci., USA, Jul. 1989, vol. 86, pp. 5532-5536.

Clason, T. et al., "The structure of eukaryotic and prokaryotic complex I", J Struct Biol, Jan. 2010, vol. 169, pp. 81-88.
Comerford , K.et al., "Hypoxia-inducible Factor-1-dependent Regulation of the Multidrug Resistance (MDR1) Gene", Cancer Research, Jun. 15, 2002, vol. 62, pp. 3387-3394.
Conze et al., "Autocrine p\Production of Interleukin 6 Causes Multidrug Resistance in Breast Cancer Cells", Cancer Research, Dec. 15, 2001, vol. 61, pp. 8851-8858.
Conze, D. et al., "c-Jun NH(2)-terminal kinase (JNK)1 and JNK2 have distinct roles in COB(+) T cell activation", J. Exp.Med, Apr. 2002, vol. 195, pp. 811-823.
Craig, EA et al., "The diverse roles of J-proteins, the obligate Hsp70 co-chaperone", Rev Physiol Biochem Pharmacol., 2006, vol. 156, pp. 1-21.
Czauderna et al., "Structural variations and stabilising modifications of synthetic siRNAs in mammalian cells." Nucleic Acids Research, 2003, vol. 31, No. 11, 2705-2716.
Da Cruz, S. et al., "Proteomic analysis of the mouse liver mitochondrial inner membrane", J. Biol. Chem., Oct. 2003, vol. 278, pp. 41566-41571.
De Pascalis, R. et al., "Grafting of "Abbreviated" Complementary-Determining Regions Containing Specificity-Determining Residues Essential for Ligand Contact to Engineer a Less Immunogenic Humanized Monoclonal Antibody", Journal of Immunology, 2002, vol. 169, pp. 3076-3084.
Del Gaizo, V. et al., "Targeting proteins to mitochondria using TAT", Molecular Genetics and Metabolism, 2003, vol. 80, pp. 170-180.
Derijard, B. et al., "JNK1: A Protein Kinase Stimulated by UV Light and Ha-Ras That Binds and Phosphorylates the c-Jun Activation Domain", Cell., Mar. 25, 1994, vol. 76, pp. 1025-1037.
Devincenzo, et al., "A randomized, double-blind, placebo-controlled study of an RNAi-based therapy directed against respiratory syncytial virus", PNAS, May 11, 2010, vol. 107, pp. 8800-8805.
Diah, S., et al., "Resistance to Mitoxantrone in Multidrug-resistant MCF7 Breast Cancer Cells: Evaluation Mitoxantrone Transport and the Role of Multidrug Resistance Protein Family Proteins", Cancer Research, Jul. 15, 2001, vol. 61, pp. 5461-5467.
Diekert, K. et al., "An internal targeting signal directing proteins into the mitochondrial intermembrane space", PNAS Oct. 12, 1999, vol. 96, pp. 11752-11757.
Doyle, L. et al., "Multidrug resistance mediated by the breast cancer resistance protein BCRP (ABCG2)", Oncogene, Oct. 20, 2003, vol. 22, pp. 7340-7358.
Dpykxhoorn, D.M. et al., "The silent treatment: siRNAs as small molecule drugs", Gene Therapy, 2006, vol. 13, pp. 541-552.
Ehrlich, M. et al., "Hypomethylation and hypermethylation of DNA in Wilms tumors", Oncogene, Sep. 26, 2002, vol. 21, pp. 6694-6702.
Fairchild, C. et al., "Isolation of Amplified and Overexpressed DNA Sequences from Adriamycin-resistant Human Breast Cancer Cells", Cancer Research, Oct. 1, 1987, vol. 47, pp. 5141-5148.
Fairchild, C., et al., "Multidrug Resistance in Cells Transfected with Human Genes Encoding a Variant P-Glycoprotein and Glutathione S-Transferase-n", Molecular Pharmacology, Jun. 1990, vol. 37, pp. 801-809.
Fang, D. et al., "Ubiquitin-mediated fluorescence complementation reveals that Jun ubiquitinated by Itch/AIP4 is ocalized to lysosomes", Proc Natl Acad Csi US A, Oct. 12, 2004, vol. 101, pp. 14782-14787.
Finlay, D and Cantrell, DA., "Metabolism, migration and memory in cytotoxic T cells", Nat Rev Immunol, Feb. 2011, vol. 11, pp. 109-117.
Fuchs, S., et al., "Phosphorylation-dependent targeting of c-Jun ubiquitination by Jun N-kinase", Oncogene, Oct. 8, 1996, vol. 13, pp. 1531-1535.
Gao, M. et al., "Jun Turnover is Controlled Through JNK-Dependent Phosphorylation of the E3 Ligase Itch", Science, Oct. 8, 2004, vol. 306, pp. 271-275.
Garcia-Ruiz, C. et al., "Metabolic therapy: lessons from liver diseases", Curr Pharm Des., Dec. 2011, vol. 17, pp. 3933-3944. (Abstract only, 1 page).

(56) References Cited

OTHER PUBLICATIONS

Genbank Submission; NIH/NCBI, Accession No. AF126743; Shridhar et al.; May 25, 2001, 2 pages.
Genbank Submission; NIH/NCBI, Accession No. MD38506; Shridhar et al.; May 25, 2001, 2 pages.
Genbank Submission; NIH/NCBI, Accession No. NP _037370; Hendrickson et al.; Jul. 29, 2011, 2 pages.
George, J., et al., "Differential Effects of Anti-B-Glycoprotein I Antibodies on Endothelial Cells and on the Manifestations of Experimental Antiphospholipid Syndrome", American Heart Association, 1998, vol. 97, pp. 900-906.
Giusti, A., et al., "Somatic diversification of S107 from an antiphosphocholine to an anti-DNA autoantibody is due to a single base change in its heavy chain variable region", Proc. Natl. Acad. Sci.,USA, May 1987, vol. 84, pp. 2926-2930.
Gottesman, M. et al., "Multidrug Resistance in Cancer: Role of ATP-Dependent Transporters", Nature Reviews Cancer, Jan. 2002, vol. 2, pp. 48-58.
Gussow, D. et al., "Humanization of Monoclonal Antibodies", Methods in Enzymology, 1991, vol. 203, pp. 99-121.
Guy, CT. et al., "Induction of mammary tumors by expression of polyomavirus middle T oncogene: a transgenic mouse model for metastatic disease", Mol Cell Biol, Mar. 1992, vol. 12, pp. 954-961.
Halazonetis, T. et al., "c-Jun Dimerizes with Itself and with c-Fos, Forming Complexes of Different DNA Binding Affinities", Cell, Dec. 2, 1988, vol. 55, pp. 917-924.
Izawa, I. et al., "Identification of Mrj, a DnaJ/Hsp40 Family Protein, as a Keratin 8/18 Filament Regulatory Protein", Uournal of Biological Chemistry, Nov. 3, 2000, vol. 275, pp. 34521-34527.
"Quark Pharmaceuticals Receives FDA Approval of IND for Kidney Transplant siRNA Drug", Fierce Biotech, Jun. 25, 2008, 2 pages.

\* cited by examiner

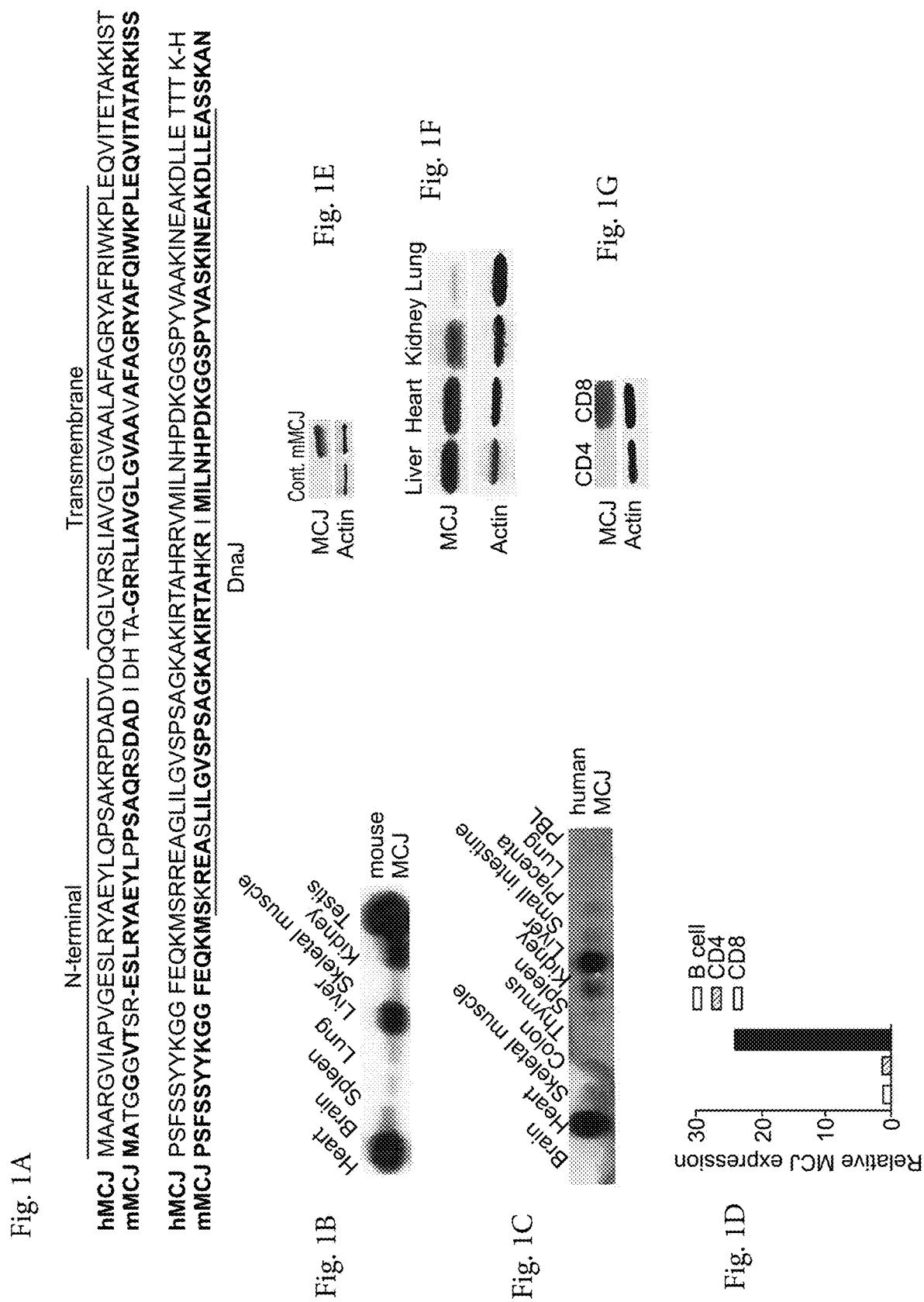

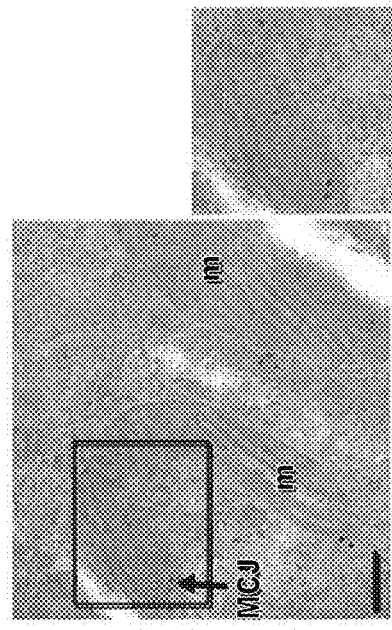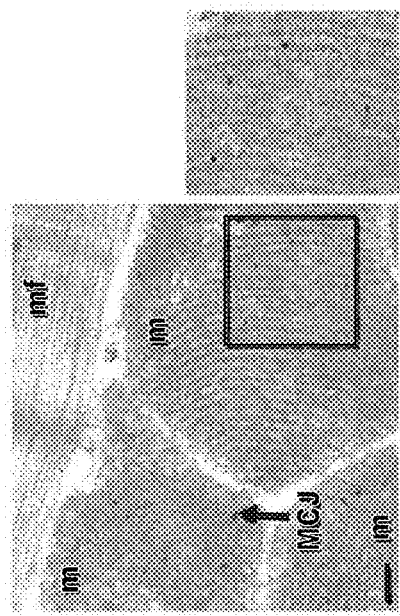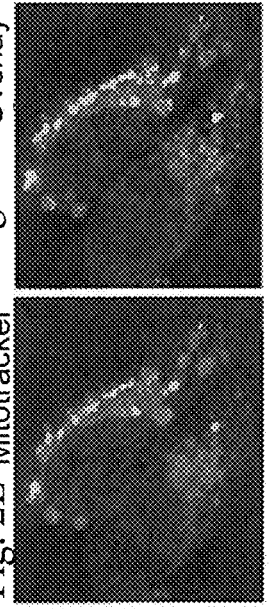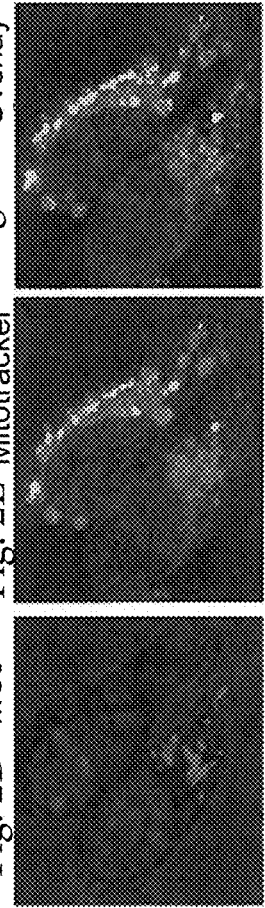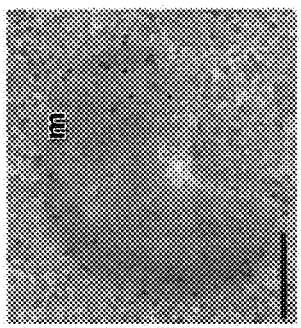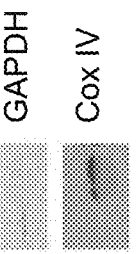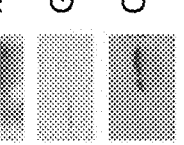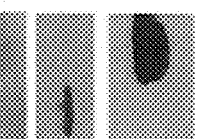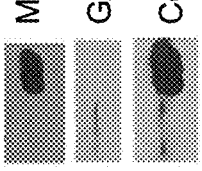

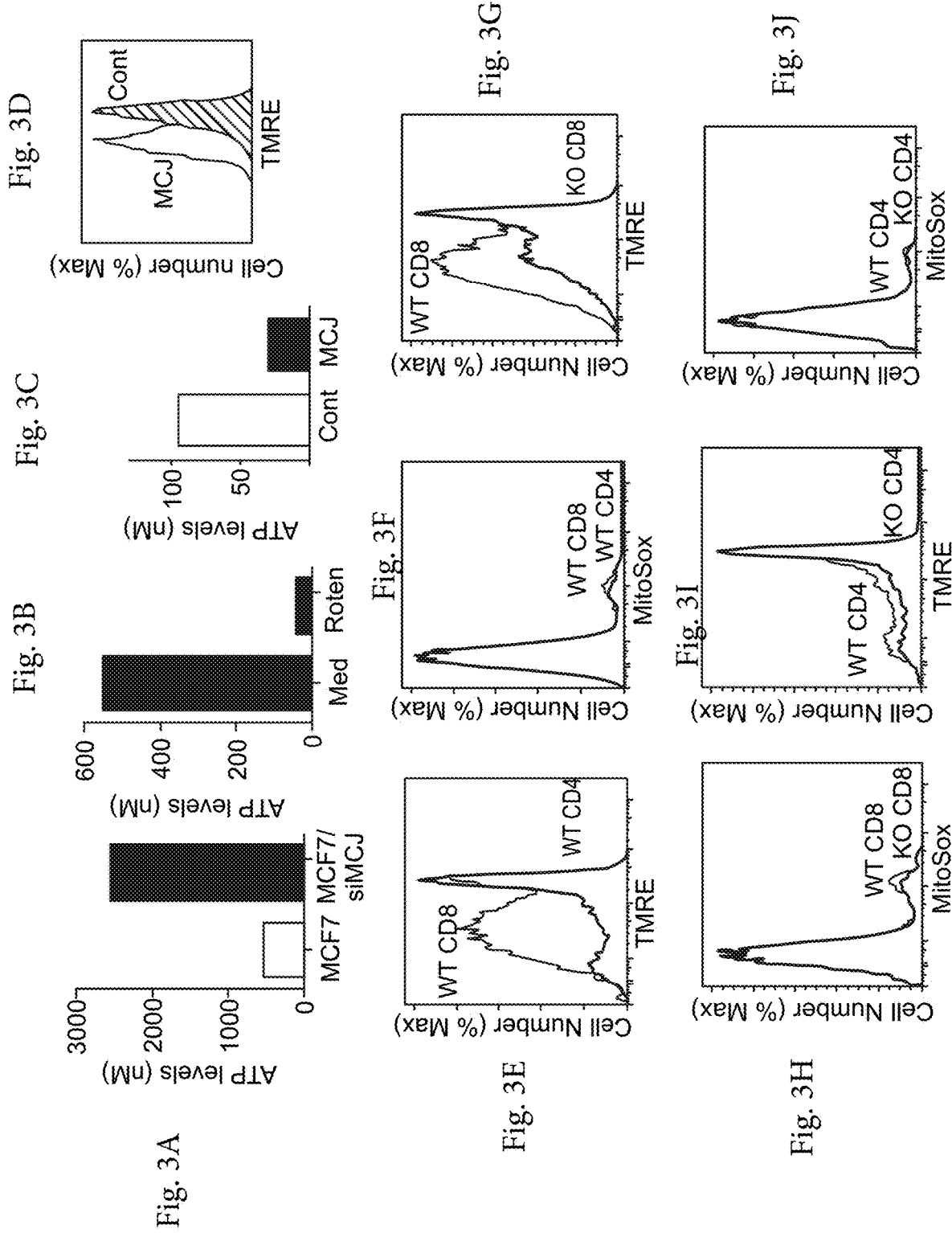

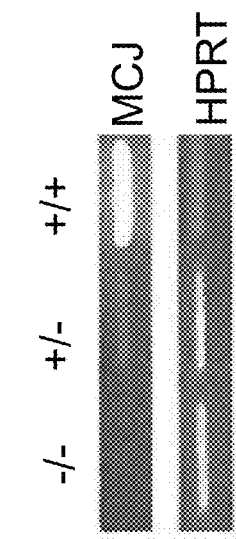
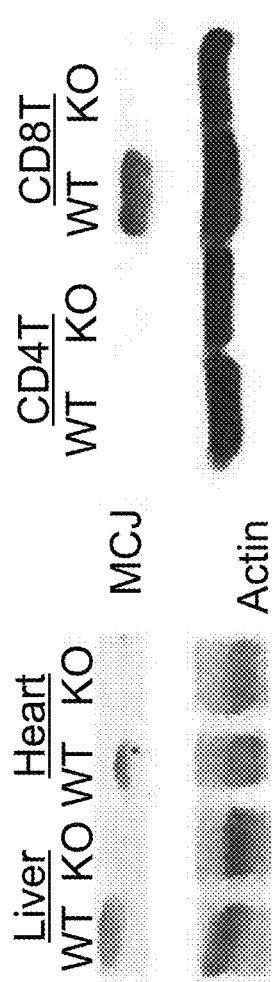
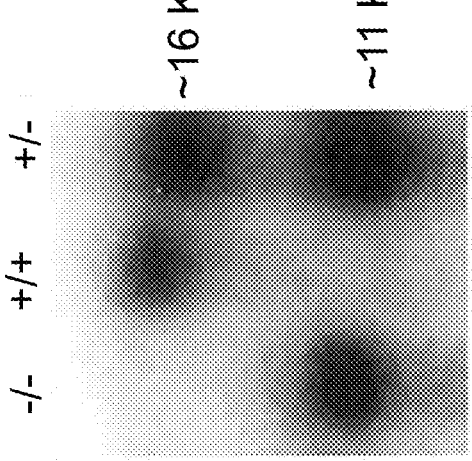
Fig. 4A
Fig. 4B
Fig. 4C

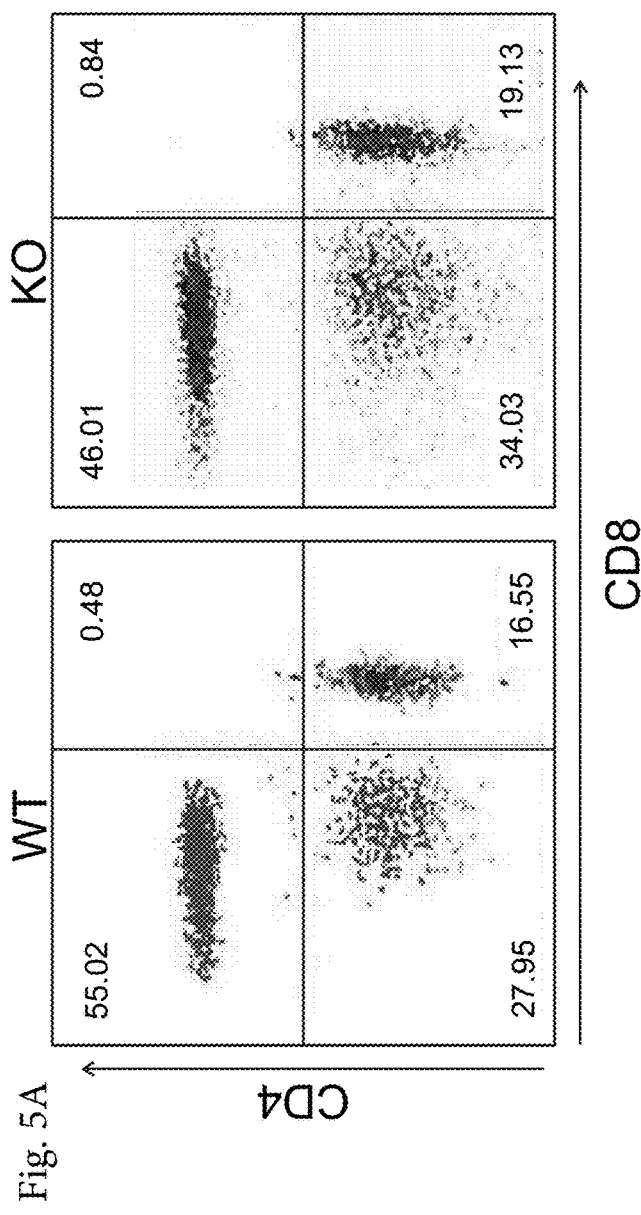
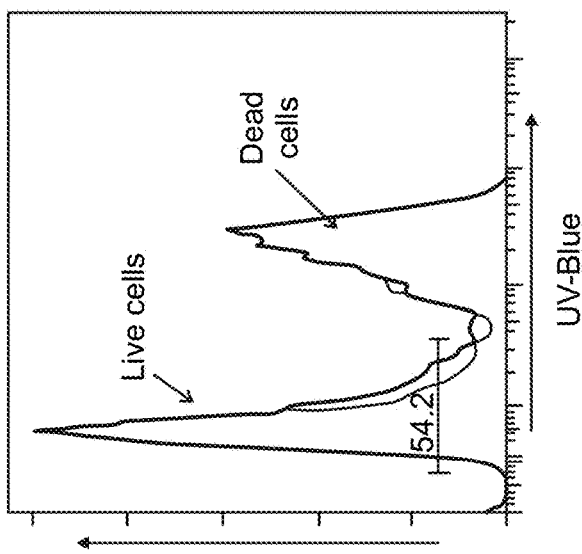
Fig. 5A
Fig. 5B

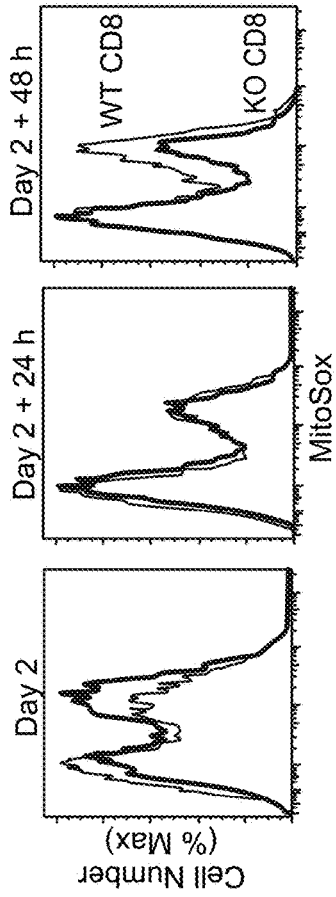
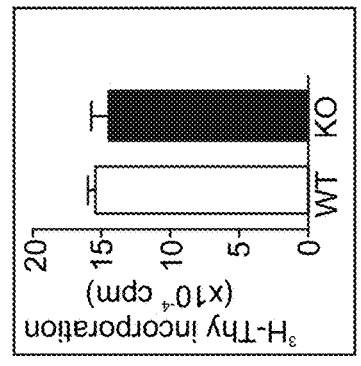
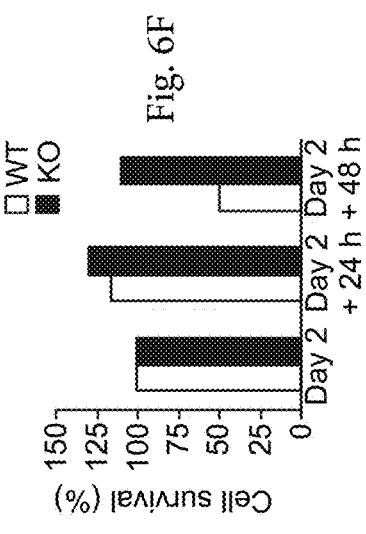
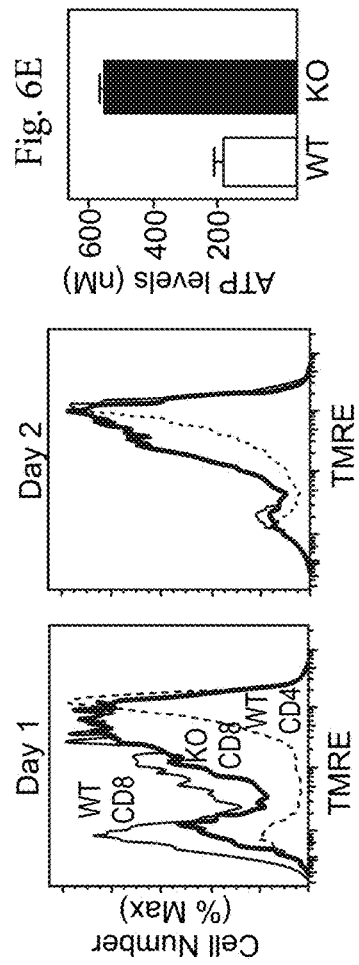
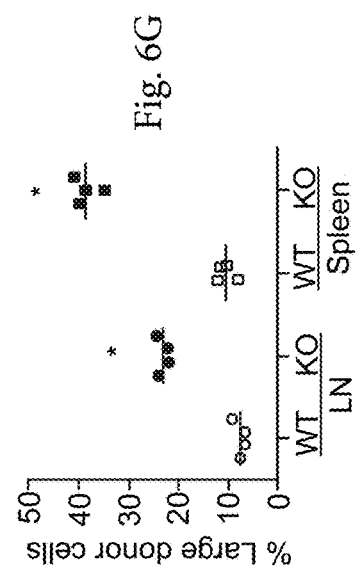
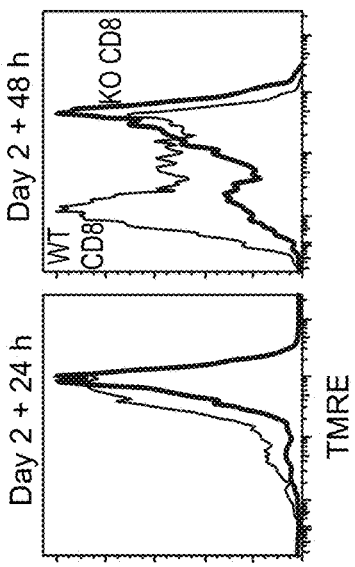
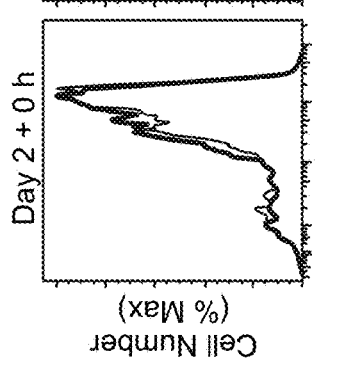

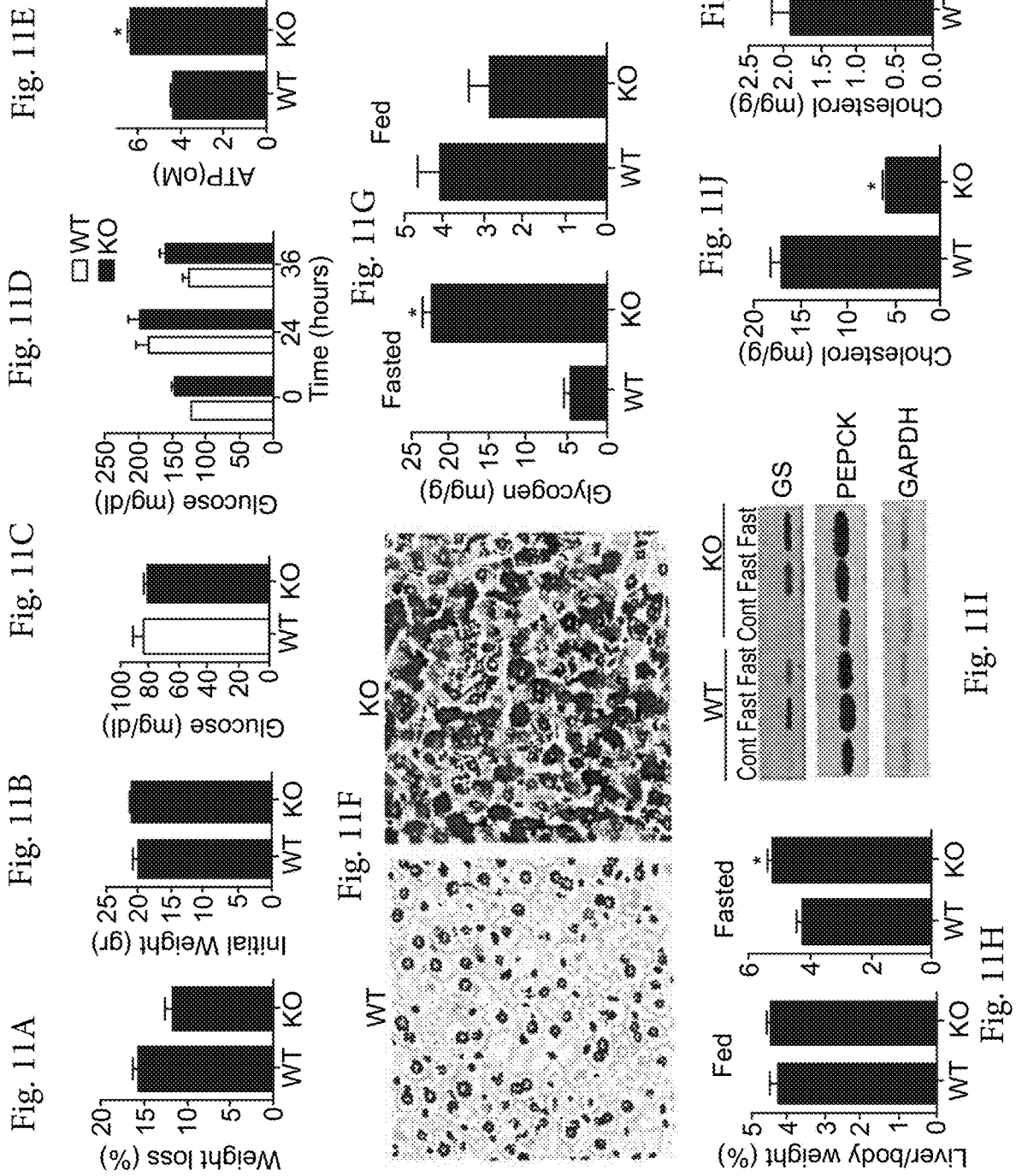

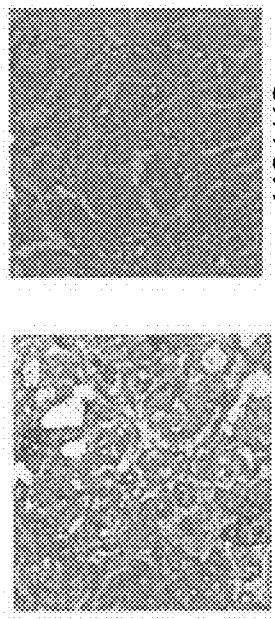
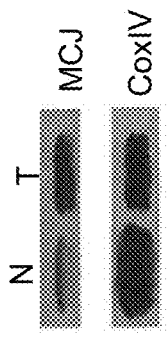
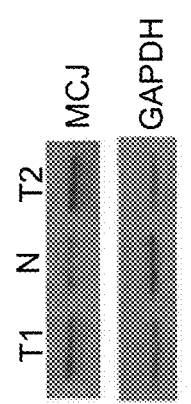
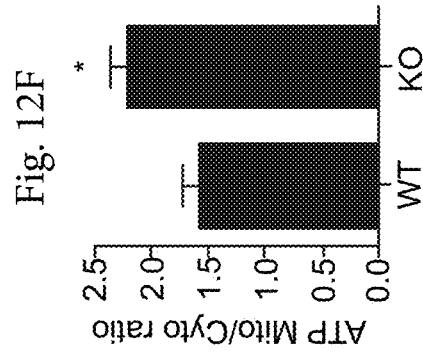
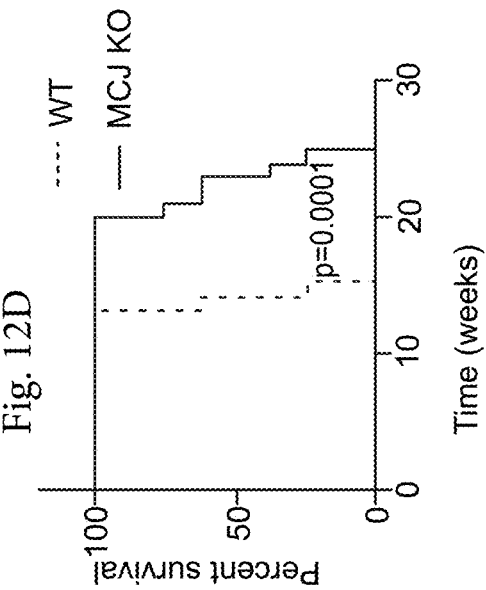
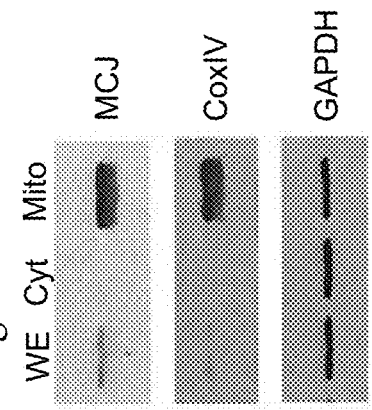

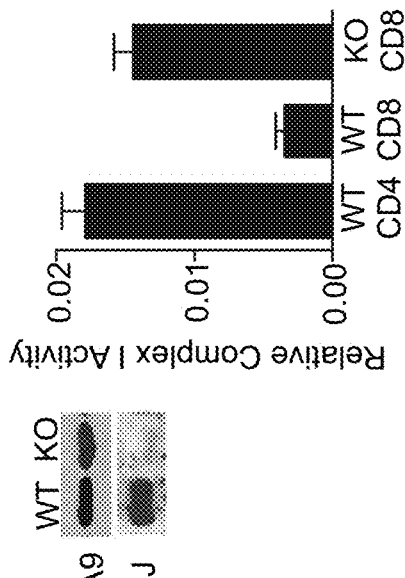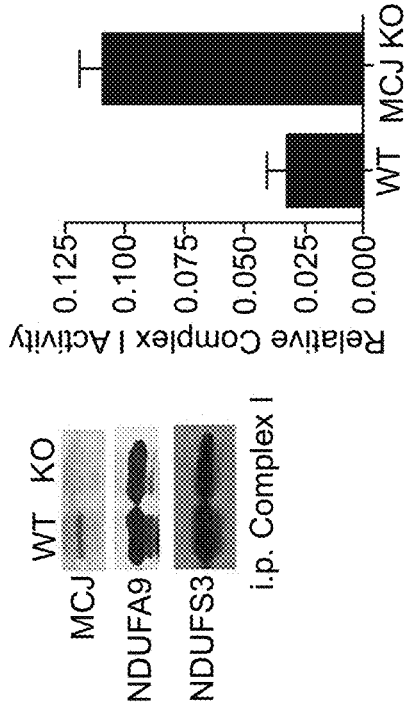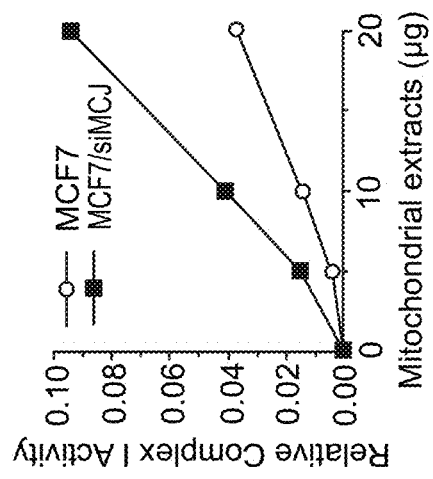

ADMINISTERING METHYLATION-CONTROLLED J PROTEIN (MCJ) SIRNA TO A KIDNEY CELL

RELATED APPLICATIONS

This application is a continuation of U.S. application Ser. No. 15/805,534, filed Nov. 7, 2017, which is a continuation of U.S. application Ser. No. 14/413,927, filed Jan. 9, 2015, which issued Mar. 10, 2020 as U.S. Pat. No. 10,583,169, which is a National Stage Filing under U.S.C. § 371 of PCT International Application PCT/US2013/49885, filed Jul. 10, 2013 which was published under PCT Article 21(2) in English, which claims benefit under 35 U.S.C. § 119(e) of U.S. Provisional Application No. 61/670,345, filed Jul. 11, 2012 and the content of each of which is incorporated by reference herein in its entirety.

GOVERNMENT INTEREST

This invention was made with government support under R21 CA127099 awarded by the National Institutes of Health. The government has certain rights in the invention.

FIELD OF THE INVENTION

The invention relates, in part, to methods and compounds that are useful to regulate metabolic functions.

BACKGROUND

Co-chaperones modulate the activity of chaperones, primarily heat shock proteins (HSPs), either directly or indirectly through the recruitment of other proteins (Walsh et al., 2004, *EMBO Rep* 5, 567-571). Although the regulation and role of chaperones have been extensively studied, little is known about the function of the large number of identified co-chaperones. The DnaJ family of co-chaperones is the largest and the most diverse with 49 identified members in humans. It is characterized by the presence of the highly conserved 70 aa J-domain containing a His-Pro-Asp motif that binds to the ATPase domain of HSP70 family members and promotes their ATPase activity (Walsh et al., 2004, *EMBO Rep* 5, 567-571; Mitra et al., 2009, *Clin Exp Metastasis* 26, 559-567; Sterrenberg et al., 2011, *Cancer Lett* 312, 129-142). The members of this family have been classified in three subfamilies according to the presence and nature of sequences other than the J-domain (DnaJA, DnaJB and DnaJC subfamilies) (Kampinga et al., 2009, *Cell Stress Chaperones* 14, 105-111). The DnaJA subfamily contains a Gly/Phe (G/F) rich region and a Cys repeat region, while the DnaJB subfamily contains the G/F region but lacks the Cys-repeat region. DnaJC subfamily members are highly diverse. They lack both the G/F and Cys-repeat regions, while their J domain can be located at any position in the protein. However, most DnaJC members have less characterized non-classical domains that seem to provide specificity for partner binding and function.

DnaJ co-chaperones can interact with proteins other than HSPs in a DnaJ-domain independent manner to mediate specific functions (Sterrenberg et al., 2011 *Cancer Lett* 312, 129-142). However, only a few targets have been identified. Within the mitochondria, the DNA polymerase gamma (Polga) has been shown to interact with Tid1 (Hayashi et al., 2006 *Nat Med* 12, 128-132), and more recent studies have also identified p53 as another potential target (Ahn et al., 2010 *Oncogene* 29, 1155-1166). DnaJA1 has also been recently found to interact with Adenosin Induced Deaminase (AID) in B cells and modulate its activity during class switching recombination (Orthwein et al., *EMBO J* 2011 Nov. 15; 31(3):679-91). The role of DnaJ co-chaperones in cancer is a functional aspect of these proteins that has begun to be investigated, although primarily in cell lines (Mitra et al., 2009, *Clin Exp Metastasis* 26, 559-567). In addition, only a few orthologs of human DnaJ proteins have been identified in mouse (e.g., DnaJC10/ERdj5, DnaJB6/Mrj and DnaJA3/Tid1, DnaJA1/DjA1) (Terada et al., 2005, *EMBO J* 24, 611-622; Hosoda et al., 2010, *Biochem J* 425, 117-125; Lo et al., 2004, *Mol Cell Biol* 24, 2226-2236; Hunter et al., 1999, *Development* 126, 1247-1258).

The absence of known domains and the presence of poorly characterized non-classical domains have made it difficult to characterize the functions of most DnaJC family members. As a consequence, and despite the large number of DnaJ co-chaperones identified in humans, their function in normal and disease conditions remain mostly unknown.

SUMMARY OF THE INVENTION

According to one aspect of the invention, methods for treating a metabolic disease or condition in a subject are provided. The methods include administering to a subject in need of such treatment an MCJ-modulating compound in an amount effective to treat the metabolic disease or condition in the subject. In some embodiments, the MCJ-modulating compound decreases an MCJ polypeptide activity in the subject and increases a metabolic activity of a mitochondrion in the subject. In some embodiments, decreasing the MCJ polypeptide activity comprises decreasing an MCJ polypeptide level or function. In some embodiments, the MCJ-modulating compound increases an MCJ polypeptide activity in the subject and decreases a metabolic activity of a mitochondrion in the subject. In some embodiments, increasing the MCJ polypeptide activity comprises increasing an MCJ polypeptide level or function. In certain embodiments, the method also includes reducing a level of caloric intake of the subject. In some embodiments, the level of caloric intake is reduced prior to, concurrent with, and/or after administration of the MCJ-modulating compound to the subject. In some embodiments, the metabolic disease or condition is overweight, weight gain, obesity, non-alcoholic fatty liver disease, diabetes, insulin-resistance, alcoholic fatty liver disease, dyslipidemia, steatosis (e.g., liver steatosis, heart steatosis, kidney steatosis, muscle steatosis), abetalipoproteinemia, glycogen storage disease, Weber-Christian disease, lipodystrophy; a liver disease, liver inflammation, hepatitis, steatohepatitis, Hepatitis C, Genotype 3 Hepatitis C, Alpha 1-antitrypsin deficiency, acute fatty liver of pregnancy, Wilson disease; a kidney disease; a heart disease, hypertension, ischemia, heart failure, cardiomyopathy; poisoning; HIV; a neurodegenerative disease, Parkinson's disease, Alzheimer's disease; cancer, or physical exercise. In some embodiments of the invention, the metabolic disease or condition is high cholesterol and reducing MCJ activity may be used in methods to reduce cholesterol in a cell, tissue, or subject. In certain embodiments, the metabolic disease or condition is an eating disorder, anorexia, starvation, malnutrition, total parenteral nutrition, severe weight loss, underweight, re-feeding syndrome; gastrointestinal surgery-mediated metabolic alterations, jejuno-ilial bypass, gastric bypass; and inflammatory/infectious conditions, jujunal diverticulosis with bacterial overgrowth, and inflammatory bowel disease. In some embodiments, the subject is a fasting subject. In some embodiments, treating the metabolic disease or condition comprises enhancing or inhibiting cytotoxic T cell activity. In some embodiments, the MCJ-modulating compound is administered in a pharmaceutical composition. In certain embodiments, the pharmaceutical composition further comprises a pharmaceutically acceptable carrier. In some embodiments, the pharmaceutical composition further comprises a targeting agent. In some embodiments, the targeting agent is a mitochondrial targeting agent. In some embodiments, the MCJ-modulating compound comprises an MCJ molecule, an anti-MCJ polypeptide antibody or functional fragment thereof, a small molecule MCJ inhibitor, or a small molecule MCJ enhancer. In certain embodiments, the MCJ molecule is an MCJ polypeptide or a nucleic acid that encodes an MCJ polypeptide. In some embodiments, the subject does not have cancer. In some embodiments, the metabolic disease or condition is not cancer. In certain embodiments, the method also includes increasing a level of caloric intake of the subject. In some embodiments, the level of caloric intake is increased prior to, concurrent with, and/or after administration of the MCJ-modulating compound to the subject.

According to another aspect of the invention, methods of altering mitochondrial metabolism in a cell are provided. The methods include contacting the cell with an exogenous MCJ-modulating compound in an amount effective to alter mitochondrial metabolism in the cell, wherein an MCJ-modulating compound that increases MCJ polypeptide activity decreases mitochondrial metabolism in the cell and an MCJ-modulating compound that decreases MCJ polypeptide activity increases mitochondrial metabolism in the cell. In some embodiments, increasing the MCJ polypeptide activity includes increasing a level or function of MCJ polypeptide in the cell. In certain embodiments, decreasing the MCJ polypeptide activity includes decreasing a level or function of MCJ polypeptide in the cell. In some embodiments, mitochondrial metabolism includes mitochondrial respiration. In some embodiments, the cell is in vitro. In some embodiments, the cell is in vivo. In certain embodiments, the cell is in a subject and the contacting includes administering the MCJ-modulating compound to the subject. In some embodiments, the subject is a fasting subject. In some embodiments, the subject is a subject with an increased level of caloric intake. In certain embodiments, the MCJ-modulating compound is administered in a pharmaceutical composition. In some embodiments, the pharmaceutical composition also includes a pharmaceutically acceptable carrier. In some embodiments, the pharmaceutical composition further comprises a targeting agent. In some embodiments, the targeting agent is a mitochondrial targeting agent. In certain embodiments, the MCJ-modulating compound includes an MCJ molecule, an anti-MCJ polypeptide antibody or functional fragment thereof, a small molecule MCJ inhibitor, or a small molecule MCJ enhancer. In some embodiments, the MCJ molecule is an MCJ polypeptide or a nucleic acid that encodes an MCJ polypeptide. In some embodiments, the MCJ-modulating compound includes a mitochondrial targeting agent. In certain embodiments, the subject has a metabolic disease or condition. In some embodiments, the metabolic disease or condition is overweight, weight gain, obesity, non-alcoholic fatty liver disease, diabetes, insulin-resistance, alcoholic fatty liver disease, dyslipidemia, steatosis (e.g., liver steatosis, heart steatosis, kidney steatosis, muscle steatosis), abeta-lipoproteinemia, glycogen storage disease, Weber-Christian disease, lipodystrophy; a liver disease, liver inflammation, hepatitis, steatohepatitis, Hepatitis C, Genotype 3 Hepatitis C, Alpha 1-antitrypsin deficiency, acute fatty liver of pregnancy, Wilson disease; a kidney disease; a heart disease, hypertension, ischemia, heart failure, cardiomyopathy; poisoning; HIV; a neurodegenerative disease, Parkinson's disease, Alzheimer's disease; cancer, or physical exercise. In some embodiments of the invention, the metabolic disease or condition is high cholesterol and reducing MCJ activity may be used in methods to reduce cholesterol in a cell, tissue, or subject. In some embodiments, the metabolic disease or condition is an eating disorder, anorexia, starvation, malnutrition, total parenteral nutrition, severe weight loss, underweight, re-feeding syndrome; gastrointestinal surgery-mediated metabolic alterations, jejuno-ilial bypass, gastric bypass; an inflammatory/infectious condition, jujunal diverticulosis with bacterial overgrowth, or inflammatory bowel disease. In certain embodiments, the subject does not have cancer. In some embodiments, the metabolic disease or condition is not cancer.

According to another aspect of the invention, methods of modulating cytotoxic T (CD8$^+$ T) cell function in a subject are provided. The methods include administering to a subject in need of such treatment an MCJ-modulating compound in an amount effective to increase or decrease an activity of an MCJ polypeptide in a CD8$^+$ T cell, wherein an increase in MCJ polypeptide activity increases depolarization of a mitochondrion in the CD8$^+$ T cell and a decrease in MCJ polypeptide activity decreases depolarization of a mitochondrion in the CD8$^+$ T cell, and wherein the increase or decrease in depolarization of the mitochondrion modulates cytotoxic T cell function in the subject. In some embodiments, increasing the activity of the MCJ polypeptide includes increasing the level or function of the MCJ polypeptide in the cell. In certain embodiments, decreasing the activity of the MCJ polypeptide includes decreasing the level or function of the MCJ polypeptide in the cell. In some embodiments, the MCJ-modulating compound is administered in a pharmaceutical composition. In some embodiments, the pharmaceutical composition also includes a pharmaceutically acceptable carrier. In certain embodiments, the pharmaceutical composition also includes a targeting agent. In some embodiments, the targeting agent is a mitochondrial targeting agent. In some embodiments, the MCJ-modulating compound includes an MCJ molecule, an anti-MCJ polypeptide antibody or functional fragment thereof, a small molecule MCJ inhibitor, or a small molecule MCJ enhancer. In some embodiments, the MCJ molecule is an MCJ polypeptide or a nucleic acid that encodes an MCJ polypeptide. In certain embodiments, the subject does not have cancer.

According to another aspect of the invention, compositions that include an MCJ-modulating compound and a pharmaceutically acceptable carrier are provided. In some embodiments, the composition also includes a mitochondrial-targeting agent. In some embodiments, the MCJ-modulating compound includes an MCJ molecule, an anti-MCJ polypeptide antibody or functional fragment thereof, a small molecule MCJ inhibitor, or a small molecule MCJ enhancer. In some embodiments, the MCJ molecule is an MCJ polypeptide or a nucleic acid that encodes an MCJ polypeptide.

According to yet another aspect of the invention, methods of determining the presence or absence of a metabolic disease or condition in a subject are provided. The methods include obtaining a biological sample from a subject; measuring a level of a MCJ molecule in the biological sample; and comparing the measured level with a control level of the MCJ molecule, wherein an altered level of the MCJ molecule in the biological sample compared to the control level indicates the presence or absence of the metabolic disease or condition in the subject. In some embodiments, the MCJ molecule is an MCJ polypeptide or a nucleic acid that encodes an MCJ polypeptide. In certain embodiments, the level of the MCJ molecule in the biological sample is decreased compared to the control level. In some embodiments, the level of the MCJ molecule in the biological sample is increased compared to the control level. In some embodiments, measuring the level of the MCJ molecule includes measuring the amount and/or function of the MCJ molecule. In some embodiments, the method also includes selecting a treatment strategy for the subject based, at least in part, on the determination of the presence of absence of the metabolic disease or condition in the subject. In certain embodiments, the treatment strategy includes administering to the subject a medicament or behavioral treatment for the metabolic disease or condition. In some embodiments, the treatment strategy includes ceasing administration to the subject of a medicament or behavioral treatment for the metabolic disease or condition. In some embodiments, the metabolic disease or condition is overweight, weight gain, obesity, non-alcoholic fatty liver disease, diabetes, insulin-resistance, alcoholic fatty liver disease, dyslipidemia, steatosis (e.g., liver steatosis, heart steatosis, kidney steatosis, muscle steatosis), abeta-lipoproteinemia, glycogen storage disease, Weber-Christian disease, lipodystrophy; a liver disease, liver inflammation, hepatitis, steatohepatitis, Hepatitis C, Genotype 3 Hepatitis C, Alpha 1-antitrypsin deficiency, acute fatty liver of pregnancy, Wilson disease; a kidney disease; a heart disease, hypertension, ischemia, heart failure, cardiomyopathy; poisoning; HIV; a neurodegenerative disease, Parkinson's disease, Alzheimer's disease; cancer, or physical exercise. In some embodiments of the invention, the metabolic disease or condition is high cholesterol. In some embodiments, the metabolic disease or condition is an eating disorder, anorexia, starvation, malnutrition, total parenteral nutrition, severe weight loss, underweight, re-feeding syndrome; gastrointestinal surgery-mediated metabolic alterations, jejuno-ilial bypass, gastric bypass; and inflammatory/infectious conditions, jujunal diverticulosis with bacterial overgrowth, or inflammatory bowel disease. In certain embodiments, the method also includes treating the metabolic disease or condition the presence of which is determined in the subject.

The present invention is not intended to be limited to a system or method that must satisfy one or more of any stated objects or features of the invention. It is also important to note that the present invention is not limited to the exemplary or primary embodiments described herein. Modifications and substitutions by one of ordinary skill in the art are considered to be within the scope of the present invention.

BRIEF DESCRIPTION OF THE SEQUENCES

SEQ ID NO:1 is amino acid sequence of human DNAJ domain-containing protein MCJ set forth as GENBANK® Accession No. AAD38506.1.

SEQ ID NO:2 is mRNA sequence of human DNAJ domain-containing protein MCJ set forth as GENBANK® Accession No. AF126743.1.

SEQ ID NO:3 is amino acid sequence of a mouse DNAJ domain-containing protein.

SEQ ID NO:4 is amino acid sequence of a human DnaJ (Hsp40) homolog of subfamily C set forth as GENBANK® Accession No. AAH95400.1.

SEQ ID NO:5 is nucleotide sequence of human DnaJ (HSP40) homolog of subfamily C set forth as GENBANK® AccessionNo.BC095400.1.

SEQ ID NO:6 forward primer for region from MCJ intron 1.

SEQ ID NO:7 reverse primer for region from MCJ intron 1.

SEQ ID NO:8 forward primer for MCJ.
SEQ ID NO:9 reverse primer for MCJ.
SEQ ID NO:10 Probe for MCJ.
SEQ ID NO:11: forward primer for MCJ.
SEQ ID NO:12 reverse primer for MCJ.

BRIEF DESCRIPTION OF THE DRAWINGS

FIG. 1A-G shows amino acid sequences, blot images, and a graph illustrating specific tissue distribution of mouse and human MCJ/DnaJC15. FIG. 1A shows alignment of protein sequences of human MCJ/DnaJC15 (top sequence) SEQ ID NO:1, and its ortholog in mouse (bottom sequence) SEQ ID NO:3). Differences in the amino acids of the two sequences are shown in alignment comparison. FIG. 1B shows Northern blot analysis of mouse normal tissue poly-A mRNA using a specific mouse mcj probe. FIG. 1C shows Northern blot analysis of human normal tissue poly-A mRNA using a specific human mcj probe. FIG. 1D is a graph showing relative MCJ expression obtained using of real time RT-PCR for mcj using RNA from mouse B cells, CD4 T cells and CD8 T cells. mRNA levels were normalized to β-2 microglobulin. FIG. 1E shows blot of whole cell extracts from 293T cells transfected with a mouse mcj expressing plasmid (mMCJ) or an empty plasmid (Cont) that were examined for mouse MCJ expression (MCJ) by Western blot analysis. Actin was examined as a loading control. FIG. 1F shows blot showing endogenous MCJ protein expression in mouse liver, heart, kidney and lung that was examined by Western blot analysis. Actin expression was examined as a loading control. FIG. 1G is a blot showing endogenous MCJ protein expression in mouse CD4 T cells and CD8 T cells that was examined by Western blot analysis.

FIG. 2A-I shows photomicrographic images and blots demonstrating that endogenous MCJ localizes to the mitochondria. FIGS. 2A and B shows results of immunoelectron microscopy analysis of endogenous MCJ in purified CD8 T cells (FIG. 2A) and heart (FIG. 2B) from wild type mice. Electron dense gold particle represent MCJ (arrows point to a representative immunoreactivity). Small right panels of FIG. 2A and FIG. 2B represent a higher magnification of the inset area in the left panels. m=mitochondria; mf=myofibrils. 20,000× magnification. Bars indicate 200 nm scale. FIG. 2C shows results of immunoelectron microscopy analysis of MCJ in MCJ-transfected 293T cells. Electron dense gold particle represents MCJ. Bar indicates 200 nm scale. A swollen mitochondrion (m) is shown. FIG. 2 also shows results of confocal microscopy analysis for MCJ (FIG. 2D) and mitotracker (FIG. 2E) in MCJ-transfected 293T cells with FIG. 2F showing overlay of both MCJ and mitotracker. Nuclei were stained with TOPRO (blue). FIG. 2G-I are blots showing MCJ expression in purified cytosolic (Cyt) and mitochondrial (Mito) extracts from (FIG. 2G) mouse heart, (FIG. 2H) mouse CD8 T cells, and (FIG. 2I) human MCF7 cells that were examined by Western blot analysis. GAPDH was used as a marker for the cytosolic fraction and CoxIV as a marker for mitochondrial fraction.

FIG. 3A-J provides graphs showing that MCJ depolarizes mitochondria and decreases ATP levels. FIG. 3A is a graph showing intracellular ATP levels in MCF7 cells and MCF7/siMCJ cells ($10^4$ cells) incubated in medium. FIG. 3B is a graph showing intracellular ATP levels in MCF7/siMCJ cells after incubation (4 h) in medium or rotenone (Roten)

(10 μM). FIG. 3C is a graph showing intracellular ATP levels in 293T cells transfected (16 h) with a MCJ-expressing construct (MCJ) or a control (Cont). FIG. 3D is a graph showing membrane potential as determined by Tetramethylrhodamine, Ethyl Ester, Perchlorate (TMRE) staining and flow cytometry analysis of 293T cells transfected (16 h) with MCJ-expressing (first, shown unshaded) or a control (second, shown crosshatched) constructs. FIG. 3E is a graph showing results of MMP in freshly isolated WT CD8 T cells (filled histogram) and WT CD4 T cells (solid line histogram) that were determined by staining with TMRE and flow cytometry analysis. FIG. 3F is a graph showing results of mROS in freshly isolated WT CD8 T cells (filled histogram) and WT CD4 T cells (solid line histogram) that were determined by staining with MitoSox®-Red and flow cytometry analysis. FIG. 3G is a graph showing results of MMP in freshly isolated WT CD8 T cells (filled histogram) and MCJ KO CD8 T cells (solid line histogram) which were determined as in FIG. 3E. FIG. 3H is a graph showing results of mROS in freshly isolated WT CD8 T cells (filled histogram) and MCJ KO CD8 T cells (solid line histogram) which were determined as in FIG. 3F. FIG. 3I is a graph showing results of MMP in freshly isolated WT CD4 T cells (filled histogram) and MCJ KO CD4 T cells (solid line histogram). FIG. 3J is a graph showing results of mROS in freshly isolated WT CD4 T cells (filled histogram) and MCJ KO CD4 T cells (solid line histogram) was determined as above. Data are representative of three independent experiments.

FIG. 4A-C provides images of blots showing results of (FIG. 4A) Southern blot analysis showing the MCJ targeted (~11 Kb) and wild type (~16 Kb) alleles in wild type (+/+), heterozygous (+/−) and MCJ KO (−/−) mice. FIG. 4B shows blots from Western blot analysis for MCJ in whole cell extracts from liver, heart, CD4 and CD8 T cells from wild type (WT) and MCJ knockout (KO) mice. Actin was analyzed as loading control. FIG. 4C shows a blot obtained using RT-PCR for MCJ using RNA from CD8 T cells isolated from WT, MCJ KO, and MCJ heterozygous mice. Hypoxanthine phosphoribosyltransferase (HPRT) expression was examined as control.

FIG. 5A-B shows plots in FIG. 5A demonstrating CD4 and CD8 T cell distribution in lymph nodes from wild type (WT) and MCJ knock out (KO) mice was analyzed by flow cytometry. Numbers indicate the relative percentage of cells in each quadrant populations. FIG. 5B is a graph showing viability of wild type (WT) (thick line) and MCJ knock out (KO) (thin line) CD8 T cells after activation (3 days) with anti-CD3 and anti-CD28 Abs using the UV-Blue dye in flow cytometry analysis.

FIG. 6A-G provides graphs demonstrating that the loss of MCJ maintains high mitochondrial metabolism in rested effector CD8 T cells. FIG. 6A is a graph showing proliferation of purified CD8 T cells from wild type (WT) and MCJ knock out (KO) mice in response to anti-CD3 and anti-CD28 Abs as determined by $^3$H-Thymidine incorporation. FIG. 6B shows graphs of MMP in WT CD8 T cells (thin line), MCJ KO CD8 T cells (solid line), and WT CD4 T cells (filled histogram) after activation with anti-CD3 and anti-CD28 Abs for 1 day (left) or 2 days (right), as determined by TMRE staining. FIGS. 6C and D are graphs showing results from WT CD8 T cells (filled histogram) and MCJ KO CD8 T cells (solid line) that were activated with anti-CD3 and anti-CD28 Abs for 2 days, washed and incubated in medium alone for 0 h (left panel), 24 h (middle panel) or 48 h (right panel). MMP (FIG. 6C) and mROS (FIG. 6D) were examined as described in FIG. 3. FIG. 6E is a graph showing wild type (WT) and MCJ knock out (KO) CD8 T cells that were activated with anti-CD3 and anti-CD28 Abs (2 days), washed, counted and incubated in medium for 12 h. Intracellular ATP levels in $10^4$ cells were determined. FIG. 6F is a graph showing results when wild type (WT) and MCJ knock out (KO) CD8 T cells were activated for 2 days, washed and equal number of cells was incubated in medium alone for 0, 24 or 48 h. Cell survival was determined by the number of live cells recovered after different periods of time in medium relative to the number of cells plated at day 2. FIG. 6G is a graph of results of CD8 T cells from Thy1.1$^+$ OT-1 (WT) and MCJ KO Thy1.1/1.2$^+$ OT-I (KO) mice were activated with anti-CD3 and anti-CD28 Abs for 2 days, expanded in the presence of IL-2 (25 U/ml) for 2 more days. Equal number of cells were mixed and transferred into Thy1.2$^+$ wild type mice. After 15 days, lymph nodes (LN) and spleen were harvested and the frequency of donor cells was determined by flow cytometry. The percentage of large cells among the corresponding donor cells is shown. Symbols represent individual mice. * denotes p<0.05. Statistical significance between WT and KO lymph nodes (LN) or between WT and KO spleens was determined by student's t test. Data presented here are representative of at least 2 or 3 independent experiments.

FIG. 8A shows images of liver histology by H&E staining from wild type (WT) and MCJ knock out (KO) mice in normal or fasted (36 h) conditions. Bars indicate 200 μm (normal conditions, 100× magnification), 100 μm (normal conditions, 200× magnification), 100 μm (fasted conditions, 100× magnification) and 50 μm (fasted conditions, 200× magnification). FIG. 8B shows micrographic sections from frozen livers of fasted (36 h) wild type (WT) and MCJ knock out (KO) mice that were stained with Oil Red O for detection of lipids. Dark inclusions indicate lipids and higher levels were seen in the WO than in the KO samples. FIGS. 8C and D are graphs showing serum triglyceride levels (FIG. 8C) and FFA (FIG. 8D) in fasted WT and MCJ KO mice (n=4). * denotes p<0.05. Statistical significance was determined by student's t test. FIG. 9A shows images of brown fat (arrows) in wild type and MCJ KO mice and FIG. 9B shows histology of brown fat in wild type and MCJ KO mice under normal feeding conditions. Bars indicate 100 μm scale.

FIG. 10A shows images of brown fat (arrow) in wild type and MCJ KO mice and FIG. 10B shows histology of brown fat in wild type and MCJ KO mice. Bars indicate 100 μm scale.

FIG. 11A-K shows graphs and photomicrographic sections indicating that MCJ deficiency promotes glyconeogenesis during fasting. FIG. 11A shows percentages of total body weight loss after 36 h of fasting relative to the initial weight in wild-type (WT) and MCJ knock-out (KO) mice (n=3). FIG. 11B shows total body weight in WT and MCJ KO mice prior to fasting. FIG. 11C shows comparison of glucose levels in WT and MCJ KO mouse blood 12 h after fasting. FIG. 11D shows comparison of WT and MCJ KO glucose levels in blood prior to and during fasting. FIG. 11E shows comparison of ATP concentrations in liver extracts from WT and MCJ KO mice after fasting (36 h). FIG. 11F shows PAS staining in liver sections from WT and MCJ KO mice after fasting. FIG. 11G shows comparison of glycogen contents in liver extracts from WT and MCJ KO mice (n=3) after fasting (36 h) or normal feeding. FIG. 11H shows percentages of liver weight versus total body weight in WT and MCJ KO mice after fasting (36 h) or normal feeding. FIG. 11I shows Western blot analysis for glycogen synthase (GS) and PEPCK in livers from WT and MCJ KO mice normally fed (Cont) or after fasting (Fast) for 36 h. Livers from two mice are shown for the fasting condition. FIG. 11J shows cholesterol content in livers of WT and MCJ KO mice (n=5) after 4 weeks on a high-cholesterol diet. FIG. 11K shows cholesterol contents in livers of WT and MCJ KO mice (n=4) fed a normal diet. *, P<0.05. Statistical significance was determined by the Student t test. The error bars indicate standard deviations.

FIG. 12A-F provides blots, photomicrographic images, and graphs demonstrating delayed mammary tumor growth in MCJ deficient mice. FIG. 12A is a blot showing MCJ expression in normal mammary gland (N) from a wild type (WT) female mouse, or in mammary tumors isolated from two MMTV-PyMT mice (T1 and T2) that were examined by Western blot analysis using whole cell extracts. FIG. 12B is a blot showing results of MCJ expression examined by Western blot analysis using whole cell extracts (WE), cytosolic extracts (Cyt), and mitochondria extracts (Mito) from MMTV-PyMT tumors. CoxIV and GAPDH were also examined. FIG. 12C is a blot showing results of MCJ expression in mitochondrial extracts from normal mammary tissues (N) or from a MMTV-PyMT tumor (T) examined by Western blot analysis using whole cell extracts. FIG. 12D is a Kaplan-Meier survival curve of MMTV-PyMT wild type (WT) and MCJ KO MMTV-PyMT [MCJ knock out (KO)] mice (n=8). Statistical significance was determined by logrank test. FIG. 12E provides photomicrographic images showing histology (H&E) of mammary tumors from MMTV-PyMT and MCJ KO MMTVPyMT mice. FIG. 12F is a graph showing a ratio of ATP levels in mitochondria extracts relative to ATP levels in cytosolic extracts from tumors of MMTV-PyMT wild type (WT) mice (n=5) and MCJ MMTV-PyMT knock out (KO) mice (n=6). * denotes p<0.05. Statistical significance was determined by student's t test.

FIG. 13A-G provides blots and graphs of results demonstrating that MCJ is a repressor of the mitochondria respiratory chain Complex I activity. FIG. 13A is a blot showing the presence of MCJ, NDUFA9 and NDUFS3 in immunoprecipitates of Complex I from mitochondrial extracts generated from WT and MCJ KO hearts was examined by Western blot analysis. FIG. 13B is a graph showing relative Complex I activity in mitochondrial extracts (10 µg) from wild type (WT) and MCJ knock out (KO) mouse hearts. FIG. 13C is a blot showing expression of NDUFA9 and MCJ in heart mitochondrial extracts from wild type (WT) and MCJ knock out (KO) mice that were examined by Western blot analysis. FIG. 13D is a graph showing relative Complex I activity in mitochondrial extracts (5 µg) from freshly isolated wild type (WT) CD4, wild type (WT) CD8 and MCJ knock out (KO) CD8 T cells. FIG. 13E is a blot showing expression of MCJ, NDUFA9, NDUFS3 and actin in mitochondrial extracts from wild type (WT) CD4, wild type (WT) CD8, and MCJ knock out (KO) CD8 T cells that were examined by Western blot analysis. FIG. 13F is a blot showing expression of NDUFA9 and MCJ in mitochondrial extracts from MCF7 cells and MCF7/siMCJ cells (siMCJ) that were examined by Western blot analysis. FIG. 13G is a graph showing relative Complex I activity in mitochondrial extracts purified from MCF7 and MCF7/siMCJ cells.

DETAILED DESCRIPTION

Figure 7:
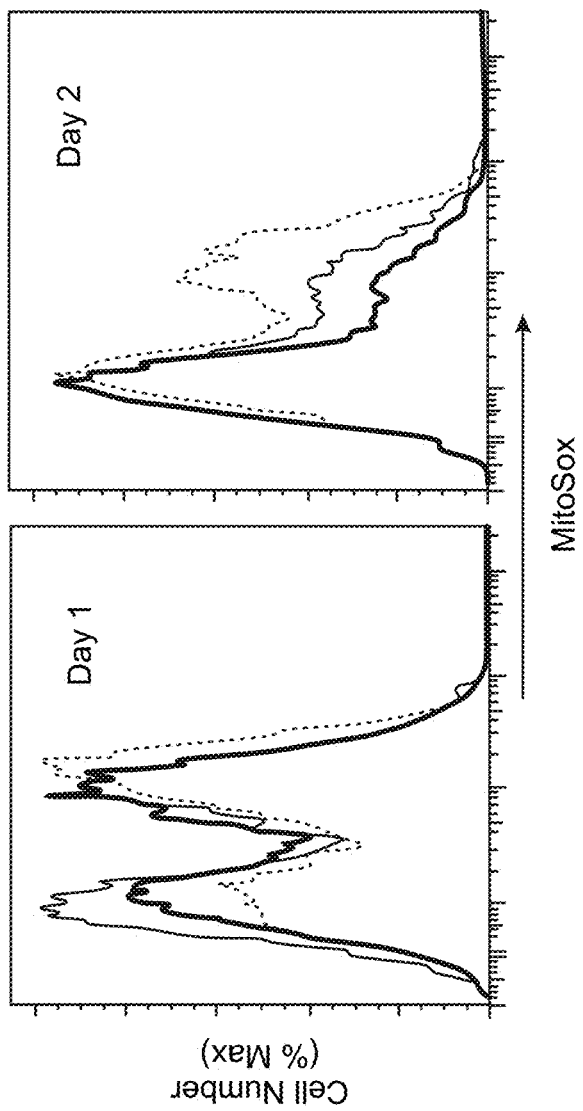
FIG. 7 provides graphs showing results from mROS in wild type (WT) CD8 T cells (thin line), MCJ knock out (KO) CD8 T cells (solid line) and WT CD4 T cells (filled histogram) after activation with anti-CD3 and anti-CD28 Abs for 1 day (left) or 2 days (right), as determined by MitoSox® Red staining.

It has now been discovered that methods and compounds that modulate MCJ polypeptide activity are useful to treat diseases and conditions characterized by metabolic dysregulation. MCJ/DnaJC15 functions as a unique mitochondrial co-chaperone that negatively regulates Complex I of the mitochondrial respiratory chain and ATP production. It has also been determined that this negative feedback attenuates mitochondrial respiration as a response to selective metabolic pressures. Thus, MCJ deficiency impedes slowing of metabolism in response to fasting and an MCJ deficiency enhances mitochondrial lipid oxidation, which results in decreased lipid accumulation in the liver and protection from steatosis. Increased mitochondrial respiration caused by MCJ deficiency has also been shown to delay mammary tumor growth.

The DnaJ family of co-chaperones is the largest with more than 49 members identified in human. Although the DnaJ domain is highly conserved in evolution, the members of this family vary in the non-conserved domains, their tissue expression and cellular localization. The function of most vertebrate DnaJ members in primary tissues remains to be elucidated. In this study the murine ortholog for human MCJ (DnaJC15) and its specific tissue distribution that is conserved between the two species are now described for the first time. It has now been demonstrated that MCJ provides a negative feedback to the mitochondrial respiratory chain and ATP production by interfering with Complex I activity. More importantly, the results show that MCJ is a key regulator of metabolic switches in vivo, a novel function that has not been previously reported for any other member of the DnaJ family. Cellular localization influences the specific functions of DnaJ family members. Using immuno-EM and biochemical analysis in a variety of primary tissues and cells, it has now been shown that MCJ localizes to the mitochondria, in proximity to the inner membrane.

Methylation-Controlled J protein (MCJ)/DnaJC15 is a member of the DnaJC subfamily of cochaperones. MCJ is a small protein of 150 amino acids and a unique member of the DnaJC family. It contains a J-domain located at the C-terminus, as opposed to the common N-terminal position, and its N-terminal region has no homology with any other known protein. In addition, MCJ also contains a transmembrane domain while most DnaJ proteins are soluble. Phylogenetic studies have shown that MCJ is only present in vertebrates where it is highly conserved (Hatle et al., 2007). The amino acid sequence of human DNAJ domain-containing protein MCJ of GENBANK® Accession No. AAD38506.1 is set forth herein as SEQ ID NO:1. SEQ ID NO:2 is mRNA sequence of human DNAJ domain-containing protein MCJ set forth as GENBANK® Accession No. AF126743.1.

GENBANK® Accession No. AAH95400.1 provides amino acid sequence of a human DnaJ (Hsp40) homolog of subfamily C, which is provided herein as SEQ ID NO:4. SEQ ID NO:5 is nucleotide sequence of human DnaJ (HSP40) homolog of subfamily C set forth as GENBANK® AccessionNo. BC095400.1.

MCJ/DnaJC15 is the first DnaJ transmembrane member shown to reside in mitochondria both in human and mouse.

Furthermore, it has now been shown that one of the functions of MCJ is to provide a negative feedback to Complex I in order to attenuate its activity when needed. Thus, in the absence of MCJ there is a significant increase in Complex I activity. A number of associated proteins have been identified as necessary for Complex I to be fully active (McKenzie and Ryan, 2010 *IUBMB Life* 62, 497-502), MCJ is one of a few molecules that repress its activity. Intriguingly, a significant change of Complex I during evolution was the acquisition of both inactive and active forms in vertebrates, while only the active form has been identified in prokaryotes (Clason et al., 2009 *J Struct Biol* 169, 81-88; Ohnishi et al., 1998 *Biochim Biophys Acta* 1365, 301-308). Thus, mammalian Complex I is a mixture of both active and inactive forms. The mechanisms that regulate the balance between both forms remain unclear. Because MCJ originated in vertebrates and represses Complex I activity, it is hypothesized that MCJ regulates the balance between Complex I active and inactive forms.

Among other findings, it has now been shown that (1) MCJ/DnaJC15 is a novel endogenous negative regulator of mitochondrial Complex I; (2) MCJ deficiency results in enhanced mitochondrial respiration and ATP production; (3) MCJ deficiency accelerates lipid metabolism in the liver and prevents the development of steatosis; and (4) negative regulation of mitochondrial oxidative phosphorylation by MCJ affects cancer progression.

The invention pertains, in part, to modulating activity (e.g., levels and/or function) of MCJ/DnaJC15 (also referred to herein as MCJ polypeptide) to regulate metabolic activity in cells, tissues, organs, and subjects. Compositions, compounds, and methods of the invention may be used for treating a subject having, or at risk of having, a metabolic disease or condition that may be characterized by abnormal levels of MCJ activity or undesirable levels of MCJ polypeptide activity. The invention, in part, also relates to methods of diagnosing and assessing the status of metabolic diseases and conditions that may be characterized by abnormal MCJ polypeptide activity. Thus, methods and compounds of the invention are useful to treat and assess such metabolic diseases and conditions in subjects. The invention in part, also relates to modulating MCJ polypeptide activity from an initial activity level in a subject to an activity level that is effective to reduce or eliminate symptoms of a metabolic disease or condition and/or to prevent onset of symptoms of a metabolic disease or condition.

As used herein, a subject shall mean a human or vertebrate mammal including but not limited to a dog, cat, horse, goat, and primate, e.g., monkey. Thus, the invention can be used to treat diseases or conditions in human and non-human subjects. For instance, methods and compositions of the invention can be used in veterinary applications as well as in human prevention and treatment regimens. In some embodiments of the invention, the subject is a human. In some embodiments of the invention, a subject does not have cancer. In certain embodiments of the invention, a subject has cancer. In certain embodiments, a subject is undergoing caloric reduction, e.g., fasting. As used herein, the term "fasting" means a reduced caloric intake, which may include a reduction of up to 5%, 10%, 20%, 30%, 40%, 50%, 60%, 70%, 80%, 90%, or more of the normal caloric intake for a given subject over a predetermined period of time. In some embodiments of the invention a predetermined period of time may be 1, 2, 3, 4, 5, 6, 7 or more days; 1, 2, 3, 4 or more weeks; 1, 2, 3, 4, 5, 6, 7, 8, 9, 10, 11, 12, or more months; and/or 1, 2, 3, 4, 5, or more years. A skilled artisan is able to assess the level of normal caloric intake and a level of reduced caloric intake for a given subject using art-known standards and recommendations, e.g., height/weight tables, etc. As used herein, fasting may be considered a behavioral treatment for a metabolic disease or condition characterized by abnormal MCJ polypeptide activity.

Non-limiting examples of subjects to which the present invention can be applied are subjects who are diagnosed with, suspected of having, or at risk of having, a metabolic disease or condition. Methods of the invention may be applied to a subject who, at the time of treatment, has been diagnosed as having a metabolic disease or condition, or a subject who is considered to be at risk for having or developing a metabolic disease or condition.

In some aspects of the invention, a subject having a metabolic disease or condition is a subject that has detectable abnormality in metabolism as compared to a normal control. In certain aspects of the invention, a subject may have no significant difference compared to a normal control, but it is desired to alter the subject's metabolic activity using methods provided herein. For example, a subject may have a metabolic disease such as diabetes or fatty liver disease that is associated with an abnormality in the subject's metabolic activity compared to a normal control that does not have diabetes or fatty liver disease. In another example, a subject may have a metabolic condition, such as increased exercise, for which it is desirable to increase metabolism in the subject.

In some aspects of the invention, a subject is at risk of having or developing a metabolic disease or condition. A subject at risk of developing a metabolic disease or condition is one who has an increased probability of developing the disease or condition, compared to a control risk of developing the metabolic disease or condition. In some embodiments of the invention, a level of risk may be statistically significant compared to a control level of risk. A subject at risk may include, for instance, subjects having a genetic abnormality, the presence of which has been demonstrated to have a correlative relation to a higher likelihood of developing a metabolic disease or condition; subjects having a family and/or personal medical history of the metabolic disease or condition; subjects exposed to agents such as chemical toxins, or activities; and/or subjects who have previously been treated for the metabolic disease or condition and are in apparent remission.

In some metabolic diseases or conditions MCJ polypeptide activity in a cell, tissue, or subject may be higher relative to MCJ polypeptide activity in a cell, tissue, or subject that does not have the metabolic disease or condition. Thus, in some diseases and conditions that can be treated with methods and compounds of the invention, a higher than normal MCJ polypeptide activity may be characteristic for the metabolic disease or condition, and may also be diagnostic for the metabolic disease or condition. Certain metabolic diseases or conditions may not be characterized by higher than normal MCJ activity level in a cell, tissue, or subject, but can be treated by decreasing MCJ polypeptide activity in a given subject. For example, a subject may have normal levels of MCJ polypeptide activity compared to a control level from a sample, tissue, or subject that does not have the metabolic disease or condition, but decreasing the level in the subject, may treat the metabolic disease or condition in that subject.

Thus, some embodiments of the invention include methods of administering a compound to the cell, tissue or subject in an amount effective to decrease MCJ polypeptide activity in the cell, tissue, or subject as a treatment for the disease or condition. Metabolic diseases and conditions such as overweight, weight gain, obesity, non-alcoholic fatty liver disease, diabetes, insulin-resistance, alcoholic fatty liver disease, dyslipidemia, steatosis (e.g., liver steatosis, heart steatosis, kidney steatosis, muscle steatosis), abeta-lipoproteinemia, glycogen storage disease, Weber-Christian disease, lipodystrophy; liver diseases including but not limited to: liver inflammation, hepatitis, steatohepatitis, Hepatitis C, Genotype 3 Hepatitis C, Alpha 1-antitrypsin deficiency, acute fatty liver of pregnancy, and Wilson disease; kidney diseases; heart diseases: including but not limited to hypertension, ischemia, heart failure, cardiomyopathy; poisoning; HIV; neurodegenerative diseases: including but not limited to Parkinson's disease, Alzheimer's disease; physical exercise; and cancer may be treated by decreasing MCJ-polypeptide activity in a cell, tissue, or subject.

In some metabolic diseases or conditions MCJ polypeptide activity in a cell, tissue, or subject may be lower relative to MCJ polypeptide activity in a cell, tissue, or subject that does not have the metabolic disease or condition. Thus, in some diseases and conditions that can be treated with methods and compounds of the invention, a lower than normal MCJ polypeptide activity may be characteristic for the metabolic disease or condition, and may also be diagnostic for the metabolic disease or condition. Certain metabolic diseases or conditions may not be characterized by lower than normal MCJ activity level in a cell, tissue, or subject, but can be treated by increasing MCJ polypeptide activity in a given subject. For example, a subject may have normal levels of MCJ polypeptide activity compared to a control level from a sample, tissue, or subject that does not have the metabolic disease or condition, but increasing the level in the subject, may treat the metabolic disease or condition in that subject.

Thus, some embodiments of the invention include methods of administering a compound to the cell, tissue or subject in an amount effective to increase MCJ polypeptide activity in the cell, tissue, or subject as a treatment for the disease or condition. Metabolic diseases and conditions such as eating disorders: including but not limited to anorexia, starvation, malnutrition, total parenteral nutrition, severe weight loss, underweight, re-feeding syndrome; gastrointestinal surgery-mediated metabolic alterations: including but not limited to: jejuno-ilial bypass, gastric bypass; and inflammatory/infectious conditions: including but not limited to jujunal diverticulosis with bacterial overgrowth, and inflammatory bowel disease may be treated by increasing MCJ-polypeptide activity in a cell, tissue, or subject.

MCJ polypeptide activity (e.g., level of MCJ polypeptide and/or function of MCJ polypeptide) can be determined and compared to control values of MCJ polypeptide activity according to the invention. A control may be a predetermined value, which can take a variety of forms. It can be a single cut-off value, such as a median or mean. It can be established based upon comparative groups, such as in groups having normal amounts of MCJ polypeptide activity and groups having abnormal amounts of MCJ polypeptide activity. Another example of comparative groups may be groups having one or more symptoms of or a diagnosis of a metabolic disease or condition and groups without having one or more symptoms of or a diagnosis of a metabolic disease or condition. Another comparative group may be a group with a family history of a metabolic disease or condition and a group without such a family history. A predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk (e.g. of a metabolic disease or condition) and the lowest amounts of MCJ polypeptide activity and the highest quadrant or quintile being individuals with the highest risk (e.g. of a metabolic disease or condition) and highest amounts of MCJ polypeptide activity.

The predetermined value, of course, will depend upon the particular population selected. For example, an apparently healthy population will have a different 'normal' range than will a population that is known to have a condition related to abnormal MCJ protein expression or presence. Accordingly, the predetermined value selected may take into account the category in which an individual or cell falls. Appropriate ranges and categories can be selected with no more than routine experimentation by those of ordinary skill in the art. As used herein, "abnormal" means significantly different as compared to a normal control. By abnormally high MCJ polypeptide activity it is meant high relative to a selected control, and may include an increase in activity of at least 0.1%, 0.5%, 1%, 5%, 10%, 20%, 30%, 40%, 50%, 60%, 70%, 80%, 90%, 100%, 150%, 200%, or more, in a subject or cell as compared to the level in a normal control. By abnormally low MCJ polypeptide activity it is meant low relative to a selected normal control, and include a decrease of at least 0.5%, 1%, 5%, 10%, 20%, 30%, 40%, 50%, 60%, 70%, 80%, 90%, 100% in a subject or cell as compared to the level in a normal control. Typically, the control will be based on apparently healthy normal individuals in an appropriate age bracket or apparently healthy cells.

In some aspects of the invention, values of MCJ polypeptide activity determined for a subject may serve as control values for later determinations of MCJ polypeptide activity in that same subject, thus permitting assessment of changes from a "baseline" MCJ polypeptide activity in a subject. Thus, an initial MCJ polypeptide activity level may be determined in a subject and methods and compounds of the invention may be used to decrease the level of MCJ polypeptide activity in the subject, with the initial level serving as a control level for that subject. Using methods and compounds of the invention, the MCJ polypeptide activity in the subject may be decreased by at least 0.5%, 1%, 5%, 10%, 20%, 30%, 40%, 50%, 60%, 70%, 80%, or more compared to the initial level as a treatment for a metabolic disease or condition in the subject. Similarly, an initial MCJ polypeptide activity level may be determined in a subject and methods and compounds of the invention may be used to increase the level of MCJ polypeptide activity in the subject, with the initial level serving as a control level for that subject. Using methods and compounds of the invention, the MCJ polypeptide activity in the subject may be increased by at least 0.5%, 1%, 5%, 10%, 20%, 30%, 40%, 50%, 60%, 70%, 80%, 90%, 100%, or more compared to the initial level as a treatment for a metabolic disease or condition in the subject.

It will be understood that controls according to the invention may be, in addition to predetermined values, samples of materials tested in parallel with the experimental materials. Examples include samples from control populations or control samples generated through manufacture to be tested in parallel with the experimental samples.

It now has been determined that the level of MCJ polypeptide activity mitochondria of cells correlates with the presence or absence of a metabolic disease or condition, and that an increased amount of MCJ polypeptide activity corresponds to an increase in risk of a metabolic disease or condition in subjects. A lower level of MCJ polypeptide activity in mitochondria of cells in a subject has also now been correlated with a more positive prognosis for a subject than the prognosis if the subject's cells have a higher level of MCJ polypeptide activity. For example, although not intended to be limiting, a lower level of MCJ polypeptide activity increases the rate of lipid metabolism in the liver and prevents development of steatosis, which leads to a better prognosis for the subject than if a higher level of MCJ polypeptide activity. Thus, a higher level of expression and function of MCJ in cells is associated with a higher occurrence of metabolic disease and abnormality and a worse prognosis in the subject. One of ordinary skill in the art will recognize that the terms higher, lower, reduced, increased, may be represent relative levels or values as compared to control levels or values.

Although not intending to be bound by any particular theory, it is believed that MCJ resides in the mitochondria where it serves as a negative regulator of Complex I of the mitochondrial respiratory chain. Loss of MCJ leads to increased Complex I activity, hyperpolarization of mitochondria and increased generation of ATP. Enhanced mitochondrial oxidative phosphorylation as a source of energy in the absence of MCJ accelerates fatty acid oxidation and prevents accumulation of lipids in the liver during starvation. In addition, MCJ deficiency has also been found to delay mammary tumor growth correlating with the inability to attenuate mitochondrial function.

In addition, although not intending to be bound by any particular theory, it is believed that modulating MCJ polypeptide activity is also correlated with modulating cytotoxic T ($CD8^+$ T) cell function in cells, tissues and subjects. In some embodiments, methods of the invention may include administering to a subject in need of such treatment an MCJ-modulating compound in an amount effective to increase or decrease an activity of an MCJ polypeptide in a $CD8^+$ T cell. An increase in MCJ polypeptide activity has been found to increase depolarization of a mitochondrion in the $CD8^+$ T cell and a decrease in MCJ polypeptide activity has been found to decrease depolarization of a mitochondrion in the $CD8^+$ T cell. Thus, administering a compound that modulates MCJ polypeptide activity can be used to increase or decrease depolarization of the mitochondrion and thus to modulate cytotoxic T cell function in the subject.

Treatment

The invention in some aspects relates to methods for modulating MCJ polypeptide activity in a cell, tissue, and/or subject. As used herein the term "modulating" means changing a level of an MCJ polypeptide activity (e.g., MCJ polypeptide level and/or function) in a cell. In some embodiments of the invention, changing MCJ polypeptide activity includes changing a level of an MCJ polypeptide in a cell or tissue. Thus, increasing activity of MCJ polypeptide in a cell may include increasing the level (e.g., amount) of the MCJ polypeptide in the cell. Similarly, decreasing the activity of the MCJ polypeptide in a cell may include decreasing the level (e.g., amount) of the MCJ polypeptide in the cell. In some embodiments of the invention, a level of MCJ polypeptide can be changed or modulated by increasing expression of an MCJ polypeptide. Thus, some embodiments of the invention methods may include increasing or decreasing the level of an MCJ polypeptide-encoding nucleic acid in a cell, tissue, or subject, which may result in an increased activity of MCJ polypeptide in the cell, tissue, or subject. Certain embodiments of the invention methods may include directly increasing or decreasing the level of an MCJ polypeptide in a cell, tissue, or subject, for example, by delivering the MCJ polypeptide into the cell, tissue or subject, to treat a metabolic disease or condition characterized by abnormal MCJ polypeptide activity. As set forth elsewhere herein, in some embodiments of the invention, cells that may be treated with a method of the invention to increase or decrease a level of an MCJ polypeptide or its activity may include, but are not limited to, liver cells, muscle cells, cardiac cells, circulatory cells, neuronal cells, glial cells, fat cells, skin cells, hematopoietic cells, epithelial cells, sperm, oocytes, muscle cells, adipocytes, kidney cells, hepatocytes, or pancreas cells. In some embodiments of the invention, a cell is a cancer cell, an example of which may be a tumor cell.

As used herein, the terms "treat", "treated", or "treating" when used with respect to a disorder such as a metabolic disease or condition that may be characterized by abnormal MCJ polypeptide activity may refer to a prophylactic treatment that decreases the likelihood of a subject developing the disease or condition, and also may refer to a treatment after the subject has developed the disease or condition in order to eliminate or reduce the level of the disease or condition, prevent the disease or condition from becoming more advanced (e.g., more severe), and/or slow the progression of the disease compared to in the absence of the therapy.

In certain embodiments of the invention, changing MCJ polypeptide activity includes increasing or decreasing functioning of an MCJ polypeptide in a cell, tissue, or subject. In some such embodiments, the level of the MCJ polypeptide does not change, but the function of one or more of the MCJ polypeptides in a cell may be altered, for example either increased or decreased. Examples of methods that may alter the function of an MCJ polypeptide may include, but are not limited to contacting the MCJ polypeptide with an antibody or functional fragment thereof that binds to an MCJ polypeptide and alters its function. For example, in some embodiments of the invention an antibody that inhibits MCJ function may be delivered to a cell as part of a treatment regimen. Similarly, in some embodiments of the invention, compounds that enhance or inhibit MCJ function may be administered to a cell or subject and result in a modulation of MCJ polypeptide activity. Compounds that enhance or inhibit an MCJ polypeptide function and/or enhanced or inhibit an MCJ polypeptide level may be referred to herein as MCJ-modulating compounds.

In some embodiments of the invention, an MCJ-modulating compound may include an MCJ molecule, an anti-MCJ polypeptide antibody or functional fragment thereof, a small molecule MCJ inhibitor, or a small molecule MCJ enhancer. Examples of MCJ molecules include MCJ polypeptides or nucleic acids that encode MCJ polypeptides. As used herein an MCJ-modulating compound may be a compound that modulates (e.g, increases or decreases) MCJ polypeptide activity in a cell, tissue, and/or subject. An MCJ-modulating compound that decreases or reduces MCJ polypeptide activity may be referred to as an MCJ inhibitor compound and an MCJ-modulating compound that increases or enhances MCJ polypeptide activity may be referred to as an MCJ enhancer compound.

Thus, compounds that increase or decrease an MCJ polypeptide activity may be administered in an effective amount to a subject in need of treatment of a metabolic disease or condition. Administering a compound that increases or a compound that decreases MCJ polypeptide activity to a subject may reduce a metabolic disease or condition in the subject. In certain metabolic disease and/or conditions in which it is desirable to reduce MCJ polypeptide activity using a treatment and/or compound of the invention, an MCJ inhibiting compound may be administered. Non-limiting examples of such metabolic diseases or conditions include but are not limited to: overweight, weight gain, obesity, non-alcoholic fatty liver disease, diabetes, insulin-resistance, alcoholic fatty liver disease, dyslipidemia, steatosis (e.g., liver steatosis, heart steatosis, kidney steatosis, muscle steatosis), abeta-lipoproteinemia, glycogen storage disease, Weber-Christian disease, lipodystrophy; liver diseases including but not limited to: liver inflammation, hepatitis, steatohepatitis, Hepatitis C, Genotype 3 Hepatitis C, Alpha 1-antitrypsin deficiency, acute fatty liver of pregnancy, and Wilson disease; kidney diseases; heart diseases: including but not limited to hypertension, ischemia, heart failure, cardiomyopathy; poisoning; HIV; neurodegenerative diseases: including but not limited to Parkinson's disease, Alzheimer's disease; physical exercise; and cancer. In some embodiments of the invention, the metabolic disease or condition is high cholesterol and methods of the invention to reduce MCJ activity may be used to reduce cholesterol in a cell, tissue, or subject.

In certain metabolic conditions in which it is desirable to increase MCJ polypeptide activity using a treatment and/or compound of the invention, an MCJ enhancing compound may be administered. Non-limiting examples of such metabolic diseases or conditions include but are not limited to: eating disorders: including but not limited to anorexia, starvation, malnutrition, total parenteral nutrition, severe weight loss, underweight, re-feeding syndrome; gastrointestinal surgery-mediated metabolic alterations: including but not limited to: jejuno-ilial bypass, gastric bypass; and inflammatory/infectious conditions: including but not limited to jujunal diverticulosis with bacterial overgrowth, and inflammatory bowel disease.

A compound useful to treat a metabolic disease or condition for which it is desirable to alter or modulate MCJ polypeptide activity may, in some embodiments of the invention be an MCJ polypeptide or nucleic acid that encodes an MCJ polypeptide. Thus, a method of the invention may include administering an exogenous MCJ polypeptide or exogenous MCJ polypeptide-encoding nucleic acid to a subject.

As used herein, the terms "protein" and "polypeptide" are used interchangeably and thus the term polypeptide may be used to refer to a full-length protein and may also be used to refer to a fragment of a full-length protein. As used herein with respect to polypeptides, proteins, or fragments thereof, and nucleic acids that encode such polypeptides the term "exogenous" means the compound is administered to a cell or subject and was not naturally present in the cell or subject. It will be understood that an exogenous MCJ polypeptide or MCJ polypeptide-encoding nucleic acid may be identical to an endogenous MCJ polypeptide or MCJ polypeptide-encoding nucleic acid, respectively, in terms of its sequence, but was administered to the cell or subject.

According to some aspects of the invention, full-length MCJ polypeptides or fragments of full-length MCJ polypeptide may be administered in methods of the invention. Fragments of the invention may be fragments that retain a distinct functional capability of the polypeptide. Functional capabilities that can be retained in a fragment include interaction with antibodies, and interaction with other polypeptides or fragments thereof. Polypeptide fragments may be natural fragments or may be synthesized using art-known methods, and tested for function using the methods exemplified herein. Full-length MCJ and fragments of MCJ that are useful in methods and compositions of the invention may be recombinant polypeptides.

A fragment of a full-length MCJ polypeptide may comprise at least up to n−1 contiguous amino acids of the full-length MCJ polypeptide having a consecutive sequence found in a wild-type MCJ polypeptide or in a modified MCJ polypeptide sequence as described herein (with "n" equal to the number of amino acids in the full-length MCJ polypeptide). Thus, for example, a fragment of a 150 amino acid-long MCJ polypeptide would be at least 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, or 149 (including each integer in between) contiguous amino acids of the 150 amino acid MCJ polypeptide. In some embodiments, a fragment includes the C-terminal region of an MCJ polypeptide. Such MCJ polypeptides that are fragments of full-length MCJ polypeptide may be useful for a variety of purposes, including for administration as MCJ-modulating compounds and for preparing MCJ-modulating compounds such as antibodies that bind specifically to synthetic and natural MCJ polypeptides.

A "modified" wild-type or mutant full-length MCJ polypeptide or polypeptide that is a fragment thereof may include deletions, point mutations, truncations, amino acid substitutions and/or additions of amino acids or non-amino acid moieties. Modifications of a polypeptide of the invention may be made by modification of the nucleic acid that encodes the polypeptide or alternatively, modifications may be made directly to the polypeptide, such as by cleavage, addition of a linker molecule, addition of a detectable moiety, such as a fluorescent label, and the like. Modifications also embrace fusion proteins comprising all or part of the polypeptide's amino acid sequence.

In general, modified polypeptides (e.g. modified MCJ wild-type or mutant polypeptides) may include polypeptides that are modified specifically to alter a feature of the polypeptide unrelated to its physiological activity. For example, cysteine residues can be substituted or deleted to prevent unwanted disulfide linkages. A residue may be added at the N or C-terminal end of the polypeptide, for example, a cysteine (C) or other amino acid residue may be added at the extreme C-terminal end of a MCJ polypeptide. MCJ polypeptides can be synthesized with modifications and/or modifications can be made in an MCJ polypeptide by selecting and introducing an amino acid substitution, deletion, or addition. Modified polypeptides then can be tested for one or more activities (e.g., modulating MCJ-polypeptide activity in a cell or subject, treatment of a metabolic disease or condition, altering a mitochondrial membrane depolarization, etc.) to determine which modification provides a modified polypeptide with the desired properties.

The skilled artisan will also realize that conservative amino acid substitutions may be made in a polypeptide to provide functionally equivalent polypeptides, i.e., a modified MCJ polypeptide that retains a functional capability of an un-modified MCJ polypeptide in a treatment method of the invention. As used herein, a "conservative amino acid substitution" refers to an amino acid substitution that does not alter the relative charge or size characteristics of the polypeptide in which the amino acid substitution is made. Modified MCJ polypeptides can be prepared according to methods for altering polypeptide sequence and known to one of ordinary skill in the art such. Exemplary functionally equivalent MCJ polypeptides include conservative amino acid substitutions of an MCJ polypeptide, or fragments thereof, such as a modified MCJ polypeptide. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in an MCJ polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis, or by chemical synthesis of a gene encoding the MCJ polypeptide. Where amino acid substitutions are made to a small fragment of a polypeptide, the substitutions can be made by directly synthesizing the polypeptide. The activity of functionally equivalent fragments of MCJ polypeptides can be tested by cloning the gene encoding the altered polypeptide into a bacterial or mammalian expression vector, introducing the vector into an appropriate host cell, expressing the altered polypeptide, and testing for a functional capability of the polypeptide as disclosed herein.

In some embodiments of the invention, a level or function of a MCJ polypeptide may be modulated by genetically introducing an MCJ polypeptide into a cell and/or mitochondria, and reagents and methods are provided for genetically targeted expression of MCJ polypeptides. Genetic targeting can be used to deliver MCJ polypeptides to specific cell types, to specific cell subtypes, to specific spatial regions within an organism, and to sub-cellular regions within a cell. Genetic targeting also relates to the control of the amount of an MCJ polypeptide expressed, and the timing of the expression. Some embodiments of the invention include a reagent for genetically targeted expression of an MCJ polypeptide, wherein the reagent comprises a vector that contains a nucleic acid that encodes an MCJ polypeptide or encodes a functional fragment of an MCJ polypeptide.

As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert MCJ polypeptides into dividing and non-dividing cells and can insert MCJ polypeptides to cells that are in vivo, in vitro, or ex vivo cells.

Vectors useful in methods of the invention may include additional sequences including, but not limited to one or more signal sequences and/or promoter sequences, or a combination thereof. Expression vectors and methods of their use are well known in the art. In certain embodiments of the invention, a vector may be a lentivirus comprising a nucleic acid or gene that encodes an MCJ polypeptide of the invention or a variant thereof. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of an MCJ polypeptide in a wide variety of cell types—thus a promoter for a gene that is widely expressed in a variety of cell types, for example a "housekeeping gene" can be used to express an MCJ polypeptide in a variety of cell types. Non-limiting examples of general promoters are provided elsewhere herein and suitable alternative promoters are well known in the art. In certain embodiments of the invention, a promoter may be an inducible promoter, examples of which include, but are not limited to tetracycline-on or tetracycline-off, etc.

Certain aspects of the invention include methods of administering antibodies or antigen-binding fragments thereof which specifically bind to an MCJ polypeptide to alter MCJ polypeptide activity, e.g., to decrease MCJ polypeptide activity. In some embodiments of the invention such antibodies or antigen-binding fragments thereof may be administered to a cell and/or subject to inhibit MCJ polypeptide activity in the cell and/or subject. The term "antigen-binding fragment" of an antibody as used herein, refers to one or more portions of an antibody that retain the ability to specifically bind to an antigen (e.g., an MCJ polypeptide). One may prepare and test an antigen-binding fragment of an MCJ-modulating antibody for use in methods of the invention using art-known methods and routine procedures. In some embodiments of the invention, the antibodies are recombinant antibodies, polyclonal antibodies, monoclonal antibodies, humanized antibodies or chimeric antibodies, or a mixture of these.

Examples of antibodies known to specifically bind the MCJ polypeptide set forth herein as SEQ ID NO:1, include, but are not limited to monoclonal antibodies i) WN.F3, generated from hybridoma N-MCJ 3C1.3F3, which was deposited under ATCC no. #PTA-8135; ii) WN.A12, generated from hybridoma cell line N-MCJ 3C1.5A12, which was deposited under ATCC no. #PTA-8133; and iii) WN.E4 generated from hybridoma cell line N-MCJ 2A2.5E4, which was deposited under. ATCC no. #PTA-8134. (see US Patent Publication US20100129931, published May 27, 2010, which is incorporated herein by reference). The WN.F3, WN.A12, and WN.E4 antibodies are examples of antibodies that may be used in methods of the invention as MCJ-modulating compounds. Additional antibodies for use in methods of the invention may be produced and tested using art-known methods in conjunction with the disclosure herein and in the disclosure set forth in US Patent Publication US20100129931.

Additional compounds that may be administered in treatment methods of the invention include small molecules or chemicals that inhibit MCJ polypeptide activity and small molecules or chemicals that enhance MCJ polypeptide activity. Methods of identifying and testing such small molecules and chemicals may include use of art-known library screening and testing procedures in conjunction with the teaching provided herein.

MCJ polypeptide modulating compounds of the invention may be administered singly or in combination with one or more additional compounds. In some embodiments, a compound of the invention may act in a synergistic manner with one or more other therapeutic agents or treatments and increase the effectiveness of the one or more therapeutic agents or activities. Thus, for example, administration of a compound that inhibits MCJ polypeptide activity in conjunction with a caloric reduction treatment may enhance the efficacy of the caloric reduction treatment. Thus, an MCJ inhibitor compound may act synergistically to increase the effectiveness of one or more agents or treatments that can be administered to treat a metabolic disease or condition.

It will be understood that additional MCJ-modulating compounds can be identified and used in methods of the invention. For example, candidate compounds can be can be tested for their ability to increase MCJ polypeptide activity (level and/or function) and their ability to treat a metabolic disease or condition using assays and methods presented herein.

MCJ-modulating compounds of the invention (such as compounds comprising an MCJ molecule, an anti-MCJ polypeptide antibody or functional fragment thereof, a small molecule MCJ inhibitor, or a small molecule MCJ enhancer, etc.) described herein can be used alone or in conjugates with other molecules such as targeting agents, labeling agents, and/or cytotoxic agents in treatment methods of the invention.

Targeting agents useful according to the methods of the invention are those that direct a compound of the invention to a specific cell type to be treated such as liver cells, muscle cells, cardiac cells, circulatory cells, neuronal cells, glial cells, fat cells, skin cells, hematopoietic cells, epithelial cells, sperm, oocytes, muscle cells, adipocytes, kidney cells, hepatocytes, or pancreas cells, or to an organelle such as a mitochondrion. A targeting compound of choice will depend upon the nature of the metabolic disease or condition. In some instances it may be desirable to target the agent to skeletal muscle, cardiac muscle, kidney, liver, brain, etc. Those of ordinary skill in the art will be aware of and able to select and use suitable targeting agents for use in methods of the invention. Non-limiting examples of targeting agents for mitochondria are Gramicidin S based mitochondrial targeting agents, agents utilizing the carnitine-acylcarnitine translocase system, cytochromes, malate dehydrogenase. Examples of targeting signals that may be used in some embodiments of the invention are set forth in Diekert, K., et al., PNAS (1999) vol 96, No. 21, 11752-11757; Addya, S., et al., J. Cell Biology, (1997) Vol. 139, No. 3, 589-599; Del Gaizo, V., et al., (2003) Mol. Gen. and Metabol. Vol. 80, 170-180, which are incorporated herein by reference.

Labeling agents may be used in methods of the invention to determine the location of MCJ polypeptides in cells and tissues and also, may be used to assess the cell, tissue, or organelle location of treatment compounds that have been administered. Procedures for attaching and utilizing labeling agents such as enzymatic labels, dyes, radiolabels, etc. are well known in the art.

Compositions, compounds, and methods of the invention may be enhanced by utilization in combination with other procedures for treating a metabolic disease or condition. In some instances a treatment procedure may involve administration of another therapeutic agent or treatment such a medicament and/or a behavioral treatment, caloric limitation, surgery, etc. Thus, in some embodiments of the invention, administration of a compound of the invention (e.g., administration of an anti-MCJ antibody or functional fragment thereof, an MCJ polypeptide-encoding nucleic acid, MCJ polypeptide, or a small molecule MCJ enhancer or inhibitor) may be performed in conjunction with therapies for treating the metabolic disease or condition such as caloric limitation, increased physical activity, surgery, etc. Treatment methods of the invention that include administration of a MCJ-modulating compound can be used at any stages of pre-metabolic disease or condition or when the metabolic disease or condition is at a later stage, including but not limited to early-stage, mid-stage, and late-stage of the metabolic disease or condition, including all times before and after any of these stages. Methods of the invention may also be used for subjects who have previously been treated with one or more other medicaments or behavioral therapy methods that were not successful, were minimally successful, and/or are no longer successful at slowing or stopping progression of the metabolic disease or disorder in the subject.

Effective Amounts for Treatments

MCJ-modulating compounds of the invention, (e.g., an anti-MCJ antibody or functional fragment thereof, an MCJ polypeptide-encoding nucleic acid, MCJ polypeptide, or a small molecule MCJ enhancer or inhibitor, etc.) are administered to the subject in an effective amount for treating the metabolic disease or condition. An "effective amount for treating a metabolic disease or condition" is an amount necessary or sufficient to realize a desired biologic effect. For example, an effective amount of a compound of the invention could be that amount necessary to (i) slow or halt progression of the disease or condition; or (ii) reverse one or more symptoms of the metabolic disease or condition. According to some aspects of the invention, an effective amount is that amount of a compound of the invention alone or in combination with another medicament or treatment, which when combined or co-administered or administered alone, results in a therapeutic response in the metabolic disease or condition, either in the prevention or the treatment of the metabolic disease or condition. The biological effect may be the amelioration and or absolute elimination of symptoms resulting from the metabolic disease or condition. In another embodiment, the biological effect is the complete abrogation of the metabolic disease or condition, as evidenced for example, by a diagnostic test that indicates the subject is free of the disease or condition.

Typically an effective amount of a compound or drug to increase MCJ polypeptide activity or a compound or drug to decrease MCJ polypeptide will be determined in clinical trials, establishing an effective dose for a test population versus a control population in a blind study. In some embodiments, an effective amount will be that results in a desired response, e.g., an amount that diminishes a metabolic disease or condition in cells or tissues in a subject with the metabolic disease or condition. Thus, an effective amount to treat a metabolic disease or condition characterized by a reduced MCJ polypeptide activity, and/or a metabolic disease or condition for which it is desirable to increase MCJ polypeptide activity, may be the amount that when administered increases the amount of MCJ polypeptide activity in the subject to an amount that that is above the amount that would occur in the subject or tissue without the administration of the composition. Similarly, an effective amount to treat a metabolic disease or condition characterized by increased MCJ polypeptide activity, and/or a metabolic disease or condition for which it is desirable to decrease MCJ polypeptide activity, may be the amount that when administered decreases MCJ polypeptide activity in a cell, tissue, and/or subject to an amount that that is below the amount that would occur in the subject or tissue without the administration of the compound or drug. In the case of treating a metabolic disease or condition the desired response may be reducing or eliminating one or more symptoms of the metabolic disease or condition in the cell, tissue, and/or subject. The reduction or elimination may be temporary or may be permanent. The status of the metabolic disease or condition can be monitored using methods of determining MCJ polypeptide activity or levels of nucleic acids that encode an MCJ polypeptide, etc. In some aspects of the invention, a desired response to treatment of the metabolic disease or condition also can be delaying the onset or even preventing the onset of the metabolic disease or condition.

An effective amount of a compound that modulates (increases or decreases) MCJ polypeptide activity (also referred to herein as a pharmaceutical compound) may also be determined by assessing physiological effects of administration on a cell or subject, such as a decrease of a metabolic disease or condition following administration. Assays suitable to determine efficacy of a pharmaceutical compound of the invention will be known to those skilled in the art and can be employed for measuring the level of the response to a treatment and an amount of a pharmaceutical compound administered to a subject can be modified based, at least in part, on such measurements. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated; the severity of the condition, the duration of the treatment, the nature of the concurrent therapy (if any), the specific route of administration, and additional factors within the knowledge and expertise of the health practitioner. For example, an effective amount may depend upon the degree to which an individual has abnormally low or abnormally high levels of MCJ polypeptide activity, and/or the desired level of MCJ polypeptide activity to attain that is effective to treat the metabolic disease or condition.

The effective amount of a compound of the invention in the treatment of a metabolic disease or condition or in the reduction of the risk of developing a metabolic disease or condition may vary depending upon the specific compound used, the mode of delivery of the compound, and whether it is used alone or in combination. The effective amount for any particular application can also vary depending on such factors as the metabolic disease or condition being treated, the particular compound being administered, the size of the subject, or the severity of the metabolic disease or condition. A skilled artisan can empirically determine the effective amount of a particular compound of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

A pharmaceutical compound dosage may be adjusted by an individual health care provider or veterinarian, particularly in the event of any complication. A therapeutically effective amount typically varies from 0.01 mg/kg to about 1000 mg/kg, from about 0.1 mg/kg to about 200 mg/kg, or from about 0.2 mg/kg to about 20 mg/kg, in one or more dose administrations daily, for one or more days. The absolute amount will depend upon a variety of factors including a concurrent treatment, the number of doses and the individual subject parameters including age, physical condition, size and weight. These are factors well known to those of ordinary skill in the art and can be addressed with no more than routine experimentation. In some embodiments, a maximum dose can be used, that is, the highest safe dose according to sound medical judgment.

Multiple doses of compounds of the invention are also contemplated. In some instances, a compound of the invention, (e.g., an anti-MCJ antibody or functional fragment thereof, an MCJ polypeptide-encoding nucleic acid, MCJ polypeptide, or a small molecule MCJ enhancer or inhibitor, etc.) can be administered at least daily, every other day, weekly, every other week, monthly, etc. Doses may be administered once per day or more than once per day, for example, 2, 3, 4, 5, or more times in one 24 hour period.

Pharmaceutical compounds of the invention may be administered alone, in combination with each other, and/or in combination with other drug therapies, or other treatment regimens that are administered to subjects with a metabolic disease or condition. Pharmaceutical compositions used in the foregoing methods preferably are sterile and contain an effective amount of a therapeutic compound that will modulate a MCJ polypeptide activity to a level sufficient to produce the desired response in a unit of weight or volume suitable for administration to a subject.

The doses of a composition to modulate the MCJ polypeptide activity that is administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Administration Methods

A variety of administration routes for a MCJ-modulating compound are available. The particular delivery mode selected will depend, of course, upon the particular condition being treated and the dosage required for therapeutic efficacy. Methods of this invention, generally speaking, may be practiced using any mode of administration that is medically acceptable, meaning any mode that produces effective levels of protection without causing clinically unacceptable adverse effects. In some embodiments of the invention, a compound of the invention may be administered via an oral, enteral, mucosal, percutaneous, and/or parenteral route. The term "parenteral" includes subcutaneous, intravenous, intramuscular, intraperitoneal, and intrasternal injection, or infusion techniques. Other routes include but are not limited to nasal (e.g., via a gastro-nasal tube), dermal, vaginal, rectal, and sublingual. Delivery routes of the invention may include intrathecal, intraventricular, or intracranial. In some embodiments of the invention, a compound of the invention may be placed within a slow release matrix and administered by placement of the matrix in the subject. In some aspects of the invention, a compound (such as an anti-MCJ antibody or functional fragment thereof, an MCJ polypeptide-encoding nucleic acid, MCJ polypeptide, or a small molecule MCJ enhancer or inhibitor, etc.) may be delivered to a subject cell using nanoparticles coated with an delivery agent that targets a specific cell or organelle, a non-limiting example of which is a mitochondrion.

Compounds of the invention may be administered in formulations, which may be administered in pharmaceutically acceptable solutions, which may routinely contain pharmaceutically acceptable concentrations of salt, buffering agents, preservatives, compatible carriers, adjuvants, and optionally other therapeutic ingredients. According to methods of the invention, the compound may be administered in a pharmaceutical composition. In general, a pharmaceutical composition comprises the compound of the invention and a pharmaceutically-acceptable carrier. Pharmaceutically-acceptable carriers are well-known to those of ordinary skill in the art. As used herein, a pharmaceutically-acceptable carrier means a non-toxic material that does not interfere with the effectiveness of the biological activity of the active ingredients, e.g., the ability of the compound such as an anti-MCJ antibody or functional fragment thereof, an MCJ polypeptide-encoding nucleic acid, MCJ polypeptide, or a small molecule MCJ enhancer or inhibitor, etc. to treat the metabolic disease or condition.

Pharmaceutically acceptable carriers include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Compounds of the invention may be administered directly to a tissue. In some embodiments, the tissue to which the compound is administered is a tissue in which the metabolic disease or condition is likely to arise. Direct tissue administration may be achieved by direct injection. Compounds may be administered once, or alternatively they may be administered in a plurality of administrations. If administered multiple times, the compounds may be administered via different routes. For example, the first (or the first few) administrations may be made directly into the affected tissue while later administrations may be systemic.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with or without an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day may be used as needed to achieve appropriate systemic or local levels of compounds.

In yet other embodiments, a delivery vehicle is a biocompatible microparticle or implant that is suitable for implantation into the mammalian recipient. Exemplary bioerodible implants that are useful in accordance with this method are described in PCT Publication No. WO 95/24929 (incorporated by reference herein), which describes a biocompatible, biodegradable polymeric matrix for containing a biological macromolecule. Such delivery means are well known in the art and can be used to achieve sustained release of a compound of the invention in a subject, and may be selected not to degrade, but rather, to release by diffusion over an extended period of time.

Both non-biodegradable and biodegradable polymeric matrices can be used to deliver the compounds of the invention to the subject. In some embodiments, a matrix may be biodegradable. Matrix polymers may be natural or synthetic polymers. A polymer can be selected based on the period of time over which release is desired, generally in the order of a few hours to a year or longer. Typically, release over a period ranging from between a few hours and three to twelve months can be used. The polymer optionally is in the form of a hydrogel that can absorb up to about 90% of its weight in water and further, optionally is cross-linked with multivalent ions or other polymers.

In general, compounds of the invention may be delivered using the bioerodible implant by way of diffusion, or by degradation of the polymeric matrix. Exemplary synthetic polymers for such use are well known in the art. Biodegradable polymers and non-biodegradable polymers can be used for delivery of compounds of the invention using art-known methods. Bioadhesive polymers such as bioerodible hydrogels (see H. S. Sawhney, C. P. Pathak and J. A. Hubell in Macromolecules, 1993, 26, 581-587, the teachings of which are incorporated herein) may also be used to deliver compounds of the invention for treatment. Additional suitable delivery systems can include time-release, delayed release or sustained release delivery systems. Such systems can avoid repeated administrations of the compound, increasing convenience to the subject and the physician. Many types of release delivery systems are available and known to those of ordinary skill in the art. (See for example: U.S. Pat. Nos. 5,075,109; 4,452,775; 4,675,189; 5,736,152; 3,854,480; 5,133,974; and 5,407,686 (the teaching of each of which is incorporated herein by reference). In addition, pump-based hardware delivery systems can be used, some of which are adapted for implantation.

Use of a long-term sustained release implant may be particularly suitable for prophylactic treatment of subjects and for subjects at risk of developing a recurrent metabolic disease or condition. Long-term release, as used herein, means that the implant is constructed and arranged to delivery therapeutic levels of the active ingredient for at least 30 days, 60 days, 90 days or longer. Long-term sustained release implants are well-known to those of ordinary skill in the art and include some of the release systems described above.

Therapeutic formulations of compounds of the invention may be prepared for storage by mixing the compound having the desired degree of purity with optional pharmaceutically acceptable carriers, excipients or stabilizers [Remington's Pharmaceutical Sciences 21$^{st}$ edition, (2006)], in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Detection Assays and Diagnostics

Certain aspects of the invention include methods to assess the status of a metabolic disease or condition characterized by abnormal MCJ polypeptide activity. Such methods may include determining a level or function of an MCJ polypeptide and comparing the determined level or function with a control level or function. In some embodiments of the invention methods include use of antibodies or antigen-binding fragments that specifically bind MCJ polypeptide in assays to detect a level of an MCJ polypeptide, or a nucleic acid that encodes an MCJ polypeptide in a cell and/or subject. Such assays may include obtaining a biological sample from a subject, determining the level of an MCJ molecule in the biological sample, and comparing the level to a control level. As used herein a biological sample may be an in vitro biological sample, or may a sample that is detected (e.g., obtained) in vivo. As used herein, a biological sample may be a cell sample, tissue sample, blood sample, bodily fluid sample, subcellular sample, etc. A biological sample may include cells, tissues, or organelles and may include cell types such as but not limited to: liver cells, muscle cells, cardiac cells, circulatory cells, neuronal cells, glial cells, fat cells, skin cells, hematopoietic cells, epithelial cells, sperm, oocytes, muscle cells, adipocytes, kidney cells, hepatocytes, pancreas cells, etc. In some embodiments of the invention, a biological sample may comprise one or more cancer cells. In certain embodiments of the invention, a biological sample does not comprise a cancer cell.

Assays to assess a metabolic disease or condition characterized by abnormal MCJ polypeptide activity may include but are not limited to (1) characterizing the impact of MCJ polypeptide activity on treatment of a metabolic disease or condition in a subject; (2) evaluating a treatment to alter MCJ polypeptide activity (e.g., level and/or function) in a subject; (3) selecting a treatment for a metabolic disease or condition based at least in part on the determined MCJ polypeptide activity in cells of the subject; and (4) determining the status of a metabolic disease or condition in a subject. Thus, subjects can be characterized, treatment regimens can be monitored, treatments can be selected and diseases status can be better understood using embodiments of methods of the present invention. For example, the antibodies or antigen-binding fragments thereof of the invention and other methods of the invention are useful in to measure or determine MCJ-polypeptide activity in a cell and/or subject, which may be a direct indicator of a metabolic disease or condition in the cell and/or subject.

The invention, in some aspects, includes various assays to determine activity of an MCJ polypeptide. Methods of the invention that are useful to determine MCJ polypeptide activity (levels and/or function of the MCJ polypeptide) in cells, tissues, subjects, and samples (e.g., from subjects, in culture, etc.), include, but are not limited to: binding assays, such as using antibodies or antigen-binding fragments thereof that bind specifically to an MCJ polypeptide; gel electrophoresis; mass spectrometry; NMR; and the like. Immunoassays may be used according to the invention including, but not limited to, sandwich-type assays, competitive binding assays, one-step direct tests and two-step tests such as those routinely used in the art. Assessment of binding of antibodies that specifically bind MCJ polypeptide may also be done in vivo—in living subjects using art-known detectable labels and suitable in vivo methods.

Methods and assays of the invention (e.g. binding assays, gel electrophoresis; mass spectrometry; NMR; and the like) may be used to determine changes in MCJ polypeptide activity in a subject or cell sample (e.g., cell culture) over time. This allows monitoring of MCJ polypeptide activity in a subject who is to undergo treatment for a metabolic disease or condition and also enables to monitoring in a subject who is currently undergoing therapy for a metabolic disease or condition. Thus, methods of the invention may be used to diagnose or assess a metabolic disease or condition in a subject and may also be used to assess the efficacy of a therapeutic treatment of a metabolic disease or condition for assessment of the activity of an MCJ polypeptide in a subject at various time points. For example, a subject's MCJ polypeptide activity can be determined prior to the start of a therapeutic regimen (either prophylactic or as a treatment of a metabolic disease or condition), during the treatment regimen and/or after a treatment regimen, thus providing information on the status of the metabolic disease or condition in the subject.

Assessment of efficacy of candidate MCJ-modulating compounds to increase or decrease expression of MCJ polypeptide-encoding nucleic acid or an MCJ polypeptide in a cell or tissue may also be done using assays of the invention in cells from culture—e.g., as screening assays to assess candidate MCJ-modulating compounds to modulate MCJ polypeptide activity. MCJ-modulating compounds that alter MCJ polypeptide activity in a cell, tissue, or subject may be used in the treatment of a metabolic disease or condition or as a pretreatment for a metabolic disease or condition (e.g., to prepare a cell or subject for subsequent treatment).

It will be understood that a therapeutic regimen may be either prophylactic or a treatment of a metabolic disease or condition in a subject. The invention in some aspects provides methods that may be used to monitor a subject's response to prophylactic therapy and/or treatment for a metabolic disease or condition provided to a subject. Methods of the invention (e.g. binding assays, gel electrophoresis; mass spectrometry; NMR; and the like) may also be useful to monitor the onset, progression, or regression of metabolic disease or condition in a subject at risk of developing the metabolic disease or condition. MCJ polypeptide activity may be determined in two, three, four, or more biological samples obtained from a subject at separate times. The MCJ polypeptide activity determined in the samples may be compared and changes in the activity over time may be used to assess the status and stage of a metabolic disease or condition in the subject (or in a cell or tissue sample) and/or the effect of a treatment strategy on the metabolic disease or condition in a subject (or a cell or tissue sample). Antibodies or fragments thereof that specifically bind MCJ polypeptide can be used to obtain useful prognostic information by providing an indicator of a metabolic disease or condition and can be used to select a therapy for the subject, for example, to select a drug therapy, behavioral therapy, surgical therapy, etc.

Assays described herein may include determining MCJ polypeptide activity, including but not limited to determining levels of nucleic acids that encode MCJ polypeptides and/determining levels of MCJ polypeptides in cells, tissues, and subjects. Levels of MCJ polypeptide-encoding nucleic acids and polypeptides can be determined in a number of ways when carrying out the various methods of the invention. In some embodiments of the invention, a level of MCJ polypeptide-encoding nucleic acid or polypeptide is measured in relation to a control level of MCJ-polypeptide-encoding nucleic acid or polypeptide, respectively, in a cell, tissue, or subject. One possible measurement of the level of MCJ polypeptide-encoding nucleic acid or polypeptide is a measurement of absolute levels of MCJ-polypeptide-encoding nucleic acid or polypeptide. This could be expressed, for example, in MCJ-polypeptide-encoding nucleic acid or polypeptide per unit of cells or tissue. Another measurement of a level of MCJ polypeptide-encoding nucleic acid or polypeptide is a measurement of the change in the level of MCJ-polypeptide-encoding nucleic acid or polypeptide over time. This may be expressed in an absolute amount or may be expressed in terms of a percentage increase or decrease over time. Antibodies or antigen-binding fragments or other compounds that specifically bind MCJ polypeptide or a nucleic acid that encodes MCJ polypeptide may be used in diagnostic methods alone or in conjunction with certain antibodies or binding compounds already known in the art. Known antibodies may include antibodies that specifically bind to other proteins that are associated with metabolic diseases or conditions or other cell marker proteins that may be used to quantitate the level of MCJ polypeptide-encoding nucleic acid or polypeptide per unit of cells, etc.

As mentioned above, it is also possible to use a compound of the invention (e.g., an anti-MCJ antibody or functional fragment thereof, an MCJ polypeptide-encoding nucleic acid, MCJ polypeptide, or a small molecule MCJ enhancer or inhibitor, etc.) to characterize MCJ polypeptide activity by monitoring changes in the MCJ polypeptide activity over time. For example, in certain metabolic diseases and conditions, an increase in MCJ polypeptide activity correlates with increased likelihood of a metabolic disease or condition in cells and/or tissues and in certain metabolic diseases and conditions, a decrease in MCJ polypeptide activity correlates with increased likelihood of a metabolic disease or condition in cells and/or tissues. In addition, certain metabolic diseases and conditions may not be directly characterized by abnormal MCJ polypeptide activity, but can be treated by modulating (in some increasing and in other cases decreasing) MCJ polypeptide activity. In each type of metabolic disease or condition it may be desirable to assess MCJ polypeptide activity in a treated cell, tissue, or subject.

Accordingly one can monitor MCJ polypeptide activity levels over time to determine if there is a change in status of a metabolic disease or condition in a subject or in a cell culture. Changes in MCJ polypeptide activity such as an increase or decrease in MCJ polypeptide activity that is greater than 0.1% of the baseline activity level, a previous activity level, or a control activity level may be an indicator of efficacy of, or need for, a treatment of the invention to decrease or increase, respectively, MCJ polypeptide activity.

In some embodiments of the invention, an increase in an MCJ polypeptide activity in a cell or tissue may be an increase greater than 0.2%, greater than 0.5%, greater than 1.0%, 2.0%, 3.0%, 4.0%, 5.0%, 7.0%, 10%, 15%, 20%, 25%, 30%, 40%, 50%, or more from a previous MCJ polypeptide activity in the subject. In some embodiments of the invention, a decrease in an MCJ polypeptide activity level in a cell or tissue, may be a decrease of more than 0.2%, more than 0.5%, more than 1.0%, 2.0%, 3.0%, 4.0%, 5.0%, 7.0%, 10%, 15%, 20%, 25%, 30%, 40%, 50%, or more. Increases or decreases in the MCJ polypeptide activity determinations over time may indicate a change in the status of a metabolic disease or condition in a sample or subject, efficacy of a treatment of a metabolic disease or condition, or the attainment of a desirable level of MCJ polypeptide activity in a metabolic disease or condition.

As a determination of the status of a metabolic disease or condition, methods of the invention may be used to determine MCJ polypeptide activity in two or more samples, taken at different times, and to compare the determinations to each other and/or with control MCJ polypeptide activity levels. Such comparisons may be used to determine the status of a metabolic disease or condition in a subject and allows evaluation of a treatment of a metabolic disease or condition. Comparison of a subject's MCJ polypeptide activity measured in biological samples obtained from the subject at different times and/or on different days can be used as a measure of the effectiveness of any treatment for the metabolic disease or condition in the subject. Those of ordinary skill in the art will recognize that efficacy of treatment methods and candidate therapeutics can be tested in vitro by assessing any change in MCJ polypeptide activity of a cell that occurs in response to contacting the cell with a candidate agent for treatment of a metabolic disease or condition or with a candidate agent for the modulation of MCJ polypeptide activity.

As will be appreciated by those of ordinary skill in the art, the evaluation of a treatment also may be based upon an evaluation of the symptoms or clinical end-points of a metabolic disease or condition and such evaluations can be used in conjunction with methods of the invention to assess the status of a metabolic disease or condition and/or the efficacy of a treatment of a metabolic disease or condition.

Kits

Also within the scope of the invention are kits that comprise compositions of the invention and instructions for use. Kits of the invention may include one or more of a compound such as an anti-MCJ antibody or functional fragment thereof, an MCJ polypeptide-encoding nucleic acid, MCJ polypeptide, or a small molecule MCJ enhancer or inhibitor, etc., which may be used to treat a metabolic disease or condition or in some aspects of the invention to diagnose or monitor a metabolic disease or condition. Kits containing compounds such as an anti-MCJ antibody or functional fragment thereof, an MCJ polypeptide-encoding nucleic acid, MCJ polypeptide, or a small molecule MCJ enhancer or inhibitor, etc. can be prepared for treatment methods, in vitro diagnosis, prognosis and/or monitoring the level of MCJ polypeptide activity in cells, tissues, and/or subjects using any suitable histological, cytological, serological or other method. Components of kits of the invention may be packaged either in aqueous medium or in lyophilized form. A kit of the invention may comprise a carrier being compartmentalized to receive in close confinement therein one or more container means or series of container means such as test tubes, vials, flasks, bottles, syringes, or the like. A first container means or series of container means may contain one or more compounds such as compound an anti-MCJ antibody or functional fragment thereof, an MCJ polypeptide-encoding nucleic acid, MCJ polypeptide, or a small molecule MCJ enhancer or inhibitor, etc. A second container means or series of container means may contain a targeting label or linker-label intermediate capable delivering a compound to a cell or tissue.

A kit of the invention may also include instructions. Instructions typically will be in written form and will provide guidance for carrying-out the assay or treatment embodied by the kit and for making a determination based upon that assay or treatment.

Methods to Identify Candidate Compounds

Certain aspects of the invention include methods of identifying and/or screening candidate agents that modulate MCJ polypeptide activity in cells, tissues, and/or subjects. Methods can include mixing the candidate agent with cells or tissues or in a subject and determine the MCJ polypeptide activity before and after contact with the candidate agent. An increase in the amount of MCJ polypeptide activity in comparison to a suitable control is indicative of an agent capable of increasing the level of MCJ. A decrease in the amount of MCJ polypeptide activity in comparison to a suitable control is indicative of an agent capable of decreasing the level of MCJ.

An assay mixture useful to assess a treatments candidate for a metabolic disease or disorder comprises a candidate agent. The candidate agent may be an antibody, a small organic compound, small molecule, polypeptide, nucleic acid, etc., and accordingly can be selected from combinatorial antibody libraries, combinatorial protein libraries, small organic molecule libraries, or any other suitable source. Typically, a plurality of reaction mixtures is run in parallel with different agent concentrations to obtain a different response to the various concentrations. Typically, one of these concentrations serves as a negative control, i.e., at zero concentration of agent or at a concentration of agent below the limits of assay detection.

Candidate agents that can be tested to determine whether they may be useful to modulate MCJ polypeptide activity, and may be useful to treat a metabolic disease or condition, may encompass numerous chemical classes, nucleic acids, proteins, etc. In some embodiments of the invention the candidate agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as polypeptides, saccharides, fatty acids, sterols, isoprenoids, purines, pyrimidines, derivatives or structural analogs of the above, or combinations thereof and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random polypeptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known agents may be subjected to directed or random chemical modifications such as acylation, alkylation, esterification, amidification, etc. to produce structural analogs of the agents.

A variety of other reagents also can be included in an assay mixture to test a candidate compound. These may include reagents such as salts, buffers, neutral proteins (e.g., albumin), detergents, etc., which may be used to facilitate optimal protein-protein and/or protein-agent binding. Such a reagent may also reduce non-specific or background interactions of the reaction components. Other reagents that improve the efficiency of the assay such as protease inhibitors, nuclease inhibitors, antimicrobial agents, and the like may also be used. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times may be minimized to facilitate rapid, high throughput screening, and typically are between 0.1 and 10 hours. After incubation, variables such as the presence or absence of MCJ polypeptides and MCJ polypeptide activity can be detected by any convenient method available to the user. For example, MCJ polypeptide activity can be determined through the measure of a detectable label using standard methods and as described herein.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Methods

Mice.

C57Bl/6J mice were purchased from Jackson Laboratories (Bar Harbor, Me.). MCJ targeted embryonic stem cells (RRN 226) were obtained from Baygenomics [University of California San Francisco (UCSF), San Francisco, Calif.]. The gene trapped ES cells were injected in C57B1/6J blastocysts and implanted in pseudo-pregnant females at the University of Vermont Transgenic Mouse Facility. Six male chimeras were obtained with 5 showing more than 95% chimerism. Chimeras were crossed with C57Bl/6J females and all of them led to germline transmission (100%). Mice were further backcrossed with C57Bl/6 for at least 7 generations. The heterozygous males and females were crossed for the generation of MCJ homozygous knockout. MCJ KO mice were also crossed with the previously described OT-I TCR transgenic mice (Hogquist et al., 1994 Cell 76, 17-27) and MMTV-PyMT mice (Guy et al., 1992 *Mol Cell Biol* 12, 954-961). Mice were used between 10 and 14 weeks of age. For the starvation studies, mice were kept with water but not food for 36 h. Blood, liver, kidney and brown fat were harvested. For liver cholesterol accumulation studies, the mice were kept on a high-cholesterol diet (Harlan Keklad T D. 902221) for 4 weeks as described in see Plavinskaya, T. et al., Pulm Pharmacol Ther. Effects of acute and chronic low density lipoprotein exposure on neutrophil function, Epub 2012 Oct. 17. All mice were housed under sterile conditions at the animal care facility at the University of Vermont. The procedures were approved by the University of Vermont Institutional Animal Care and Use Committee.
Cell Preparation, Culture Conditions, Proliferation and Reagents.

CD8 T cells and CD4 T cells were purified from spleen and lymph nodes by negative selection as previously described (Auphan et al., 1998 *J Immunol* 160, 4810-4821; Conze et al., 2002 *J Exp Med* 195, 811-823), and by positive selection using the MACS system as recommended by the manufacturer (Miltenyi Biotec, Cambridge, Mass.). Purified T cells were stimulated with plate-bound anti-CD3 (2C11) (5 µg/ml) and soluble anti-CD28 (1 µg/ml) (BD Biosciences, Sparks, Md.) mAbs. Proliferation assays were performed using purified CD8 T cells ($10^5$ cells/well) activated with anti-CD3 and anti-CD28 and labeled with [$^3$H]-thymidine as previously described (Conze et al., 2002 *J Exp Med* 195, 811-823). MCF7, MCF7/siMCJ, and 293T cell lines were maintained as previously described (Hatle et al., 2007 *Mol Cell Biol* 27, 2952-2966). Rotenone (used at 10 µM) was purchased from Sigma Aldrich (St. Louis, Mo.). Transfection of 293T cells by calcium phosphate was performed as previously described (Hatle et al., 2007 *Mol Cell Biol* 27, 2952-2966).

Northern Blot Analysis.

Human and Mouse multiple tissue Northern blots (MTN) were purchased from Clontech Laboratories, Inc. (Mountain View, Calif.) and contained normalized levels of PolyA RNA from different tissues. Radiolabeling of both mouse and human MCJ probes was performed as described (Rincón et al., 1988 *Eur J Immunol* November; 18(11):1791-6) and Northern blot analysis was done as per the manufacturer's instructions.

Southern Blot Analysis.

10 µg of tail genomic DNA digested with NcoI were used. DNA fragments were separated in an agarose gel, transferred onto a Hybond™ nylon membrane and radiolabeled probed with a PCR amplified region from MCJ intron 1 [5'-gtggg ggtgtctgtgaagtagttt-3' (SEQ ID NO:6) and 5'-ctgggatt-taaggagttcacaa-3' (SEQ ID NO:7)].

RNA Isolation and RT-PCR.

Total RNA was isolated using the Qiagen mini RNeasy® kit, as recommended by the manufacturer (Qiagen, Valencia, Calif.). The first strand cDNA was obtained by reverse transcription as described previously (Hatle et al., 2007 *Mol Cell Biol* 27, 2952-2966). cDNA was used to detect mouse HPRT, MCJ, beta 2 microglobulin by conventional PCR or real-time RT-PCR. For the real-time RT-PCR analysis (Applied Biosystems™, Carlsbad, Calif.) the following primers/probe designed set was used for mouse MCJ [Forward 5'-ccg aat acc tgc ctc ctt ctg-3' (SEQ ID NO:8), Reverse 5'-aca cag cgg gga gaa ggt t-3' (SEQ ID NO:9), Probe 5'-cca aag gtc gga cgc cga cat c-3' (SEQ ID NO:10)]. The relative values were determined by the comparative CT analysis method using hypoxanthine phosphoribosyltransferase (HPRT) or $\beta_2$-microglobulin as housekeeping genes. Conventional RT-PCR amplification of MCJ was done using the following primers [5'-aag taa tca cgg caa cag caa gg-3' (SEQ ID NO:11) and 5'-aat aaa agc ctg gca gcc ttg c-3' (SEQ ID NO:12)].

Western Blot Analysis.

Whole cell extracts were prepared in triton lysis buffer as previously described (Hatle et al., 2007 *Mol Cell Biol* 27, 2952-2966). Mitochondrial and cytosolic extracts were purified using the Cell Fractionation Kit Standard (MitoSciences®, Eugene, Oreg.) for CD8 T cells and MCF7 cells or the Mitochondrial Fractionation Kit (Active Motif®, Carlsbad, Calif.) for heart, tumor, and other tissues. Mitochondrial extracts were solubilized with either lauryl maltoside (1%) or digitonin (2%) when specified. Isolation of the mitochondrial inner membrane fraction was performed as previously described (see Da Cruz, S. et al., 2003 *J. Biol. Chem.* 278:41566-41571) using purified mitochondrial extracts from the heart. Western blot analyses were performed as previously described (Hatle et al., 2007 *Mol Cell Biol* 27, 2952-2966). The anti-mouse MCJ rabbit polyclonal was generated by immunization with the N-terminal peptide (35 aa) of mouse MCJ following affinity immunopurification (Cocalico Biologicals, Inc.™, Reamstown, Pa.). The anti-human MCJ mouse monoclonal Ab has already been described (Hatle et al., 2007 *Mol Cell Biol* 27, 2952-2966). Other antibodies used were: antiactin, anti-glyceraldehyde-3-phosphate dehydrogenase (anti-GAPDH), anti-rabbit IgG, anti-goat IgG, anti-mouse IgG (Santa Cruz Biotechnology, Santa Cruz, Calif.), anti-CoxIV (Cell Signaling Technology®, Danvers, Mass.), anti-NDUFA9 and anti-NDUFS3 (MitoSciences®, Eugene, Oreg.) and complex III Corel protein (MitoSciences); anti-glycogen synthase (Cell Signaling Technology®) anti-phosphoenolpyruvate carboxykinase (anti-PEPCK) (Santa Cruz Biotechnology, Dallas, Tex.); calreticulin (Enzo Life Science, Farmingdale, N.Y.); and sintaxin 11 (BD Bioscience, San Jose, Calif.). Lumi-GLO® chemiluminescent substrate system (KPL, Gaithersburg, Md.) was used to visualize the proteins. Immunoprecipitation of Complex I was performed using mitochondria extracts generated as described above and the Complex I Immunocapture monoclonal antibody (MitoSciences Eugene, Oreg.) as recommended by the manufacturer (MitoSciences °, Eugene, Oreg.). Immunoprecipitations of complex I and complex III were performed using mitochondrial extracts generated as described above and solubilized with maltoside (1%) as the detergent and the complex I or complex III Immunocapture monoclonal antibody (MitoSciences) as recommended by the manufacturer. The immunoprecipitates were then examined for the presence of MCJ, or specific subunits were examined for complex I, III, or IV subunits by Western blotting. Immunoprecipitates were then examined for the presence of MCJ and Complex I and III subunits by Western blot analysis.

Flow Cytometry Analysis.

Cell surface staining was performed using directly labeled antibodies for CD4, CD8, Thy1.1, Thy1.2, Vα2 [BD Biosciences (Sparks, Md.) and BioLegend® (San Diego, Calif.)]. Staining for cell viability was performed using the UV-Blue dye [Molecular Probes®, Inc, Life Technologies, (Beverly, Mass.)] as recommended by the manufacturer. Mitochondrial membrane potential analysis was performed by staining with Tetramethylrhodamine, Ethyl Ester, Perchlorate (TMRE) [Molecular Probes®, Inc, Life Technologies, (Beverly, Mass.)] (10 µM) for 20 min at 37° C. as recommended by the manufacturer. Mitochondrial ROS analysis was performed by staining with Mito-SOX™-Red (Invitrogen®, Life Technologies, Beverly, Mass.) (2.5 µM) for 10 min at 37° C. as recommended by the manufacturer. All samples were examined by flow cytometry analysis using an LSRII flow cytometer (BD Biosciences, Sparks, Md.) and FLOWJO® software (Flowjo, Ashland, Oreg.).

Cell sorting purification of peripheral CD4 T cells, CD8 T cells and B cells for MCJ expression was performed by staining with the Abs for CD4, CD8 and B220 (B cell marker), and the Aria Flow Cell Sorter (BD Biosciences, Sparks, Md.).

Confocal Microscopy Analysis.

Cell preparation and immunostaining of transfected 293T cells for confocal microscopy analysis were performed as we previously described (Hatle et al., 2007 *Mol Cell Biol* 27, 2952-2966). Mito Tracker® and TOPRO® [Molecular Probes®, Life Technologies, (Beverly, Mass.)] were used as markers for mitochondria and nuclei, respectively. The anti-HA tag Ab (Cell Signaling Technology®, Danvers, Mass.) was used for detection of the HA-tagged MCJ followed by the anti-rabbit secondary Ab [Molecular Probes®, Life Technologies, (Beverly, Mass.)]). Samples were examined by confocal microscopy using a Zeiss LSM 510 META confocal laser scanning imaging system (Carl Zeiss Microimaging, Thornwood, N.Y.).

Immunoelectron Microscopy Analysis.

Immunoelectron microscopy analysis for MCJ was performed as we previously described (Hatle et al., 2007 *Mol Cell Biol* 27, 2952-2966) using fixed embedded preparations of MCJ-transfected 293T cells, freshly isolated CD8 T cells or heart tissue. The anti-mouse MCJ rabbit polyclonal Ab was used for detection of MCJ.

Histology and Sera Biochemistry Analysis.

For histological analysis, liver, kidneys, brown fat and mammary tumors were harvested, fixed in formalin and paraffin embedded. Tissue sections from paraffin embedded blocks were stained with H&E according to routine procedures. Images were obtained by the Olympus® BX50 light microscope with a Magnafire® digital camera from Optronics® (Goleta, Calif.) or with the EVOS® XL Core microscope (AMG, Life Technologies, Grand Island, N.Y.). For analysis of lipid accumulation in the liver, freshly harvested livers were frozen in OCT and frozen sections were stained for Oil Red O. For histological analysis of glycogen, periodic acid-Schiff (PAS) staining was performed in paraffin-embedded liver and kidney sections. The levels of glycogen in liver extracts (corresponding to 1 mg) were determined using the Glucose (HK) Assay kit, as recommended by the manufacturer (Sigma Aldrich, Saint Louis, Mo.). Levels of triglycerides in serum were determined using the Triglyceride colorimetric kit (BioVision, Milpitas, Calif.) and ketone body kit (Cayman Chemicals, Ann Arbor, Mich.) as recommended by the manufacturers. The levels of free fatty acids (FFA) in serum and liver extracts were determined using the Free Fatty Acid quantification kit (Cayman Chemical®, Ann Arbor, Mich.) and/or free fatty acid quantification kit (BioVision, Milpitas, Calif.) as recommended by the manufacturers. The levels of cholesterol in the liver extracts (corresponding to 1 mg) were determined using the Abcam kit (Abcam, Cambridge, Mass.). Glucose levels in blood were determined using the glucose-monitoring system (LifeScan, Milpitas, Calif.).

Complex I Activity.

Analysis of complex I activity was performed using mitochondrial extracts generated following the protocol for the purification of Complex I (MitoSciences®, Eugene, Oreg.). The activity assay using the Complex I Enzyme Activity Microplate assay kit from MitoSciences® (Eugene, Oreg.) and the protocol recommended by the manufacturer. Mitochondrial extracts were normalized among samples and a total of 1 µg (heart), 5-20 µg (MCF7 and MCF7/siMCJ cells), or 1.8 µg (T cells) were used for the assay.

Intracellular ATP Levels Determination.

The levels of intracellular ATP were determined using $10^4$ cells (CD8 T cells, MCF7 cells, 293T cells) per sample and the ATPlite® Luminescence ATP Detection Assay System (PerkinElmer®, Waltham, Mass.) following the recommendations from the manufacturer and a TD-20/20 luminometer (Turner Biosystems, Promega®, Madison, Wis.). For analysis of ATP levels in mammary tumor tissue, cytosolic and mitochondria extracts were generated as described above and an amount equivalent to 10 µg of protein was assayed for ATP content using the ATPlite® kit (PerkinElmer®, Waltham, Mass.).

It has now been shown that MCJ resides in the mitochondria where it serves as a negative regulator of Complex I of the mitochondrial respiratory chain. Loss of MCJ leads to increased Complex I activity, hyperpolarization of mitochondria and increased generation of ATP. Enhanced mitochondrial oxidative phosphorylation as a source of energy in the absence of MCJ accelerates fatty acid oxidation and prevents accumulation of lipids in the liver during starvation. In addition, MCJ deficiency also delayed mammary tumor growth correlating with the inability to attenuate mitochondrial function. Thus, MCJ is an essential negative regulator of mitochondrial metabolism.

Results

Identification of Murine MCJ/DnaJC15 Reveals a Conserved Tissue Expression Pattern with the Human Ortholog.

MCJ/DnaJC15 expression has previously been examined in human ovarian and breast cancer cells (Hatle et al., 2007 *Mol Cell Biol* 27, 2952-2966; Lindsey et al., 2005 *Int J Cancer* January 15; 118(2):346-52; Shridhar et al., 2001 *Cancer Res* 61, 4258-4265; Strathdee et al., 2004 *Carcinogenesis* 25, 693-701). It was previously reported that MCJ originated in vertebrates where it is highly conserved (Hatle et al., 2007 *Mol Cell Biol* 27, 2952-2966), but no studies have reported its murine counterpart. Comparative analysis of human and mouse MCJ protein sequences showed an overall 75% identity (FIG. 1A), with nearly identical transmembrane and C-terminal DnaJ domain regions, as well as a highly conserved (57%) Nterminal region (1-35 amino acids). To identify the tissue expression pattern of murine MCJ gene, Northern blot analysis was performed using methods outlined above. MCJ mRNA was highly abundant in the heart, followed by liver and kidney (FIG. 1B). Although MCJ is expressed in some human cancer cells, the specific distribution of MCJ expression in normal human tissues remained unknown. Northern blot analysis of non-malignant human tissues showed a distribution of human mcj gene expression similar to the murine mcj gene (FIG. 1C). Previous microarray analyses performed using CD8 T cells indicated that MCJ was also present in this immune cell type (data not shown). To further investigate the expression of MCJ in the different populations of the immune system, CD4 and CD8 T cells, as well as B cells were isolated from mouse spleen and lymph nodes and performed real time reverse transcriptase (RT) PCR. Interestingly, mcj gene expression was very high in CD8 T cells, but almost undetectable in CD4 T cells and B cells (FIG. 1D).

An antibody (Ab) that specifically recognizes the N-terminal region of mouse MCJ was generated, as confirmed by Western blot analysis of 293T cells transfected with murine MCJ (FIG. 1E). The expression of endogenous MCJ protein in mouse tissues was examined by Western blot analysis using this Ab. Consistent with the mRNA expression analysis, MCJ protein was present in heart, liver and kidney, but almost undetectable in lungs (FIG. 1F). MCJ protein also was abundant in CD8 T cells, but low in CD4 T cells (FIG. 1G). Thus, it was identified that MCJ/DnaJC15 has a restricted tissue and cellular distribution.

MCJ/DnaJC15 is a Novel Mitochondrial Resident Cochaperone.

Phylogenic analyses have shown that the ancestor of MCJ is Tim14 present in yeast (Mokranjac et al., 2003 *Embo J* 22, 4945-4956). Tim14 is localized in the mitochondrial inner membrane and is a component of the TIM23 translocase (Mokranjac et al., 2005 *J Biol Chem* 280, 31608-31614). It has previously been reported that MCJ did not localize in mitochondria based on overexpression analysis of MCJ in 293T cells (that do not express endogenous MCJ) and Mito Tracker® staining using confocal microscopy (Hatle et al., 2007 *Mol Cell Biol* 27, 2952-2966). In addition, no MCJ immunostaining could be found in well-defined mitochondria by immunoelectron microscopy (IEM) in transfected 293T cells, but MCJ immunoreactivity was observed in other electron-dense uncharacterized vesicles/organelles (Hatle et al., 2007 *Mol Cell Biol* 27, 2952-2966). To more closely dissect the potential function of MCJ in normal tissue the localization of endogenous MCJ has been examined in heart under physiological conditions by IEM. Most MCJ immunoreactivity was found in clearly defined mitochondria, predominantly at the inner membrane (FIG. 2A). MCJ expression was also examined in purified CD8 T cells by IEM. The results showed that MCJ localizes almost exclusively at the mitochondria of CD8 T cells (FIG. 2B). A more detailed analysis of MCJ by IEMs in 293T cells overexpressing MCJ for 24 h revealed the presence of MCJ immunoreactivity in uncharacterized organelles that could be undefined, swollen mitochondria that have lost their inner membrane-formed cristae and undergone degradation (FIG. 2C). Confocal microscopy analysis for MCJ and Mito Tracker® in 293T cells transfected with MCJ (24 h), showed Mito Tracker® staining defining mitochondria in non-transfected cells, while mitochondrial staining was almost undetectable in MCJ-overexpressing cells (FIG. 2 D-F). Thus, MCJ was found to localize to the mitochondria under physiological conditions, but its prolonged overexpression in this organelle resulted in apparent morphological damage.

To further demonstrate the mitochondrial localization of endogenous MCJ, Western blot analysis of MCJ was performed in murine heart mitochondrial and cytosolic fractions. High levels of MCJ were found in the mitochondrial fraction while it was almost undetectable in the cytosolic fraction (FIG. 2G). The purity of the fractions was determined by the expression of Complex IV (CoxIV) of the respiratory chain as a marker of mitochondria, and GAPDH as a marker of the cytosolic fraction (FIG. 2G). MCJ was also almost exclusively present in the mitochondrial fraction of purified CD8 T cells (FIG. 2H). No MCJ could be detected in the nuclear fraction (data not shown). Furthermore, Western blot analysis of endogenous human MCJ in the breast cancer MCF7 cell line also showed the presence of MCJ primarily in mitochondria (FIG. 2I). Thus, endogenous MCJ localizes preferentially in mitochondria, and within the mitochondria it appears to be anchored to the inner membrane of the cristae.

MCJ Functions as a Negative Regulator of Mitochondrial Membrane Potential and ATP Production.

A major function of mitochondria is to provide ATP as a source of energy for the cell through oxidative phosphorylation. In addition to the transfer of electrons, Complexes I, III and IV of the mitochondria electron transfer chain (ETC) contribute to the establishment of the mitochondrial membrane potential (MMP) by promoting the transport of H+ across the membrane from the mitochondria matrix to the intermembrane space. Complex V (ATP synthase) uses the energy generated by the flow back of H+ into the mitochondrial matrix to generate ATP. To determine whether MCJ could modulate mitochondrial function, ATP levels in MCF7 breast cancer cells known to express MCJ (Hatle et al., 2007 *Mol Cell Biol* 27, 2952-2966) were compared with the levels in MCF7/siMCJ cells, MCF7 cells where MCJ expression was knocked down by a MCJ shRNA (Hatle et al., 2007 *Mol Cell Biol* 27, 2952-2966). Interestingly, the levels of ATP in MCF7/siMCJ cells were remarkably higher than in MCF7 cells (FIG. 3A). The elevated amounts of ATP in MCF7/siMCJ cells were predominantly derived from mitochondria because inhibition of the ETC Complex I with rotenone abrogated the levels of ATP (FIG. 3B). These results suggested that MCJ is a negative regulator of mitochondrial ATP synthesis. To further confirm these results, the levels of ATP were examined in 293T cells following expression of MCJ. 293T cells were transfected only for 16 h to avoid the mitochondrial damaged observed after 24 h (FIG. 2). ATP levels were highly reduced in cells expressing MCJ relative to plasmid control cells (FIG. 3C), further demonstrating that MCJ negatively regulates ATP production.

Because MCJ localizes in the inner membrane of the mitochondria, whether MCJ could impair MMP as a mechanism for limiting mitochondrial ATP synthesis was investigated. 293T cells were transfected (16 h) with MCJ or a control plasmid, and MMP was examined by TMRE staining and flow cytometry analysis. Expression of MCJ clearly depolarized mitochondria, as determined by the lower TMRE intensity (FIG. 3D), indicating that MCJ expression can dissipate MMP. A prolonged mitochondrial depolarization is likely the cause of the mitochondria damage observed in 293T cells transfected for a longer period of time (FIG. 2). Because MCJ is abundantly expressed in CD8 compared with CD4 T cells (FIG. 2), differences in MMP between the two cell types freshly isolated from wild type mice were also analyzed. Interestingly, in correlation with the selective presence of MCJ in CD8 T cells, mitochondria were depolarized in most CD8 T cells compared with mitochondria in CD4 T cells (FIG. 3E). The ETC can also contribute to the generation of mitochondrial reactive oxygen species (mROS) due to electron escape primarily from Complex III (Hamanaka and Chandel, 2010 *Trends Biochem Sci* 35, 505-513). Unlike MMP, analysis of mitochondrial ROS (mROS) by staining with MitoSox®-Red and flow cytometry showed no difference in the levels of mROS between CD4 and CD8 T cells (FIG. 3F). To further dissect the role of MCJ in mitochondrial function and determine whether the depolarized state of CD8 T cells is caused by the presence of MCJ, MCJ-deficient mice were generated.

The genotype of MCJ deficient mice was confirmed by Southern blot analysis (FIG. 4A). To confirm the loss of MCJ expression, endogenous MCJ protein levels were examined in different tissues by Western blot analysis. MCJ was detected in heart and liver from wild type mice but not in MCJ knockout (KO) mice (FIG. 4B). MCJ expression was also abrogated in CD8 T cells from MCJ KO mice (FIG. 4B). No MCJ could be detected in CD4 T cells from either wild type or MCJ KO mice (FIG. 4B). In addition, no MCJ mRNA could be detected in the MCJ targeted mice, confirming the loss of MCJ expression (FIG. 4C). MCJ mRNA levels were also reduced in the heterozygous mice compared to wild type CD8 T cells (FIG. 4C), suggesting that MCJ expression in CD8 T cells is dependent on the allele copy number. Disruption of MCJ expression did not affect the viability of the mice up to the examined age (approximately one year). Both male and female MCJ-deficient mice were fertile and did not exhibit any obvious malformations or behavioral abnormalities (data not shown). Thus, MCJ is not essential for development and/or normal organ function under physiological conditions. To demonstrate that MCJ contributes to maintaining mitochondria in a depolarized state, MMP was examined in CD8 T cells isolated from wild type and MCJ KO mice. Relative to wild type CD8 T cells, CD8 T cells from MCJ KO mice were hyperpolarized to a level comparable to wild type CD4 T cells (FIG. 3G). No difference in mROS between wild type and MCJ KO CD8 T cells could be observed (FIG. 3H). As expected, the analysis of CD4 T cells from wild type and MCJ KO mice showed no difference in MMP (FIG. 3I) or mROS (FIG. 3J), consistent with the low expression of MCJ in CD4 T cells.

Together, the results demonstrated that MCJ is a negative regulator of the mitochondria electron transfer chain, and the presence of MCJ serves to maintain mitochondria in a depolarized state and restrict mitochondrial generation of ATP. Loss of MCJ therefore leads to mitochondria hyperpolarization.

MCJ Attenuates Mitochondrial Metabolism During the Contraction Phase of Effector CD8 T Cells.

Whether the hyperpolarization of mitochondria in MCJ KO CD8 T cells relative to wild type CD8 T cells could affect their development, was examined. The percentage and number of CD8 T cells in lymph nodes (FIG. 5A) and spleen (data not shown) was not affected in MCJ knockout mice. Similarly, no difference in thymocyte populations was observed in MCJ KO mice (data not shown). Thus, MCJ does not seem to be essential for CD8 T cell development or homeostasis in the peripheral immune system. The effect that the loss of MCJ may have in the proliferative response of CD8 T cells was also examined. Purified CD8 T cells were activated with anti-CD3 and anti-CD28 antibodies. Proliferation was measured by incorporation of [$^3$H]-thymidine. No substantial difference was observed in the CD8 T cell proliferative response between MCJ KO and control wild type mice (FIG. 6A). In addition, despite the presence of MCJ in mitochondria, CD8 T cells from MCJ deficient mice did not undergo cell death more rapidly during activation (FIG. 5B). The expression of activation markers (e.g. CD69, CD44, CD25) between wild type and MCJ KO CD8 T cells during activation was also comparable (data not shown). Thus, MCJ does not seem to be required for the activation or clonal expansion of CD8 T cells. The regulation of MMP during activation of CD8 T cells with anti-CD3 and anti-CD28 Abs was further examined. MMP progressively increased in wild type CD8 T cells during activation (FIG. 6B). Although MMP also slightly increased with activation in MCJ KO CD8 T cells and wild type CD4 T cells, the effect was less pronounced due to the already highly hyperpolarized stage prior to activation (FIG. 6B). After 2 days, MMP levels in wild type CD8 T cells reached similar levels to those in activated MCJ KO CD8 T cells and wild type CD4 T cells (FIG. 4B). mROS levels were also comparable between wild type and MCJ KO CD8 T cells two days after activation (FIG. 7).

During the contraction phase of the immune response, most effector CD8 T cells die, but those that survive to eventually become memory cells undergo changes to restore their metabolism to the basal levels found in non-activated naïve CD8 T cells. MMP regulation during the transition of effector to resting stage of CD8 T cells was examined. After two days of activation with anti-CD3 and anti-CD28 Abs, wild type and MCJ KO CD8 T cells were washed and incubated in medium alone for 24 h or 48 h. After 24 h, both wild type and MCJ KO CD8 T cells remained hyperpolarized, although MMP remained slightly higher in MCJ KO CD8 T cells (FIG. 6C). Interestingly, however, after 48 h a large fraction of wild type CD8 T cells had already depolarized to levels found in naïve CD8 T cells, but most MCJ KO CD8 T cells remained hyperpolarized (FIG. 6C). Thus, MCJ was found to be required for depolarization of mitochondria during the resting stage of effector CD8 T cells, and restoring MMP to the low levels present in naïve cells. The levels of mROS also decreased overtime, but there was not a marked difference between wild type and MCJ KO CD8 T cells (FIG. 6D). It was also observed that, while wild type CD8 T cells reduced their size during the resting period to a size comparable to naïve cells, MCJ KO CD8 T cells remained larger (data not shown), suggesting that the sustained mitochondrial metabolism induced by MCJ deficiency leads to a sustained active cell metabolism. In support of this sustained active metabolism, ATP levels remained higher in MCJ-deficient than in wild type\ CD8 T cells during the resting period (FIG. 6E). To determine whether the effect of MCJ deficiency on metabolism could affect cell survival in vitro, live cell recovery was measured. Minimal survival of wild type CD8 T cells was found after 2 days resting period in vitro, while almost 100% of MCJ KO CD8 T cells remained alive (FIG. 6F), indicating that MCJ contributes to the contraction of the CD8 T cell population upon activation.

To further address the role of MCJ in the metabolism of antigen specific CD8 T cells during the transition of effector to resting stage in vivo, MCJ KO mice were crossed with OT-I TCR transgenic mice expressing a TCR that recognizes ovalbumin (Hogquist et al., 1994 Cell 76, 17-27) to generate a monoclonal T cell population. OT-I CD8 T cells purified from wild type and MCJ KO were activated and expanded in vitro. An equal number of each cell type was mixed and co-transferred into wild type host mice. After 15 days, the presence of donor cells in lymph nodes and spleen from the host mice was examined by flow cytometry analysis using Thy1.1 and Thy1.2 markers, as well as size scatter to determine cell size. Although the percentage recovery of both donors was comparable (data not shown), most wild type donor OT-1 CD8 T cells (Thy1.1+) were small as expected, while a significant fraction of the MCJ KO OT-1 CD8 T cells (Thy1.1+ Thy1.2+) displayed a large size (FIG. 6G). Thus, the result indicated that MCJ deficiency results in a prolonged active metabolic state of effector CD8 T cells in vivo in the absence of antigen, indicating that MCJ contributes to the attenuation the mitochondrial metabolism during the transition from the effector to the resting stage of CD8 T cells.

Enhanced Mitochondrial Metabolism by the Loss of MCJ Prevents Liver Steatosis During Starvation.

Figure 8A:
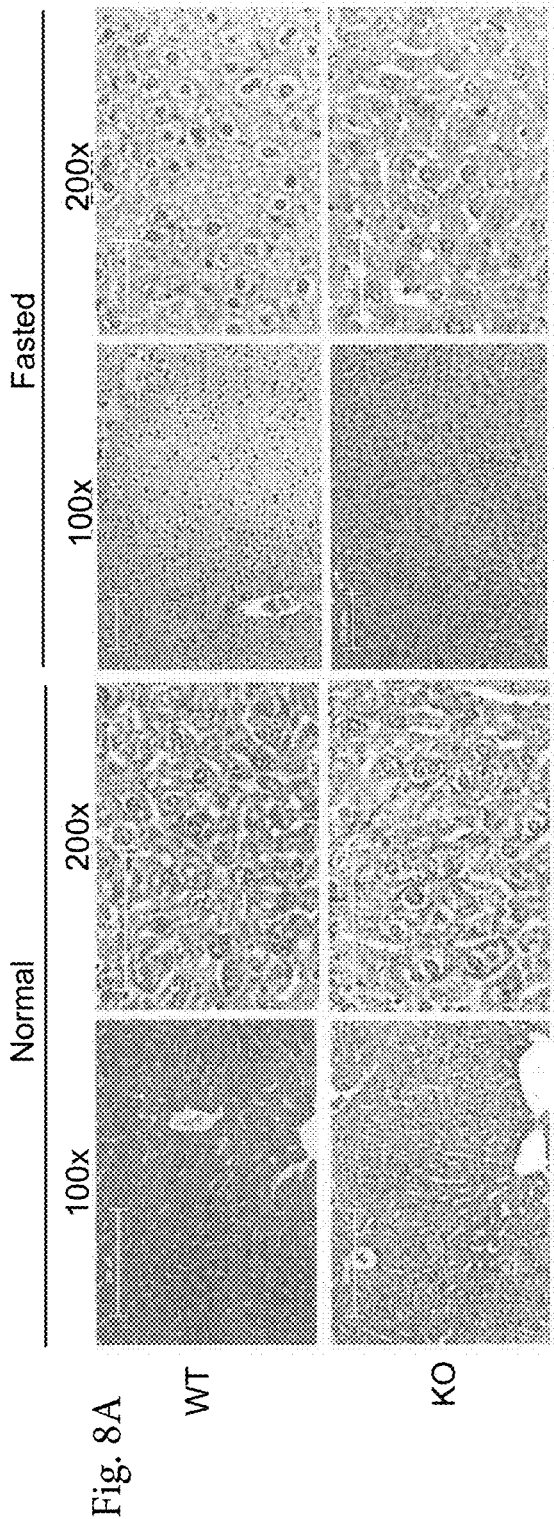
FIG. 8A-D provides photomicrographic images and graphs demonstrating that MCJ deficiency enhances liver lipid metabolism during fasting.
Figure 8B:
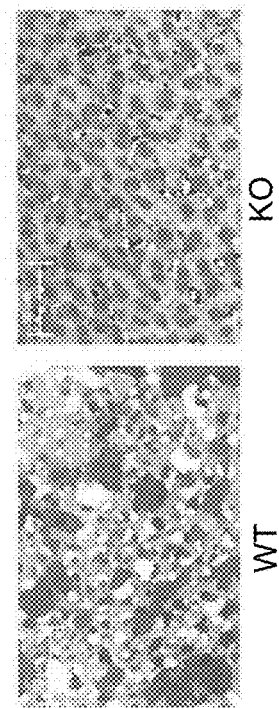
Figure 8C:
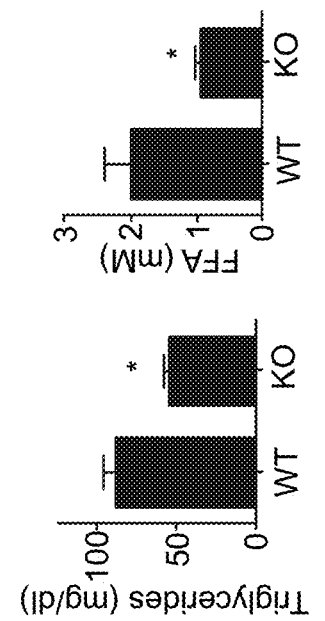
Figure 8D:
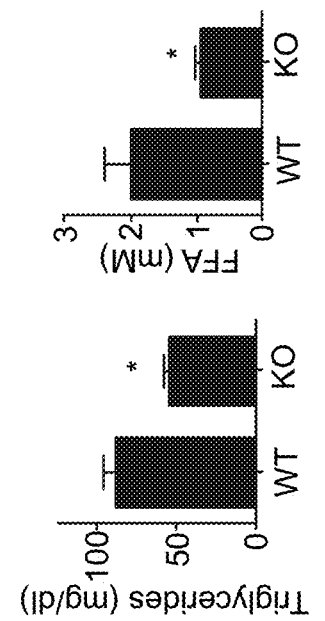
Figure 9A:
FIG. 9A-B shows photographic and photomicrographic images of brown fat in normally fed wild type and MCJ knock out (KO) mice.
Figure 9B:
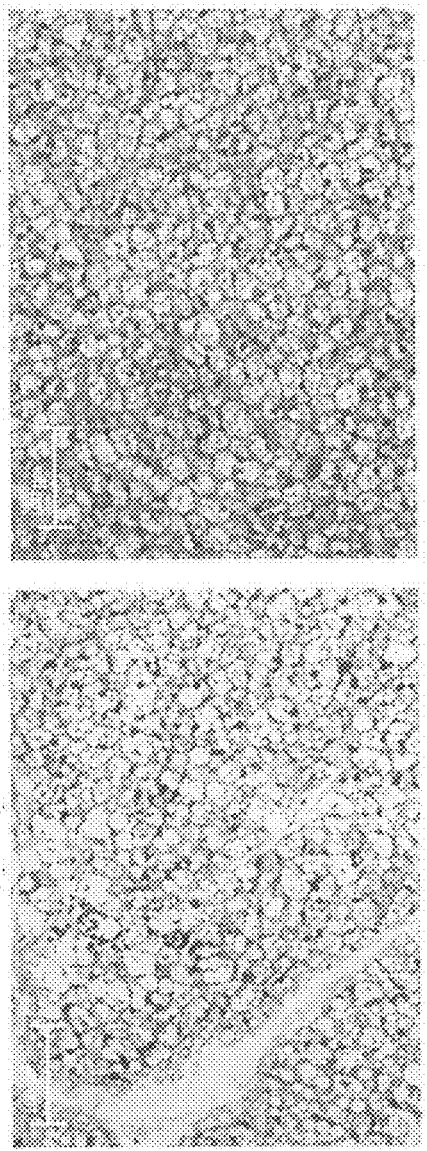
Figure 10A:
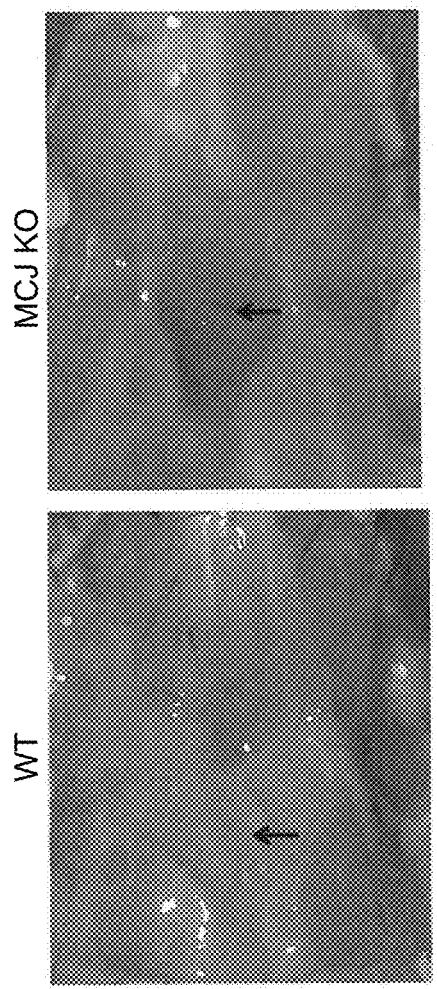
FIG. 10A-B shows photographic and photomicrographic images of brown fat in fasted wild type and MCJ knock out (KO) mice fasted for 36 hours.
Figure 10B:
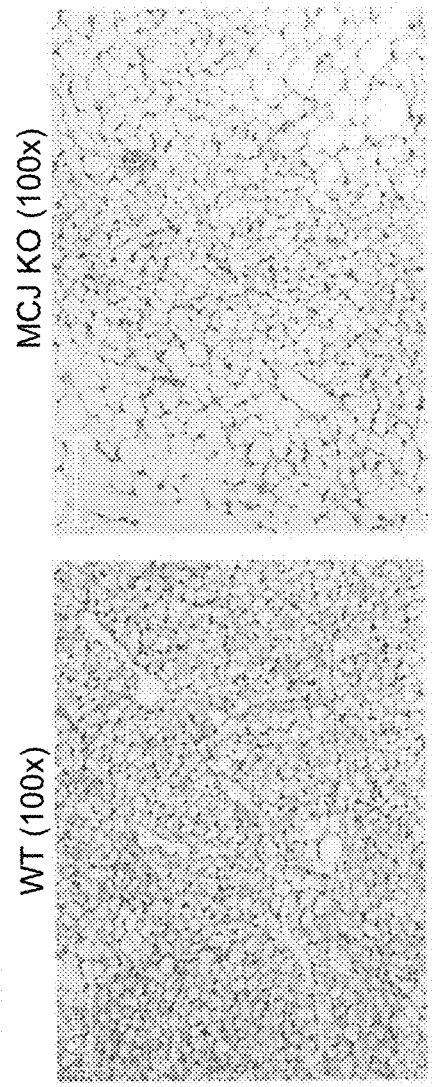

The role of MCJ attenuating mitochondrial metabolism correlates with the lack of an abnormal phenotype of MCJ deficient mice under basal (physiological) conditions. However, similar to the induction of the resting phase of effector CD8 T cells, MCJ deficiency could have an effect in situations wherein the metabolic balance is disrupted. Fasting causes drastic metabolic changes because the lack of sufficient glucose triggers the hydrolysis of triglycerides stored in the adipose tissue to free fatty acids (FFA) that are then mobilized into the plasma and transported to the liver. In the liver, FFA enter mitochondrial β-oxidation and are used as a source of energy. Because MCJ is highly expressed in the liver, it was hypothesized that increased/sustained mitochondrial metabolism in the absence of MCJ could accelerate FFA β-oxidation and minimize their accumulation in the liver. The role of MCJ in fasting metabolism was examined. Histological analysis of liver under normal (feeding) conditions showed no detectable difference between wild type and MCJ deficient mice (FIG. 8A). The livers of wild type mice fasted for 36 h showed clear signs of steatosis as determined by the presence of vacuole-enriched cells (FIG. 8A). In contrast, minimal steatotic signs were detected in livers from fasted MCJ KO mice (FIG. 8A). Analysis of lipid accumulation in frozen sections of liver by Oil Red O staining further confirmed the presence of high amounts of lipids in fasted wild type mice, while low levels were present in the livers of MCJ KO mice (FIG. 8B). These results suggested that a sustained mitochondrial oxidation of FFA in MCJ KO mice minimize the accumulation of lipids in the liver. The serum levels of triglycerides and FFA were also examined. The levels of both triglycerides (FIG. 8C) and FFA (FIG. 8D) were reduced in fasted MCJ KO mice compared with wild type mice, further demonstrating that there was an accelerated consumption of the stored lipids. Consistently, minimal white fat mass was observed to remain in fasted MCJ KO mice (data not shown). In addition, although no obvious difference was found in brown fat in normal conditions (feeding) (FIGS. 9A and 9B) between wild type and MCJ KO mice, gross analysis (FIG. 10A) and histological analysis (FIG. 10B) of brown fat after fasting revealed almost its complete absence in MCJ KO mice. Thus, as a negative regulator of mitochondrial function, the results indicated that MCJ plays a role in regulating metabolism during fasting.

Loss of MCI Prevents Lipid Accumulation and Steatosis in the Liver in Response to Metabolic Changes.

Despite accelerated metabolism identified in mice during fasting, weight loss caused by the fasting in MCJ KO nice was not statistically different from the weight loss in wild-type mice (FIG. 11A); even the initial weights were comparable in the two groups (FIG. 11B). In addition, the analysis of glucose levels in blood during fasting showed no statistically significant differences between MCJ KO and wild-type mice, either during the initial drop in glucose (12 h) (FIG. 11C) or the recovery (FIG. 11D). These results suggested the presence of mechanisms to balance the accelerated lipid metabolism in the liver in the absence of MCJ. Increased β-oxidation of free fatty acids (FFA) in the liver by mitochondria could lead to increased levels of ATP (through (3-oxidation), as well as glycerol, resulting from the lipid breakdown. The accumulation of ATP and glycerol can be sensed by the liver as a signal to initiate glycogenesis (an energy-costly process) to store the excess energy. Analysis of ATP levels in the liver after fasting was performed and confirmed increased ATP levels in the livers of MCJ KO mice relative to the livers of wild-type mice (FIG. 11E). Glycogen levels in the liver were examined by PAS staining. Glycogen was almost undetectable in the livers of fasted wild-type mice, as expected (FIG. 11F). However, high levels of glycogen accumulated in the livers of fasted MCJ KO mice (FIG. 11F). In addition to the liver, glycogenesis can occur to a lesser extent in the cortex of kidneys. Accumulation of glycogen could also be found in some areas of the kidneys in fasted MCJ KO mice by PAS staining. Biochemical analysis of glycogen in liver extracts further demonstrated the selective accumulation of glycogen in fasted MCJ KO mice (FIG. 11G). No differences were found between the basal levels of glycogen in the liver in nonfasted wild-type mice and nonfasted MCJ KO mice (FIG. 11G). The accumulation of glycogen instead of lipids in the livers of fasted MCJ KO mice correlated with an increased ratio of liver to body weight relative to wild-type mice (FIG. 11H). Glycogen is synthesized by glycogen synthase using UDP-glucose as the substrate. Glycogen synthase levels were upregulated in livers from fasted MCJ KO mice relative to wild-type mice (FIG. 11I). In contrast, the levels of phosphoenolpyruvate carboxykinase (PEPCK), an essential gluconeogenic enzyme in the synthesis of glucose from pyruvate, were comparable in fasted WT and MCJ KO mice (FIG. 11I), suggesting that the glycogen present in the livers of MCJ KO mice was likely generated with glucose resulted from triglyceride hydrolysis.

According to its negative role in mitochondrial respiration, these results show that MCJ is an essential regulator of liver metabolism during fasting and that the absence of MCJ favors lipid degradation and glycogenesis in the liver. To address whether MCJ could also play a role in regulating metabolism in response to other altered dietary conditions, its effect in response to a high-cholesterol diet was also investigated. High cholesterol is a major health problem worldwide. Wild-type and MCJ KO mice were fed a high-cholesterol diet for 4 weeks [see Plavinskaya, T. et al., *Pulm Pharmacol Ther.* 2013 August; 26(4):405-11. doi: 10.1016/j.pupt.2012.10.002. Epub 2012 Oct. 17; Teratani, T. et al., *Gastroenterology.* 2012 Jan; 142(1):152-164 (Epub 2011 Oct. 10)]. High levels of cholesterol accumulated in the livers of wild-type mice fed the high-cholesterol diet (FIG. 11J). Similar low levels of cholesterol were present in livers from wild-type and MCJ KO mice fed a normal diet (FIG. 11K). Thus, results indicated that MCJ modulates the effects caused by a variety of metabolic disorders.

MCJ Deficiency Delays Tumor Growth.

Although mitochondria respiration is the most efficient mechanism to generate ATP, in some circumstances cells choose glycolysis despite its lower efficiency. Thus, cancer cells generate their ATP from glycolysis rather than through mitochondrial oxidation even under aerobic conditions, which favors tumor growth. This phenomenon is known as Warburg effect and appears to be a metabolic adaptation of cancer cells due an impaired mitochondrial oxidative phosphorylation (Cairns et al., 2011 *Nat Rev Cancer* 11, 85-95; Koppenol et al., 2011 *Nat Rev Cancer* 11, 325-337; Warburg, 1956 *J Mol Biol* 272, 477-483). Because MCJ is a negative regulator of MMP and ATP, whether MCJ deficiency could have an impact on tumor progression in vivo was addressed. MCJ expression was examined in tumors from MMTVPyMT transgenic mice where the middle T (MT) antigen of the polyomavirus is expressed under the control of the MMTV (Mouse Mammary Tumor Virus) promoter/enhancer, which drives expression specifically in mammary epithelial cells (Guy et al., 1992 *Mol Cell Biol* 12, 954-961). MCJ was expressed both in normal mammary gland and in mammary tumors, but the levels appeared to be slightly higher in the tumors (FIG. 12A). Analysis of MCJ cellular localization in the MMTV-PyMT tumors by Western blot analysis further confirmed the mitochondrial localization of MCJ in mammary tumors (FIG. 12B). Analysis of MCJ in mitochondrial extracts from normal mammary gland and mammary tumors also confirmed an increased expression of MCJ in mitochondria from tumors compared with normal mammary gland mitochondria (FIG. 12C). MCJ KO mice were crossed with MMTV-PyMT mice and followed mammary tumor development. Interestingly, although MMTV-PyMT/MCJ KO mice developed tumors, the kinetics were delayed compared with MMTV-PyMT littermates. Consistent with previous studies (Guy et al., 1992 *Mol Cell Biol* 12, 954-961), tumors were clearly detectable by 10-12 weeks of age in MMTV-PyMT littermates, but no obvious tumors were palpable prior to 18-20 weeks in MMTV-PyMT/MCJ KO mice. Survival curves were established using the age of the mice when they had to be euthanized due to the large size tumors. They showed a significant delay in tumor growth in MMTV-PyMT/MCJ KO mice compared with MMTV-PyMT mice (FIG. 12D). Histological analysis showed no obvious differences between similar size tumors from MMTV-PyMT and MMTV-PyMT/MCJ KO mice (FIG. 12E). To address if the delay in tumor growth was associated with a change in the balance of mitochondrial respiration versus cytosolic glycolysis as sources of energy, ATP levels were examined in cytosol and mitochondrial extracts generated from wild type and MCJ KO tumors. There was a significant increase in the relative ratio of mitochondria/cytosolic ATP levels in the tumors from MCJ KO mice, compared with the ratio in tumors from wild type mice (FIG. 12F). Thus, the enhanced mitochondrial metabolism found in the absence of MCJ correlated with an impaired mammary tumor growth.

MCJ is an Endogenous Inhibitor of Complex I in the Mitochondrial Electron Transfer Chain.

To investigate the molecular mechanism by which MCJ could regulate mitochondrial membrane potential and finding potential associating proteins, a phage display screening was performed using the N-terminal region of MCJ as bait. The results from the screening revealed one of the subunits of Complex I (NDUFv1) within the mitochondria ETC as a potential interacting protein with MCJ (data not shown). Mammalian Complex I (NADH-ubiquinone oxidoreductase) contains 49 identified subunits, a flavomononucleotide (FMN) group and eight Fe—S clusters (Clason et al., 2009 *J Struct Biol* 169, 81-88). Although MCJ has not been described as an actual subunit of Complex I, it was possible that MCJ could interact with Complex I and regulate its activity. To determine whether MCJ associates with Complex I, Complex I was immunoprecipitated from mitochondrial heart extracts of wild type and MCJ KO mice. The presence of MCJ in the immunoprecipitate was examined by Western blot analysis. A band corresponding to the molecular weight of MCJ was present in the Complex I immunoprecipitate from wild type but not MCJ KO mice (FIG. 13A). As a control for the immunoprecipitation the expression of NDUFA9 and NDUFS3, two well characterized subunits of Complex I (FIG. 13A) was examined. Thus, MCJ associates with Complex I of the mitochondria.

To determine whether MCJ could be a regulator of Complex I, Complex I activity was examined in heart mitochondria extracts from wild type and MCJ deficient mice. Higher Complex I activity was detected in MCJ deficient hearts compared to wild type hearts (FIG. 13B). MCJ deficiency however, did not affect the total amount of Complex I in mitochondria as determined by Western blot analysis for NDUFA9 (FIG. 13C). The selective presence of MCJ in CD8 T cells relative to CD4 T cells also suggested a potential difference in the activity of Complex I between these cell types. Analysis of Complex I activity in mitochondria extracts obtained from freshly isolated CD8 and CD4 T cells indeed revealed substantially lower Complex I activity in CD8 T cells (FIG. 13D). The levels of NDUFA9 and NDUFS3 in the mitochondrial extracts were comparable between CD4 and CD8 T cells (FIG. 13E). More importantly, analysis of Complex I activity in MCJ KO CD8 T cells showed increased activity of the complex compared with wild type CD8 T cells (FIG. 13D). No difference in the levels of NDUFA9 or NDUFS3 in mitochondria could be detected between wild type and MCJ KO CD8 T cells (FIG. 13E). Thus, inactivation of Complex I and depolarization of mitochondria in CD8 T cells relative to CD4 T cells is mediated by the presence of MCJ in CD8 T cells. The effect of MCJ deficiency in Complex I activity was also examined in human MCF7 cells. Despite the comparable levels of Complex I in the mitochondria in both cell types (FIG. 13F), higher levels of Complex I activity were present in MCF7/siMCJ cells (lacking MCJ) compared to MCF7 cells (FIG. 13G). Together, these results showed that MCJ is an endogenous negative regulator of Complex I of the respiratory chain in mitochondria.

Studies set forth herein reveal a novel role of the MCJ/DnaJC15 co-chaperone as a negative regulator of Complex I. It has now been shown for the first time that MCJ/DnaJC15 has a role in attenuating mitochondrial metabolism and the loss of MCJ alters in vivo metabolic switches in different tissues. MCJ may therefore be a target to modulate the energy balance of the cell.

It has now been shown as outlined in part above herein, that MCJ physically associates with Complex I. The association of MCJ with Complex I is likely dynamic and could be a mechanism to rapidly modulate mitochondrial respiration in situations when the mitochondrial metabolic activity needs to be reduced (e.g. starvation, stress, etc.). This inactivation mechanism for Complex I may be play a role in those tissues where mitochondria play an essential role as a source of energy, such as the heart.

Consistent with the inhibitory role of MCJ in Complex I activity, it has now been demonstrated that the loss of MCJ results in increased mitochondrial membrane potential and increased levels of ATP. A relative increased mitochondrial metabolism should not have a significant effect under physiological conditions. In this regard, under physiological conditions MCJ deficient mice do not show an altered phenotype. However, an enhanced mitochondrial metabolism in the absence of MCJ could affect metabolic switches under stress/pathological situations and affect the course of the normal response. It has now been demonstrated through the experiments set forth herein, that MCJ deficiency alters the metabolism under fasting conditions, and it reduces the accumulation of lipids in the liver and prevents steatosis. Although not wishing to be bound by any particular mechanism, the reduction in accumulation of lipids in the liver and steatosis prevention may result by the enhancement of lipid β-oxidation. Correlating with accelerated lipolysis, less content of white fat and only residual brown fat in MCJ deficient mice was observed after fasting. Thus, in the initial phases of fasting, the enhanced mitochondrial metabolism caused by loss of MCJ can be beneficial. However, because of the rapid consumption of the available "fuel", it is thought that longer fasting periods could be highly detrimental in the absence of MCJ. Evolutionary, the acquisition of MCJ in vertebrates could have been an adaptive phenomenon to decelerate mitochondria respiration by inhibiting Complex I activity in response to insufficient intake of food, and prolong the lipid reserve energy.

Metabolism is also emerging as an important factor that can influence the survival and/or function of T cells. Oxidation of fatty acids and the metabolic rate influence survival of memory CD8 T cells (Araki et al., 2009 *Nature* 460, 108-112; Maines et al., 2009 *Science* 325, 484-487; Finlay and Cantrell, 2010 *Nat Rev Immunol* 11, 109-117). In addition, a recent study has shown that IL-15, a well-known survival factor for memory CD8 T cells, promotes mitochondrial oxidative metabolism and ATP production in memory cells by enhancing mitochondrial biogenesis (van der Windt et al., 2012 *Immunity* 36, 68-78). Increase mitochondrial fatty acid oxidation correlates with increased survival and function of memory CD8 T cells. Here we show that MCJ contributes to the inactivation of Complex I and, consequently, depolarization of mitochondria in CD8 T cells. More importantly, it has now been shown that the absence of MCJ during the resting period of effector CD8 T cells sustains an active mitochondrial metabolism in these cells in vitro and in vivo. Thus, MCJ may also regulate memory CD8 T cell function. CD4 and CD8 T cells prior to activation have been historically considered very similar to each other. Studies presented herein show for the first time a predominant expression of MCJ in CD8 T cells relative to CD4 T cells, and a drastic mitochondrial depolarization in CD8 T cells maintained by the presence of MCJ in this these cells. These revealing findings demonstrate a clear dissociation between CD4 and CD8 T cells regarding mitochondrial metabolism.

Although under physiological conditions most cells use mitochondria respiration as a mechanism to generate ATP, tumor cells switch to glycolysis as a mechanism to obtain ATP despite being less efficient, a phenomenon known as Warburg effect. Warburg hypothesized that the metabolic switch to glycolysis in cancer cells could be due to damaged mitochondrial respiration, but the actual mechanism remains unclear. In recent years the Warburg effect has been broadly reconsidered based on results from basic and clinical studies (Cairns et al., 2011 *Nat Rev Cancer* 11, 85-95; Koppenol et al., 2011 *Nat Rev Cancer* 11, 325-337; Levine and Puzio-Kuter, 2010 *Science* 330, 1340-1344). Thus, while enhanced or prolonged mitochondrial respiration could be beneficial for many cells, it could also interfere with tumor growth. Here it is now shown that MCJ deficiency delays in vivo mammary tumor growth, correlating with a modified balance towards mitochondrial respiration as a source of energy. A number of in vitro and/or xenograft studies have addressed the role of co-chaperones (e.g. Tid1, MRJ, HLAJ1) in cancer and assign them a predominant tumor suppressor function by interfering with cell invasion, migration, and/or metastasis (Sterrenberg et al., 2011 *Cancer Lett* 312, 129-142). None of these co-chaperones have been associated with changes in the metabolic state of the tumor cells. The work described herein includes the first study showing the effect of a co-chaperone in vivo tumor progression due to changes in the metabolic state. It has previously been shown that loss of MCJ is associated with chemoresistance in breast and ovarian cancer (Hatle et al., 2007 *Mol Cell Biol* 27, 2952-2966; Strathdee et al., 2005 *Gynecol Oncol* 97, 898-903). Based on findings described herein, it appears possible that the enhanced Complex I activity and mitochondria metabolism in the absence of MCJ could also confer resistance to specific cancer drugs.

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated herein in their entirety herein by reference.

The invention claimed is:

1. A method of increasing mitochondrial metabolism in a kidney cell, the method comprising contacting the kidney cell with an MCJ-modulating compound comprising an MCJ siRNA that decreases MCJ polypeptide activity in the kidney cell, in an amount effective to increase mitochondrial metabolism in the kidney cell.

2. The method of claim 1, wherein decreasing the MCJ polypeptide activity comprises decreasing a level or function of MCJ polypeptide in the kidney cell.

3. The method of claim 1, wherein mitochondrial metabolism comprises mitochondrial respiration.

4. The method of claim 1, wherein the increased mitochondrial metabolism reduces lipid accumulation in the kidney cell.

5. The method of claim 1, wherein the MCJ-modulating compound further comprises a targeting agent.

* * * * *

SEQUENCE LISTING

<160> NUMBER OF SEQ ID NOS: 12

<210> SEQ ID NO 1
<211> LENGTH: 150
<212> TYPE: PRT
<213> ORGANISM: Homo sapiens

<400> SEQUENCE: 1

```
Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30

Gln Gln Gly Leu Val Arg Ser Leu Ile Ala Val Gly Leu Gly Val Ala
        35                  40                  45

Ala Leu Ala Phe Ala Gly Arg Tyr Ala Phe Arg Ile Trp Lys Pro Leu
    50                  55                  60
```

Glu Gln Val Ile Thr Glu Thr Ala Lys Lys Ile Ser Thr Pro Ser Phe
65                  70                  75                  80

Ser Ser Tyr Tyr Lys Gly Gly Phe Glu Gln Lys Met Ser Arg Arg Glu
                85                  90                  95

Ala Gly Leu Ile Leu Gly Val Ser Pro Ser Ala Gly Lys Ala Lys Ile
            100                 105                 110

Arg Thr Ala His Arg Arg Val Met Ile Leu Asn His Pro Asp Lys Gly
        115                 120                 125

Gly Ser Pro Tyr Val Ala Ala Lys Ile Asn Glu Ala Lys Asp Leu Leu
    130                 135                 140

Glu Thr Thr Thr Lys His
145                 150

<210> SEQ ID NO 2
<211> LENGTH: 1074
<212> TYPE: DNA
<213> ORGANISM: Homo sapiens
<220> FEATURE:
<221> NAME/KEY: misc_feature
<223> OTHER INFORMATION: Homo sapiens DNAJ domain-containing protein MCJ
      (MCJ) mRNA, complete cds

<400> SEQUENCE: 2
ggtcaggaaa gctcaggcaa gcccaccctc aggcattaca gctagactcc gagcttactg      60
ggcagtcatc tgattcgacc aacatcagtt cgcagggctt aagcccagtc ccttacggcg     120
gctggggagg gaccaggccc aagtatataa agctccctga gggtccgcgt tggctttgcg     180
cctgtgagtg tgattcaaga acgtcccagt gcccttggct cctttcggag tgtgaccccg     240
tgcttgcacg ggacacgtta cccagctcgg gtgagaaggg tatcttccgg gaacctcgcc     300
tttaatagca caacgagcgc agagtccact ggatctgcga gaagaaaccg cgctaactag     360
tttgtcccta cggccgcctc gtagtcactg ccgcggcgcc ttgagtctcc gggccgcctt     420
gccatggctg cccgtggtgt catcgctcca gttggcgaga gtttgcgcta cgctgagtac     480
ttgcagccct cggccaaacg gccagacgcc gacgtcgacc agcagggact ggtaagaagt     540
ttgatagctg taggactggg tgttgcagct cttgcatttg caggtcgcta cgcatttcgg     600
atctggaaac tctagaaca agttatcaca gaaactgcaa agaagatttc aactcctagc      660
ttttcatcct actataaagg aggatttgaa cagaaaatga gtaggcgaga agctggtctt     720
attttaggtg taagcccatc tgctggcaag gctaagatta gaacagctca taggagagtc     780
atgattttga atcacccaga taaaggtgga tctccttacg tagcagccaa aataaatgaa     840
gcaaaagact tgctagaaac aaccaccaaa cattgatgct taaggaccac actgaaggaa     900
aaaaaaagag gggacttcga aaaaaaaaaa agccctgcaa aatattctaa acatggtct      960
tcttaatttt ctatatggat tgaccacagt cttatcttcc accattaagc tgtataacaa    1020
taaaatgtta atagtcttgc tttttattat cttttaaaga tctccttaaa ttct          1074

<210> SEQ ID NO 3
<211> LENGTH: 149
<212> TYPE: PRT
<213> ORGANISM: Mus muscula

<400> SEQUENCE: 3

Met Ala Thr Gly Gly Gly Val Thr Ser Arg Glu Ser Leu Arg Tyr Ala
1               5                   10                  15

Glu Tyr Leu Pro Pro Ser Ala Gln Arg Ser Asp Ala Asp Ile Asp His
            20                  25                  30

```
Thr Ala Gly Arg Arg Leu Ile Ala Val Gly Leu Gly Val Ala Ala Val
        35                  40                  45

Ala Phe Ala Gly Arg Tyr Ala Phe Gln Ile Trp Lys Pro Leu Glu Gln
 50                  55                  60

Val Ile Thr Ala Thr Ala Arg Lys Ile Ser Ser Pro Ser Phe Ser Ser
 65                  70                  75                  80

Tyr Tyr Lys Gly Gly Phe Glu Gln Lys Met Ser Lys Arg Glu Ala Ser
                85                  90                  95

Leu Ile Leu Gly Val Ser Pro Ser Ala Gly Lys Ala Lys Ile Arg Thr
            100                 105                 110

Ala His Lys Arg Ile Met Ile Leu Asn His Pro Asp Lys Gly Gly Ser
            115                 120                 125

Pro Tyr Val Ala Ser Lys Ile Asn Glu Ala Lys Asp Leu Leu Glu Ala
            130                 135                 140

Ser Ser Lys Ala Asn
145

<210> SEQ ID NO 4
<211> LENGTH: 150
<212> TYPE: PRT
<213> ORGANISM: Homo sapiens

<400> SEQUENCE: 4

Met Ala Ala Arg Gly Val Ile Ala Pro Val Gly Glu Ser Leu Arg Tyr
 1               5                  10                  15

Ala Glu Tyr Leu Gln Pro Ser Ala Lys Arg Pro Asp Ala Asp Val Asp
            20                  25                  30

Gln Gln Arg Leu Val Arg Ser Leu Ile Ala Val Gly Leu Gly Val Ala
            35                  40                  45

Ala Leu Ala Phe Ala Gly Arg Tyr Ala Phe Arg Ile Trp Lys Pro Leu
 50                  55                  60

Glu Gln Val Ile Thr Glu Thr Ala Lys Lys Ile Ser Thr Pro Ser Phe
 65                  70                  75                  80

Ser Ser Tyr Tyr Lys Gly Gly Phe Glu Gln Lys Met Ser Arg Arg Glu
                85                  90                  95

Ala Gly Leu Ile Leu Gly Val Ser Pro Ser Ala Gly Lys Ala Lys Ile
            100                 105                 110

Arg Thr Ala His Arg Arg Val Met Ile Leu Asn His Pro Asp Lys Gly
            115                 120                 125

Gly Ser Pro Tyr Val Ala Ala Lys Ile Asn Glu Ala Lys Asp Leu Leu
            130                 135                 140

Glu Thr Thr Thr Lys His
145                 150

<210> SEQ ID NO 5
<211> LENGTH: 2404
<212> TYPE: DNA
<213> ORGANISM: Homo sapiens
<220> FEATURE:
<221> NAME/KEY: misc_feature
<223> OTHER INFORMATION: Homo sapiens DnaJ (Hsp40) homolog, subfamily C,
      member 15, mRNA (cDNA clone MGC:110875 IMAGE:30530999), complete
      cds

<400> SEQUENCE: 5
agtctccggg ccgccttgcc atggctgccc gtggtgtcat cgctccagtt ggcgagagtt      60
tgcgctacgc tgagtacttg cagccctcgg ccaaacggcc agacgccgac gtcgaccagc     120
```

```
agagactggt aagaagtttg atagctgtag gcctgggtgt tgcagctctt gcatttgcag      180
gtcgctacgc atttcggatc tggaaacctc tagaacaagt tatcacagaa actgcaaaga      240
agatttcaac tcctagcttt tcatcctact ataaggagg atttgaacag aaaatgagta       300
ggcgagaagc tggtcttatt ttaggtgtaa gcccatctgc tggcaaggct aagattagaa      360
cagctcatag gagagtcatg attttgaatc acccagataa aggtggatct ccttacgtag      420
cagccaaaat aaatgaagca aaagacttgc tagaaacaac caccaaacat tgatgcttaa      480
ggaccacact gaaggaaaaa aaagagggg acttcaaaaa aaaaaaaaaa gccctgcaaa       540
atattctaaa acatggtctt cttaatttc tatatggatt gaccacagtc ttatcttcca       600
ccattaagct gtataacaat aaaatgttaa tagtcttgct ttttattatc ttttaaagat      660
ctccttaaat tctataactg atcttttttc ttatttgtt tgtgacattc atacattttt       720 aagattttg ttatgttctg aattcccccc tacacacaca cacacacaca cacacacaca      780
cgtgcaaaaa atatgatcaa gaatgcaatt gggatttgtg agcaatgagt agacctctta      840
ttgtttatat ttgtaccctc attgtcaatt ttttttttagg gaatttggga ctctgcctat      900
ataaggtgtt ttaaatgtct tgagaacaag cactggctga tacctcttgg agatatgatc      960
tgaaatgtaa tggaatttat taaatggtgt ttagtaaagt aggggttaag gacttgttaa     1020
agaaccccac tatctctgag acccttatagc caaagcatga ggacttggag agctactaaa    1080
atgattcagg tttacaaaat gagccctgtg aggaaaggtt gagagaagtc tgaggagttt     1140
gtatttaatt atagtcttcc agtactgtat attcattcat tactcattct acaaatattt     1200
attgacccct tttgatgtgc aaggcactat cgtgcgtccc ctgagagttg caagtatgaa     1260
gcagtcatgg atcatgaacc aaaggaactt atatgtagag gaaggataaa tcacaaatag     1320
tgaatactgt tagatacaga tgatatattt taaaagttca aggaagaaa agaatgtgtt      1380 aaacactgca tgagaggagg aataagtggc atagagctag gctttagaaa agaaaaatat     1440
tccgatacca tatgattggt gaggtaagtg ttattctgag atgagaatta gcagaaatag     1500
atatatcaat cggagtgatt agagtgcagg gtttctggaa agcaaggttt ggacagagtg     1560
gtcatcaaag gccagccctg tgacttacac tgcattaaat taatttctta gaacatagtc     1620
cctgatcatt atcactttac tattccaaag gtgagagaac agattcagat agagtgccag     1680
cattgtttcc cagtattcct ttacaaatct tgggttcatt ccaggtaaac tgaactactg     1740
cattgtttct atcttaaaat acttttaga tatcctagat gcatctttca acttctaaca     1800
ttctgtagtt taggagttct caaccttggc attattgaca tgttaggcca ataattttt      1860 tttgtgggag gtctcttgtg cgttttagat gattagcaat aatccctgac ctgttatcta     1920
ctaaagacta gtcgtttctc atcagttgtg acaacaaaaa tggttccaga tattgccaaa     1980 tgcccttag aggacagtaa tcgcccccag ttgagaacca tttcagtaaa actttaatta     2040
ctattttttc ttttggttta taaataatg atcctgaatt aaattgatgg aaccttgaag     2100
tcgataaaat atatttcttg ctttaaagtc cccatacgtg tcctactaat tttctcatgc     2160
tttagtgttt tcacttttct cctgttatcc ttgtacctaa gaatgccatc ccaatcccca     2220
gatgtccacc tgcccaaagt ctaggcatag ctgaaggcca agctaaaatg tatccctctt     2280
tttctggtac atgcagcaaa agtaatatga attatcagct ttctgagagc aggcattgta     2340
tctgtcttgt ttggtgttac attggcaccc aataaatatt tgttgagcga aaaaaaaaaa     2400
aaaa                                                                  2404
```

<210> SEQ ID NO 6
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 6
gtgggggtgt ctgtgaagta gttt                                              24

<210> SEQ ID NO 7
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 7
ctgggattta aggagttcac aa                                                22

<210> SEQ ID NO 8
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 8
ccgaatacct gcctccttct g                                                 21

<210> SEQ ID NO 9
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 9
acacagcggg gagaaggtt                                                    19

<210> SEQ ID NO 10
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 10
ccaaaggtcg gacgccgaca tc                                                22

<210> SEQ ID NO 11
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 11
aagtaatcac ggcaacagca agg                                               23

<210> SEQ ID NO 12
<211> LENGTH: 22
<212> TYPE: DNA
<213> ORGANISM: Artificial Sequence
<220> FEATURE:
<223> OTHER INFORMATION: Synthetic Oligonucleotide

```
<400> SEQUENCE: 12
aataaaagcc tggcagcctt gc                                              22
```